(12) United States Patent
Hinze et al.

(10) Patent No.: US 7,759,385 B2
(45) Date of Patent: Jul. 20, 2010

(54) 4-SUBSTITUTED 1-AMINOCYCLOHEXANE COMPOUNDS FOR UTILIZATION AS ORL1-RECEPTOR AND MU-OPIATE RECEPTOR LIGANDS

(75) Inventors: Claudia Hinze, Aachen (DE); Hans Schick, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 1083 days.

(21) Appl. No.: 11/125,151

(22) Filed: May 10, 2005

(65) Prior Publication Data

US 2005/0277674 A1    Dec. 15, 2005

Related U.S. Application Data

(63) Continuation of application No. PCT/EP03/12306, filed on Nov. 5, 2003.

(30) Foreign Application Priority Data

Nov. 11, 2002   (DE) ................................ 102 52 666

(51) Int. Cl.
*A61K 31/405*    (2006.01)
*C07D 209/04*    (2006.01)
(52) U.S. Cl. ...................... 514/415; 548/469; 548/503; 548/565
(58) Field of Classification Search ................. 514/415; 548/469, 503, 565
See application file for complete search history.

(56) References Cited

U.S. PATENT DOCUMENTS

| | | | |
|---|---|---|---|
| 4,113,866 A | | 9/1978 | Lednicer |
| 5,760,023 A | * | 6/1998 | Farrar et al. .................. 514/150 |
| 6,172,067 B1 | | 1/2001 | Kondo et al. |
| 6,180,623 B1 | * | 1/2001 | Kruse et al. ............. 514/212.02 |
| 7,173,045 B2 | * | 2/2007 | Sundermann et al. ....... 514/330 |
| 2002/0128288 A1 | | 9/2002 | Kyle et al. |

FOREIGN PATENT DOCUMENTS

| | | |
|---|---|---|
| EP | 1 323 710 | 7/2003 |
| WO | WO 01/87838 | 11/2001 |
| WO | WO 02/30891 A1 | 4/2002 |

OTHER PUBLICATIONS

Castro et al. "Synthesis of aryl amido . . . " CA 136:5907 (2001).*
Seddon "Pseudopolymorph . . . " Crystal growth and design 496) 1087 (2004) (internet print out 2 pages).*
Braga et al. "Making crystals from . . . " Chem. Commun. p. 3635-3645 (2005).*
Clark et al. "Highly selective . . . " J. Med. Chem. p. 831-836 (1988).*
Lednicer "Analygetic compounds . . . " CA 90:86991 (1979).*
Meng et al. "Preparation of thiophene . . . " CA 128:34681 (1997).*
Mothes et al. "Amino-zinc . . . " CA 149:268295 (2008).*
Exhibit I "STN searh result" (2009).*
German Search Report Dated Dec. 2, 2005 With English Translation of Relevant Portion (Five (5) pages).

* cited by examiner

*Primary Examiner*—Celia Chang
(74) *Attorney, Agent, or Firm*—Crowell & Moring, LLP

(57) ABSTRACT

The invention relates to 4-substituted 1-aminocyclohexane corresponding to formula (I)

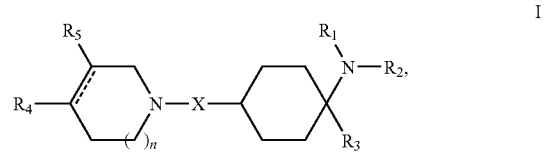

to a method for the production thereof, to pharmaceutical formulations containing these compounds and to the utilization of 4-substituted 1-aminocyclohexane compounds for the production of pharmaceutical formulations and related methods of treatment.

22 Claims, No Drawings

4-SUBSTITUTED 1-AMINOCYCLOHEXANE COMPOUNDS FOR UTILIZATION AS ORL1-RECEPTOR AND MU-OPIATE RECEPTOR LIGANDS

CROSS REFERENCE TO RELATED APPLICATIONS

This application is a continuation of International Patent Application No. PCT/EP2003/012306, filed Nov. 5, 2003, designating the United States of America, and published in German as WO 2004/043949 A1, the entire disclosure of which is incorporated herein by reference. Priority is claimed based on Federal Republic of Germany Patent Application No. 102 52 666.4, filed Nov. 11, 2002.

FIELD OF THE INVENTION

The present invention relates to 4-substituted 1-aminocyclohexane compounds, processes for their preparation, pharmaceutical formulations containing these compounds and the use of 4-substituted 1-aminocyclohexane derivatives for the production of pharmaceutical formulations and in related methods of treatment.

BACKGROUND OF THE INVENTION

The heptadecapeptide nociceptin is an endogenous ligand of the ORL1 (opioid receptor-like) receptor (Meunier et al., Nature 377, 1995, pp. 532-535), which belongs to the family of opioid receptors and can be found in many regions of the brain and spinal cord and has a high affinity for the ORL1 receptor. The ORL1 receptor is homologous to the μ, κ and δ opioid receptors and the amino acid sequence of the nociceptin peptide bears a marked similarity to those of the known opioid peptides. The activation of the receptor induced by nociceptin leads via the coupling with $G_{i/o}$, proteins to an inhibition of adenylate cyclase (Meunier et al., Nature 377, 1995, pp. 532-535).

The nociceptin peptide exhibits after intercerebroventicular application a pronociceptive and hyperalgesic activity in various animal models (Reinscheid et al., Science 270, 1995, pp. 792-794). These findings can be interpreted as an inhibition of stress-induced analgesia (Mogil et al., Neuroscience 75, 1996, pp. 333-337). In this connection an anxiolytic activity of nociceptin was also detected (Jenck et al., Proc. Natl. Acad. Sci. USA 94, 1997, 14854-14858).

On the other hand, an antinociceptive effect of nociceptin was also found in various animal models, especially after intrathecal application. Nociceptin has an antinociceptive effect in various pain models, for example in the tail flick test in mice (King et al., Neurosci. Lett., 223, 1997, 113-116). An antinociceptive action of nociceptin was likewise detected in models of neuropathic pain, which is particularly interesting since the efficacy of nociceptin increases after axotomy of spinal nerves. This is in contrast to conventional opioids, whose efficacy decreases under these conditions (Abdulla and Smith, J. Neurosci., 18, 1998, pp. 9685-9694).

The ORL1 receptor is also involved in the regulation of further physiological and pathophysiological processes. These include inter alia learning and memory formation (Manabe et al., Nature, 394, 1997, pp. 577-581), hearing ability (Nishi et al., EMBO J., 16, 1997, pp. 1858-1864) as well as numerous other processes. In a review article by Calo et al. (Br. J. Pharmacol., 129, 2000, 1261-1283) a survey is given of the indications or biological processes in which the ORL1 receptor plays a role, or may with a high degree of probability play a rôle. The following inter alia are mentioned: analgesia, stimulation and regulation of food intake, influence on μ agonists such as morphine, treatment of withdrawal symptoms, reduction of the addictive potential of opioids, anxiolysis, modulation of motor activity, memory disturbances, epilepsy; modulation of neurotransmitter secretion, in particular of glutamate, serotonin and dopamine, and concomitant neurodegenerative diseases; influencing of the cardiovascular system, initiation of an erection, diuresis, antinatriuresis, electrolyte balance, arterial blood pressure, hydropexic disorders, intestinal motility (diarrhoea), relaxing effects on the respiratory pathways and micturition reflex (urinary incontinence). The use of agonists and antagonists as anorectics and analgesics (also in combined administration with opioids) or nootropics is furthermore discussed.

The possible uses of compounds that bind to the ORL1 receptor and activate or inhibit the latter are accordingly multifarious. Apart from this, opioid receptors such as the μ receptor and other sub-types play an important role, specifically in the area of pain treatment, but also in other of the aforementioned medical indications. Accordingly, it is beneficial if a compound also acts on these opioid receptors.

SUMMARY OF THE INVENTION

One object of certain embodiments of the present invention is to provide pharmaceutical formulations that act on the nociceptin/ORL1 receptor system and/or on the μ opiate receptor and are thus suitable for pharmaceutical formulations in particular for treating the various medical conditions that are connected with this system, or are suitable for use in the related indications mentioned in the prior art.

The present invention accordingly provides 4-substituted 1-aminocyclohexane compounds corresponding to formula I

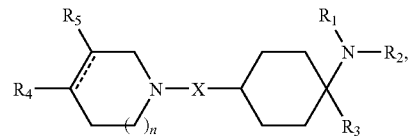

wherein
n=0, 1 or 2,
X denotes a bond or C(O), C(O)NH, C(O)CH$_2$, C(O)CH= or C(O)NHCH$_2$,
R$^1$ and R$^2$ independently of one another denote H; C$_{1-8}$-alkyl or C$_{3-8}$-cycloalkyl, in each case saturated or unsaturated, branched or unbranched, singly or multiply substituted or unsubstituted; aryl or heteroaryl, in each case singly or multiply substituted or unsubstituted; or aryl, C$_{3-8}$-cycloalkyl or heteroaryl bonded via C$_{1-3}$-alkyl, in each case singly or multiply substituted or unsubstituted,
or the radicals R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$, in which R$^6$ denotes H; C$_{1-8}$-alkyl or C$_{3-8}$-cycloalkyl, in each case saturated or unsaturated, branched or unbranched, singly or multiply substituted or unsubstituted; aryl or heteroaryl, in each case singly or multiply substituted or unsubstituted; or aryl, C$_{3-8}$-cycloalkyl or heteroaryl bound via C$_{1-3}$-alkyl, in each case singly or multiply substituted or unsubstituted;
R$^3$ denotes C$_{1-8}$-alkyl or C$_{3-8}$-cycloalkyl, in each case saturated or unsaturated, branched or unbranched, singly or multiply substituted or unsubstituted; aryl, heteroaryl, in each case unsubstituted or singly or multiply substituted; aryl, $C_{3-8}$-cycloalkyl or heteroaryl bonded via a saturated or unsaturated, branched or unbranched, substituted or unsubstituted $C_{1-4}$-alkyl group, in each case unsubstituted or singly or multiply substituted;

$R^4$ and $R^5$ independently of one denote H; $C_{1-6}$-alkyl, $OC_{1-3}$-alkyl, in each case branched or unbranched, saturated or unsaturated, unsubstituted or singly or multiply substituted; F, Cl, Br, I, OH, SH, $SCH_3$, $OCH_3$, $NH_2$, COOH, $COOCH_3$, $NHCH_3$ or $N(CH_3)_2$ or $NO_2$, or $(CH_2)_m R^7$, in which m=0-6 and $R^7$ denotes H; $C_{3-8}$-cycloalkyl, aryl or heteroaryl, in each case unsubstituted or singly or multiply substituted, optionally in the form of their racemates, their pure stereoisomers, in particular enantiomers or diastereomers, or in the form of mixtures of the stereoisomers, in particular of the enantiomers or diastereomers, in an arbitrary mixture ratio; in the form of their acids or their bases or in the form of their salts, in particular of the physiologically compatible salts or salts of physiologically compatible acids or cations; or in the form of their solvates, in particular the hydrates.

All these compounds according to the invention exhibit a good binding to the ORL1 receptor, but also to other opiate receptors, in particular to the μ opiate receptor.

Within the context of the present invention alkyl and cycloalkyl radicals are understood to denote saturated and unsaturated (but not aromatic), branched, unbranched and cyclic hydrocarbons, which may be unsubstituted or singly or multiply substituted. In this connection $C_{1-2}$-alkyl denotes C1- or C2-alkyl, $C_{1-3}$-alkyl denotes C1-, C2- or C3-alkyl, $C_{1-4}$-alkyl denotes C1-, C2-, C3- or C4-alkyl, $C_{1-5}$-alkyl denotes C1-, C2-, C3-, C4- or C5-alkyl, $C_{1-6}$-alkyl denotes C1-, C2-, C3-, C4-, C5- or C6-alkyl, $C_{1-7}$-alkyl denotes C1-, C2-, C3-, C4-, C5-, C6- or C7-alkyl, $C_{1-8}$-alkyl denotes C1-, C2-, C3-, C4-, C5-, C6-, C7- or C8-alkyl, $C_{1-10}$-alkyl denotes C1-, C2-, C3-, C4-, C5-, C6-, C7-, C8,- C9- or C10-alkyl and $C_{1-18}$-alkyl denotes C1-, C2-, C3-, C4-, C5-, C6-, C7-, C8,- C9-, C10-, C11-, C12-, C13-, C14-, C15-, C16-, C17- or C18-alkyl. In addition $C_{3-4}$-cycloalkyl denotes C3- or C4-cycloalkyl, $C_{3-5}$-cycloalkyl denotes C3-, C4- or C5-cycloalkyl, $C_{3-6}$-cycloalkyl denotes C3-, C4-, C5- or C6-cycloalkyl, $C_{3-7}$-cycloalkyl denotes C3-, C4-, C5-, C6- or C7-cycloalkyl, $C_{3-8}$-cycloalkyl denotes C3-, C4-, C5-, C6-, C7- or C8-cycloalkyl, $C_{4-5}$-cycloalkyl denotes C4- or C5-cycloalkyl, $C_{4-6}$-cycloalkyl denotes C4-, C5- or C6-cycloalkyl, $C_{4-7}$-cycloalkyl denotes C4-C5-, C6- or C7-cycloalkyl, $C_{5-6}$-cycloalkyl denotes C5- or C6-cycloalkyl and $C_{5-7}$-cycloalkyl denotes C5-, C6- or C7-cycloalkyl. With regard to cycloalkyl the term also includes saturated cycloalkyls in which 1 or 2 carbon atoms are replaced by a heteroatom, e.g. S, N or O. The term cycloalkyl includes however in particular also singly or multiply, preferably singly, unsaturated cycloalkyls without a heteroatom in the ring, provided that the cycloalkyl does not form an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

In connection with alkyl and cycloalkyl the term substituted within the context of the present invention—unless specifically defined otherwise—is understood to denote the substitution of at least one (optionally also several) hydrogen atom(s) by F, Cl, Br, I, $NH_2$, SH or OH, wherein "multiply substituted" and "substituted" in the case of multiple substitution is understood to mean that the substitution takes place multiply with the same or different substituents on different atoms as well as on the same atoms, for example triply on the same C atom as in the case of $CF_3$ or at different sites as in the case of —CH(OH)—CH=CH—$CHCl_2$. Particularly preferred substituents in this case are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular by methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is understood to denote —$CH_2$—$CH_2$—$CH_2$—$CH_2$— and —$CH_2$—$CH_2$—$CH_2$—$CH_2$—$CH_2$—, etc.

An aryl radical is understood to denote ring systems with at least one aromatic ring but without heteroatoms in also only one of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

A heteroaryl radical is understood to denote heterocyclic ring systems with at least one unsaturated ring, which contain one or more heteroatoms from the group comprising nitrogen, oxygen and/or sulfur, and may also be singly or multiply substituted. By way of example there may be mentioned from the group comprising heteroaryls; furan, benzofuran, thiophene, benzothiophene, pyrrole, pyridine, pyrimidine, pyrazine, quinoline, isoquinoline, phthalazine, benzo-[1,2,5]thiodiazole, benzothiazole, indole, benzotriazole, benzodioxolane, benzodioxan, carbazole, indole and quinazoline.

In connection with aryl and heteroaryl the term substituted is understood to denote the substitution of the aryl or heteroaryl with $R^{22}$, $OR^{22}$, a halogen, preferably F and/or Cl, a $CF_3$, a CN, an $NO_2$, an $NR^{23}R^{24}$, a $C_{1-6}$-alkyl, (saturated), a $C_{1-6}$-alkoxy, a $C_{3-8}$-cycloalkoxy, a $C_{3-8}$-cycloalkyl or a $C_{2-6}$-alkylene.

In this connection the radical $R^{22}$ denotes H, a $C_{1-10}$-alkyl radical, preferably a $C_{1-6}$-alkyl radical, an aryl or heteroaryl radical or an aryl or heteroaryl radical bonded via $C_{1-3}$-alkyl, saturated or unsaturated, in which these aryl and heteroaryl radicals must not themselves be substituted with aryl or heteroaryl radicals, the radicals $R^{23}$ and $R^{24}$, which are identical or different, denote H, a $C_{1-10}$-alkyl radical, preferably a $C_{1-6}$-alkyl radical, an aryl or heteroaryl radical, or an aryl or heteroaryl radical bonded via $C_{1-3}$-alkyl, saturated or unsaturated, in which these aryl and heteroaryl radicals must not themselves be substituted by aryl or heteroaryl radicals, or the radicals $R^{23}$ and $R^{24}$ together denote $CH_2CH_2OCH_2CH_2$, $CH_2CH_2NR^{25}CH_2CH_2$ or $(CH_2)_{3-6}$, and the radical $R^{25}$ denotes H, a $C_{1-10}$-alkyl radical, preferably a $C_{1-6}$-alkyl radical, an aryl or heteroaryl radical, or an aryl or heteroaryl radical bonded via $C_{1-3}$-alkyl, saturated or unsaturated, in which these aryl and heteroaryl radicals must not themselves be substituted by aryl or heteroaryl radicals.

The term salt is understood to denote any form of the active constituent according to the invention in which this adopts an ionic form or is charged and is coupled to a counterion (a cation or anion) or exists in solution. The term is also understood to include complexes of the active constituent with other molecules and ions, in particular complexes that are complexed via ionic interactions. In particular the term is understood to include (and this is also a preferred embodiment of the present invention) physiologically compatible salts, in particular physiologically compatible salts with cations or bases and physiologically compatible salts with anions or acids or also a salt formed with a physiologically compatible acid or a physiologically compatible cation.

The term physiologically compatible salt with anions or acids is understood within the context of the present invention to denote salts of at least one of the compounds according to the invention—generally protonated, for example on the nitrogen—as cation with at least one anion, which are physiologically compatible, especially when used in humans and/or mammals. In particular the term is understood within the context of the present invention to denote the salt formed with a physiologically compatible acid, namely salts of the respective active constituent with inorganic or organic acids, that are physiologically compatible, especially when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid. The hydrochloride salt and the citrate salt are particularly preferred.

The expression "salt formed with a physiologically compatible acid" is understood within the context of the present invention to denote salts of the respective active constituent with inorganic or organic acids, that are physiologically compatible, especially when used in humans and/or mammals. The hydrochloride or citrate is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid.

The expression "physiologically compatible salt with cations or bases" is understood within the context of the present invention to denote salts of at least one of the compounds according to the invention—generally a (deprotonated) acid—as anion with at least one, preferably inorganic, cation, that are physiologically compatible, especially when used in humans and/or mammals.

Particularly preferred are the salts of alkali metals and alkaline earth metals, but also salts with $NH_4^+$, and in particular (mono) or (di) sodium, (mono) or (di) potassium, magnesium or calcium salts.

The expression "salt formed with a physiologically compatible cation" is understood within the context of the present invention to denote salts of at least one of the respective compounds as anion with at least one inorganic cation, that are physiologically compatible, especially when used in humans and/or mammals. Particularly preferred are the salts of alkali metal and alkaline earth metals, but also with $N_4^+$, and in particular (mono) or (di) sodium, (mono) or (di) potassium, magnesium or calcium salts.

In a preferred embodiment of the 4-substituted 1-aminocyclohexane derivatives according to the invention, $R^1$ and $R^2$ independently of one another denote H; $C_{1-8}$-alkyl, saturated or unsaturated, branched or unbranched, singly or multiply substituted or unsubstituted;

or the radicals $R^1$ and $R^2$ together form a ring and denote $CH_2CH_2OCH_2CH_2$, $CH_2CH_2NR^6CH_2CH_2$ or $(CH_2)_{3-6}$, in which $R^6$ denotes H; $C_{1-8}$-alkyl, saturated or unsaturated, branched or unbranched, singly or multiply substituted or unsubstituted, preferably $R^1$ and $R^2$ independently of one another denote H; $C_{1-4}$-alkyl, saturated or unsaturated, branched or unbranched, singly or multiply substituted or unsubstituted; in which $R^1$ and $R^2$ must not both be H, or the radicals $R^1$ and $R^2$ together form a ring and denote $(CH_2)_{4-5}$, in particular $R^1$ and $R^2$ independently of one another denote methyl or ethyl, or the radicals $R^1$ and $R^2$ together form a ring and denote $(CH_2)_5$.

Particularly preferred are 4-substituted 1-aminocyclohexane derivatives, wherein $R^1$ and $R^2$ independently of one another denote $CH_3$ or H, in which $R^1$ and $R^1$ do not simultaneously denote H.

Also preferred within the context of the present invention are 4-substituted 1-aminocyclohexane derivatives, wherein $R^3$ denotes $C_{3-8}$-cycloalkyl, aryl or heteroaryl, in each case unsubstituted or singly or multiply substituted; aryl, $C_{3-8}$-cycloalkyl or heteroaryl bonded via a saturated or unsaturated, unbranched, substituted or unsubstituted $C_{1-2}$-alkyl group, in each case unsubstituted or singly or multiply substituted;

preferably $R^3$ denotes cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or singly or multiply substituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group, in each case unsubstituted or singly or multiply substituted;

in particular $R^3$ denotes phenyl, furyl, thiophenyl, naphthyl, benzyl, benzofuranyl, indolyl, indanyl, benzodioxanyl, benzodioxolanyl, pyridyl, pyrimidyl or pyrazinyl or benzothiophenyl, in each case unsubstituted or singly or multiply substituted; phenyl, furyl or thiophenyl, bonded via a saturated, unbranched $C_{1-2}$-alkyl group, in each case unsubstituted or singly or multiply substituted.

Particularly preferred are 4-substituted 1-aminocyclohexane derivatives, wherein $R^3$ denotes phenyl, thiophenyl, pyridyl or benzyl, in each case substituted or unsubstituted, particularly preferably phenyl.

Also preferred are 4-substituted 1-aminocyclohexane derivatives, wherein $R^4$ and $R^5$ independently of one another denote H; or denote $(CH_2)_m R^7$ where m=0-6 and R⁷ is selected from H; $C_{3-8}$-cycloalkyl, aryl or heteroaryl, in each case unsubstituted or singly or multiply substituted.

Furthermore preferred are 4-substituted 1-aminocyclohexane derivatives, wherein

R⁷ denotes H; cyclobutyl, cyclopropyl, cyclopentyl, cyclohexyl, cycloheptyl, cyclooctyl, anthracenyl, Indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or singly or multiply substituted;

in particular

R⁷ denotes H; cyclopentyl, cyclohexyl, cycloheptyl, cyclooctyl, indolyl, naphthyl, benzofuranyl, benzothiophenyl, indanyl, acenaphthyl, phenyl, thiophenyl, furyl, pyridyl, pyrrolyl, pyrazinyl or pyrimidyl, in each case unsubstituted or singly or multiply substituted.

Most particularly preferred are 4-substituted 1-aminocyclohexane derivatives, wherein R⁷ denotes indolyl, unsubstituted or singly or multiply substituted, in which unsubstituted indolyl or indolyl substituted singly by methyl, methoxy, chorine, fluorine or $CF_3$ are especially preferred according to the invention.

Most particularly preferred are also 4-substituted 1-aminocyclohexane derivatives, wherein n is 0 or 1 and X denotes a bond, C(O), C(O)NH, $C(O)CH_2$, C(O)CH= or C(O)N-$HCH_2$ and one of the radicals R⁴ or R⁵ is H.

In addition, most particularly preferred are 4-substituted 1-aminocyclohexane derivatives from the group {4-[3-(1H-indol-3-yl)-pyrrolidine-1-yl]-1-phenylcyclohexyl}-dimethylamine; dihydrochloride (non-polar diastereoisomer)

{4-[3-(1H-indol-3-yl)-pyrrolidine-1-yl]-1-phenylcyclohexyl}-dimethylamine; dihydrochloride (diastereoisomer mixture)

{4-[4-(5-chloro-1H-indol-3-yl)-piperidine-1-yl]-1-phenylcyclohexyl}-dimethylamine; dihydrochloride (non-polar diastereoisomer)

{4-[4-(5-chloro-1H-indol-3-yl)-piperidine-1-yl]-1-phenylcyclohexyl}-dimethylamine; dihydrochloride (polar diastereoisomer)

{4-[4-(1H-indol-3-yl)-piperidine-1-yl]-1-phenylcyclohexyl}-dimethylamine; dihydrochloride (polar diastereoisomer)

{4-[4-(1H-indol-3-yl)piperidine-1-yl]-1-phenylcyclohexyl}-dimethylamine; dihydrochloride (non-polar diastereoisomer)

{4-[4-(5-methoxy-1H-indol-3-yl)-piperidine-1-yl]-1-phenylcyclohexyl}-dimethylamine; dihydrochloride (non-polar diastereoisomer)

{4-[4-(5-methoxy-1H-indol-3-yl)piperidine-1-yl]-1-phenylcyclohexyl}-dimethylamine; dihydrochloride (polar diastereoisomer)

{4-[3-(1H-indol-3-yl)-piperidine-1-yl]-1-phenylcyclohexyl}-dimethylamine; dihydrochloride (non-polar diastereoisomer)

{4-[3-(1H-indol-3-yl)piperidine-1-yl]-1-phenylcyclohexyl}-dimethylamine; dihydrochloride (polar diastereoisomer)

2-(4-dimethylamino-4-phenylcyclohexylidene)-1-[3-(1H-indol-3-yl)pyrrolidine-1-yl]ethanone; hydrochloride (diastereoisomer mixture)

{1-(4-fluorophenyl)-4-[3-(1H-indol-3-yl)pyrrolidine-1-yl] cyclohexyl}-dimethylamine; dihydrochloride (polar and non-polar diastereoisomer)

4-(5-methoxy-1H-indol-3-yl)-3,6-dihydro-2H-pyridine-1-carboxylic acid-(4-dimethylamino-4-phenylcyclohexylmethyl)-amide; citrate (polar and non-polar diastereoisomer)

4-(1H-indol-3-yl)piperidine-1-carboxylic acid-(4-dimethylamino-4-phenylcyclohexylmethyl)-amide; hemicitrate and citrate (polar and non-polar diastereoisomer)

4-(5-chloro-1H-indol-3-yl)piperidine-1-carboxylic acid-(4-dimethylamino-4-phenylcyclohexylmethyl)-amide; citrate (polar diastereoisomer) and hemicitrate (non-polar diastereoisomer)

4-(1H-indol-3-yl)-3,6-dihydro-2H-pyridine-1-carboxylic acid-(4-dimethylamino-4-phenylcyclohexylmethyl)-amide; citrate (polar and non-polar diastereoisomer)

4-(5-fluoro-1H-indol-3-yl)piperidine-1-carboxylic acid-(4-dimethylamino-4-phenylcyclohexylmethyl)-amide; hemicitrate and citrate (polar and non-polar diastereoisomer)

2-(4-dimethylamino-4-phenylcyclohexylidene)-1-[4-(1H-indol-3-yl)-3,6-dihydro-2H-pyridine-1-yl]ethanone; hydrochloride 2-(4-dimethylamino-4-phenylcyclohexylidene)-1-[4-(1H-indol-3-yl)-piperidine-1-yl]ethanone; hydrochloride 1-[4-(5-chloro-1H-indol-3-yl)piperidine-1-yl]-2-(4-dimethylamino-4-phenylcyclohexylidene)-ethanone; hydrochloride 2-(4-dimethylamino-4-phenylcyclohexylidene)-1-[4-(5-methoxy-1H-indol-3-yl)-3,6-dihydro-2H-pyridine-1-yl] ethanone; hydrochloride 4-(1H-indol-3-yl)piperidine-1-carboxylic acid-(4-dimethylamino-4-phenylcyclohexyl)-amide; hydrochloride (polar and non-polar diastereoisomer)

4-(5-chloro-1H-indol-3-yl)piperidine-1-carboxylic acid-(4-dimethylamino-4-phenylcyclohexyl)-amide; hydrochloride (non-polar diastereoisomer)

4-(5-methoxy-1H-indol-3-yl)piperidine-1-carboxylic acid-(4-dimethylamino-4-phenyl-cyclohexyl)-amide; hydrochloride (non-polar diastereoisomer)

4-(5-fluoro-1H-indol-3-yl)piperidine-1-carboxylic acid-(4-dimethylamino-4-phenylcyclohexyl)-amide; hydrochloride (polar and non-polar diastereoisomer)

3-(5-chloro-1H-indol-3-yl)piperidine-1-carboxylic acid-(4-dimethylamino-4-phenylcyclohexyl)-amide; hydrochloride (polar and non-polar diastereoisomer)

3-(5-methoxy-1H-indol-3-yl)piperidine-1-carboxylic acid-(4-dimethylamino-4-phenylcyclohexyl)-amide; hydrochloride (polar and non-polar diastereoisomer)

2-(4-dimethylamino-4-phenylcyclohexyl)-1-[3-(1H-indol3-yl)pyrrolidine-1-yl]-ethanone; hydrochloride 2-[4-dimethylamino-4-(4-fluorophenyl)cyclohexyl]-1-[3-(1H-indol-3-yl)pyrrolidine-1-yl]-ethanone; hydrochloride (polar and non-polar diastereoisomer)

3-(5-fluor-1H-indol-3-yl)piperidine-1-carboxylic acid-(4-dimethylamino-4-phenylcyclohexyl)-amide; hydrochloride (polar diastereoisomer)

4-(5-fluoro-1H-indol-3-yl)-3,6-dihydro-2H-pyridine-1-carboxylic acid-(4-dimethylamino-4-phenylcyclohexyl-methyl)-amide; citrate (polar and non-polar diastereoisomer)

4-(5-methoxy-1H-indol-3-yl)piperidine-1-carboxylic acid-(4-dimethylamino-4-phenylcyclohexylmethyl)-amide; citrate (polar and non-polar diastereoisomer)

3-(1H-indol-3-yl)piperidine-1-carboxylic acid-(4-dimethylamino-4-phenylcyclohexylmethyl)-amide; citrate (polar and non-polar diastereoisomer)

3-(5-fluoro-1H-indol-3-yl)piperidine-1-carboxylic acid-(4-dimethylamino-4-phenylcyclohexylmethyl)-amide; citrate (polar and non-polar diastereoisomer)

3-(1H-indol-3-yl)pyrrolidine-1-carboxylic acid-(4-dimethylamino-4-phenylcyclohexylmethyl)-amide; citrate (polar and non-polar diastereoisomer)

2-(4-dimethylamino-4-phenylcyclohexyl)-1-[3-(1H-indol-3-yl)piperidine-1-yl]-ethanone; hydrochloride (diastereoisomer mixture)

2-(4-dimethylamino-4-phenylcyclohexylidene)-1-[3-(1H-indol-3-yl)-piperidine-1-yl]-ethanone; hydrochloride (diastereoisomer mixture)

4-[4-(5-chloro-1H-indol-3-yl)-3,6-dihydro-2H-pyridine-1-yl]-1-phenylcyclohexyldimethylamine; dihydrochloride (diastereoisomer mixture)

{4-[4-(1H-indol-3-yl)-3,6-dihydro-2H-pyridine-1-yl]-1-phenylcyclohexyl}-dimethylamine; dihydrochloride (diastereoisomer mixture)

{4-[4-(5-methoxy-1H-indol-3-yl)-3,6-dihydro-2H-pyridine-1-yl]-1-phenylcyclohexyl}-dimethylamine; dihydrochloride (diastereoisomer mixture)

4-(5-chloro-1H-indol-3-yl)-3,6-dihydro-2H-pyridine-1-carboxylic acid-(4-dimethylaminophenylcyclohexyl-methyl)-amide; hydrochloride (polar and non-polar diastereoisomer)

2-(4-dimethylamino-4-(4-fluorophenyl)cyclohexylidene)-1-[3-(1H-indol-3-yl)pyrrolidine-1-yl]-ethanone; hydrochloride (diastereoisomer mixture)

Dimethyl-(1-phenyl-4-piperidine-1-ylcyclohexyl)amine; dihydrochloride (polar diastereoisomer)

The substances according to the invention act for example on the relevant ORL1 receptor implicated in various diseases, which means that these substances are suitable as pharmaceutical active constituent in a pharmaceutical formulation. The invention accordingly also provides pharmaceutical formulations containing at least one 4-substituted 1-aminocyclohexane derivative.

The pharmaceutical formulations according to the invention contain, in addition to at least one 4-substituted 1-aminocyclohexane derivative according to the invention, optionally also suitable additives and/or auxiliary substances, i.e. carrier materials, fillers, solvents, diluents, colourants and/or binders, and may be administered as liquid pharmaceutical formulation forms in the form of injection solutions, drops or juices, and as semi-solid pharmaceutical formulation forms in the form of granules, tablets, pellets, patches, capsules, plasters or aerosols. The choice of the auxiliary substances, etc., as well as the amounts to be used depend on whether the pharmaceutical formulation is to be administered orally, perorally, parenterally, intravenously, intraperitoneally, intradermally, intramuscularly, intranasally, buccally, rectally or topically, for example to the skin, the mucous membranes or to the eyes. For oral application suitable preparations are in the form of tablets, sugar-coated pills, capsules, granules, drops, juices and syrups, while for parenteral, topical and inhalative application suitable forms are solutions, suspensions, readily reconstitutable dry preparations as well as sprays. 4-substituted 1-aminocyclohexane derivatives according to the invention in a depôt form, in dissolved form or in a plaster, optionally with the addition of agents promoting penetration of the skin, are suitable percutaneous application preparations. Orally or percutaneously usable preparation forms can provide for the delayed release of the 4-substituted 1-aminocyclohexane derivatives according to the invention. In principle further active constituents known to the person skilled in the art may be added to the pharmaceutical formulations according to the invention.

The amount of active constituent to be administered to the patient varies depending on the patient's weight, mode of application, medical indication and the severity of the illness. Normally 0.005 to 1000 mg/kg, preferably 0.05 to 5 mg/kg of at least one 4-substituted 1-aminocyclohexane derivative according to the invention is/are administered.

For all the above forms of the pharmaceutical formulations according to the invention it is particularly preferred if the pharmaceutical formulation contains, in addition to at least one 4-substituted 1-aminocyclohexane derivative, also a further active constituent, in particular an opioid, preferably a powerful opioid, in particular morphine, or an anaesthetic, preferably hexabarbital or halothane.

In a preferred form of the pharmaceutical formulation a contained 4-substituted 1-aminocyclohexane derivative according to the invention is present as pure diastereomer and/or enantiomer, as racemate, or as a non-equimolar or equimolar mixture of the diastereomers and/or enantiomers.

As mentioned in the introduction to the prior art, the ORL1 receptor has been identified in particular in pain causation. Accordingly, 4-substituted 1-aminocyclohexane derivatives according to the invention may be used to produce a pharmaceutical formulation for treating pain, in particular acute, neuropathic or chronic pain.

The present invention therefore also provides for the use of a 4-substituted 1-aminocyclohexane derivative according to the invention for the production of a pharmaceutical formulation for treating pain, in particular acute, visceral, neuropathic or chronic pain.

The present invention therefore also provides for the use of a 4-substituted 1-aminocyclohexane derivative according to the invention for the production of a pharmaceutical formulation for treating anxiety states, stress and syndromes associated with stress, depression, epilepsy, Alzheimer's disease, senile dementia, general cognitive dysfunctions, learning and memory disorders (as a nootropic), withdrawal symptoms, alcohol and/or drug and/or pharmaceutical formulation misuse and/or dependency, sexual dysfunctions, cardiovascular conditions, hypotension, hypertension, tinnitus, pruritis, migraine, impaired hearing, lack of intestinal motility, eating disorders, anorexia, obesity, locomotor disturbances, diarrhoea, cachexia, urinary incontinence, or as a muscle relaxant, anticonvulsant or anaesthetic, or for combined administration in treatment with an opioid analgesic or with an anaesthetic, for diuresis or anti-natriuresis, anxiolysis, for modulating motor activity, for modulating neurotransmitter secretion and treating related neurodegenerative diseases, and for treating withdrawal symptoms and/or for reducing the addictive potential of opioids.

In this connection it may be preferred in one of the aforementioned uses if a 4-substituted 1-aminocyclo-hexane derivative that is used is present as pure diastereomer and/or enantiomer, as racemate, or as a non-equimolar or equimolar mixture of the diastereomers and/or enantiomers.

The present invention furthermore provides a method for treating, especially with regard to one of the aforementioned indications, a non-human mammal or human for the relief of pain, in particular chronic pain, by administering a therapeutically effective dose of a 4-substituted 1-aminocyclohexane derivative according to the invention, or a pharmaceutical formulation according to the invention.

The present invention in addition provides processes for the preparation of the 4-substituted 1-aminocyclohexane derivatives according to the invention as outlined in the following description and examples. Particularly suitable in this connection are the following processes for the preparation of 4-substituted 1-aminocyclohexane derivatives according to the invention involving the following steps, wherein $R^1, R^2, R^3, R^4, R^5$ have the meanings given for the compounds of formula I according to the invention,
and
$R^{01}$ and $R^{02}$ independently of one another denote a protective group or have the meanings given for $R^1$ and $R^2$ for the compounds according to the invention of the formula I and "Bn" denotes the benzyl protective group:

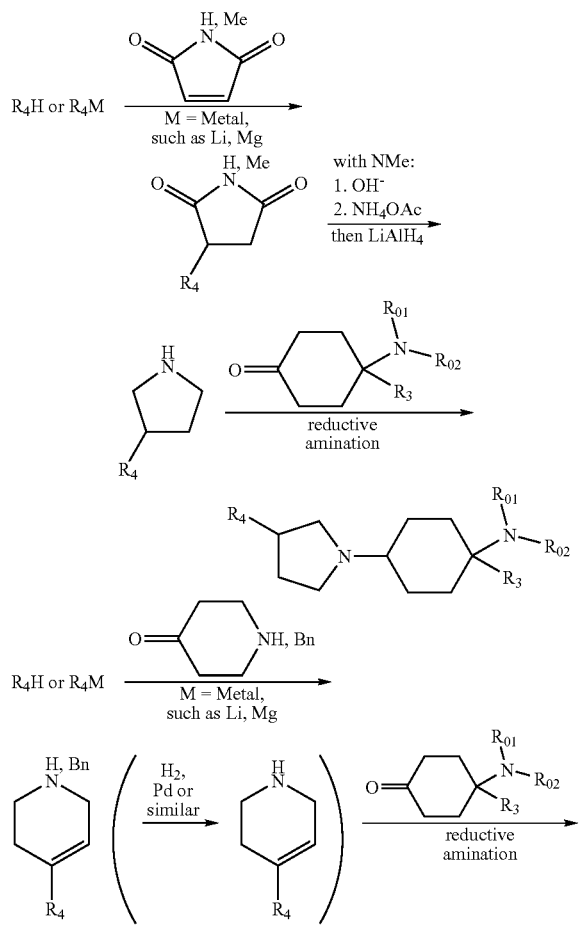

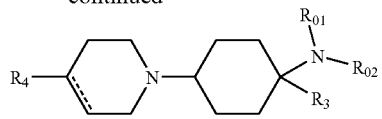
-continued 3-substituted piperidines are prepared in a similar way from 3-piperidone.

In process I for the preparation of 4-substituted 1-aminocyclohexane derivatives of the general formula I, in which n denotes 0, maleinimide or its N-methyl derivative is reacted with $R^4H$ with the addition of acid, for example acetic acid, or $R^4M$, where M denotes Li or MgX (X=Cl, Br). The product obtained is demethylated, optionally by the addition of a base, for example NaOH, followed by addition of an $NH_4^+$ source, for example $NH_4OAc$, and is then reduced with lithium aluminum hydride to the corresponding pyrrolidine derivative.

To prepare 4-substituted 1-aminocyclohexane derivatives of the general formula I in which n denotes 1,4-piperidone or 3-piperidone or the corresponding N-benzyl derivatives are reacted with $R^4H$ under the addition of acid, for example acetic acid, or with $R^4M$, where M denotes Li or Mg, and addition of acid. The tetrahydropyridine obtained is optionally reduced to the corresponding piperidine, for example with $H_2$/Pd.

The pyrrolidine or piperidine derivative that is obtained is reacted with a suitable 4-aminocyclohexanone derivative under reductive amination conditions known to the person skilled in the art, for example with hydrides such as sodium or lithium boron hydride, sodium cyano boron hydride, sodium triacetoxy boron hydride, diisobutyl aluminum hydride, lithium-tri-(sec.-butyl)boron hydride (L-Selectride®) or lithium aluminum hydride, to form the 4-substituted 1-aminocyclohexane derivatives according to the invention.

The preparation of suitable 4-aminocyclohexanones is known from the literature (Lednicer et al., J. Med. Chem., 23, 1980, 424-430; WO 0290317).

The isolation of the compounds according to the invention by column chromatography with silica gel as stationary phase and ethyl acetate, methanol, mixtures of ethyl acetate and methanol or mixtures of ethyl acetate and diethyl ether as solvent leads to a separation of the variously polar diastereoisomers. These were characterised on the basis of their development time in the separation as "most non-polar diastereoisomer" (shortest development time) up to "most polar diastereoisomer" (longest development time).

Process II

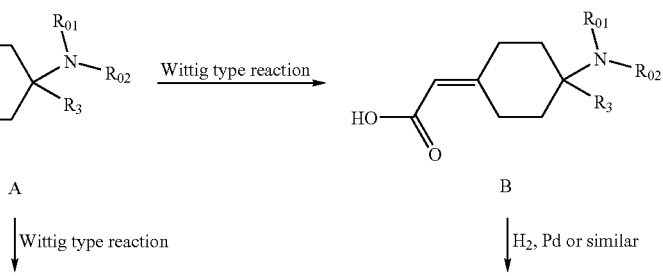

-continued

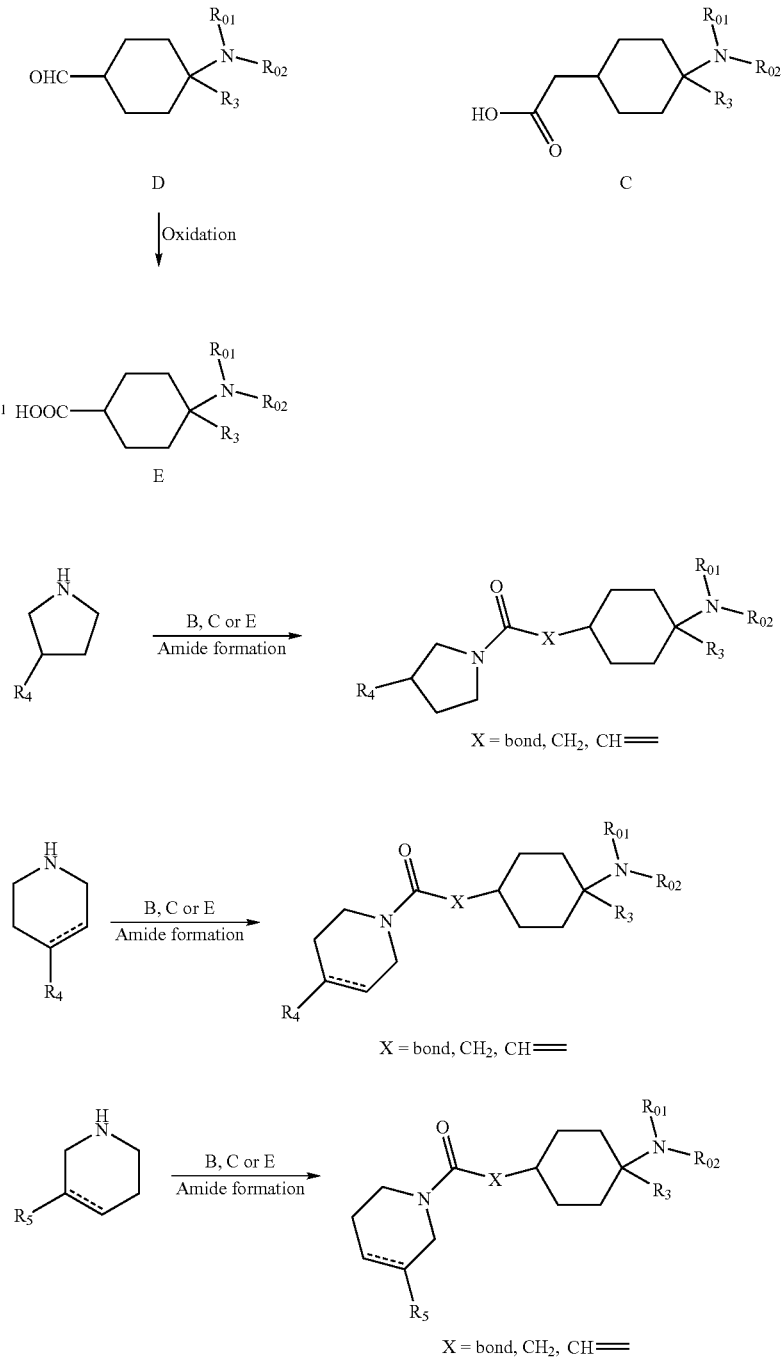

In process II for the preparation of 4-substituted 1-aminocyclohexane derivatives of the general formula I 4-aminocyclohexanone derivatives are reacted a) with methoxy triphosphonium chloride and a base, for example sodium hydride, and then with aqueous acid, for example HCl, to form the corresponding aldehydes. The corresponding carboxylic acids are obtained by adding an oxidising agent, for example potassium permanganate. b) 4-aminocyclohexanone derivatives may also be reacted with phosphonoacetic acid trimethylsilyl ester and a base, for example sodium hydride, to form cyclohexylideneacetic acid derivatives. If desired the double bond may also be hydrogenated, for example with $H_2$/Pd.

The carboxylic acid derivatives obtained in this way are reacted with the aforedescribed piperidine, pyrrolidine and tetrahydropyridine derivatives with the use of coupling reagents that are known to the person skilled in the art from peptide chemistry, or after converting the carboxylic acids into an acid chloride or an active ester, for example a 4-nitrophenyl ester or an N-hydroxysuccinimide ester.

Process III
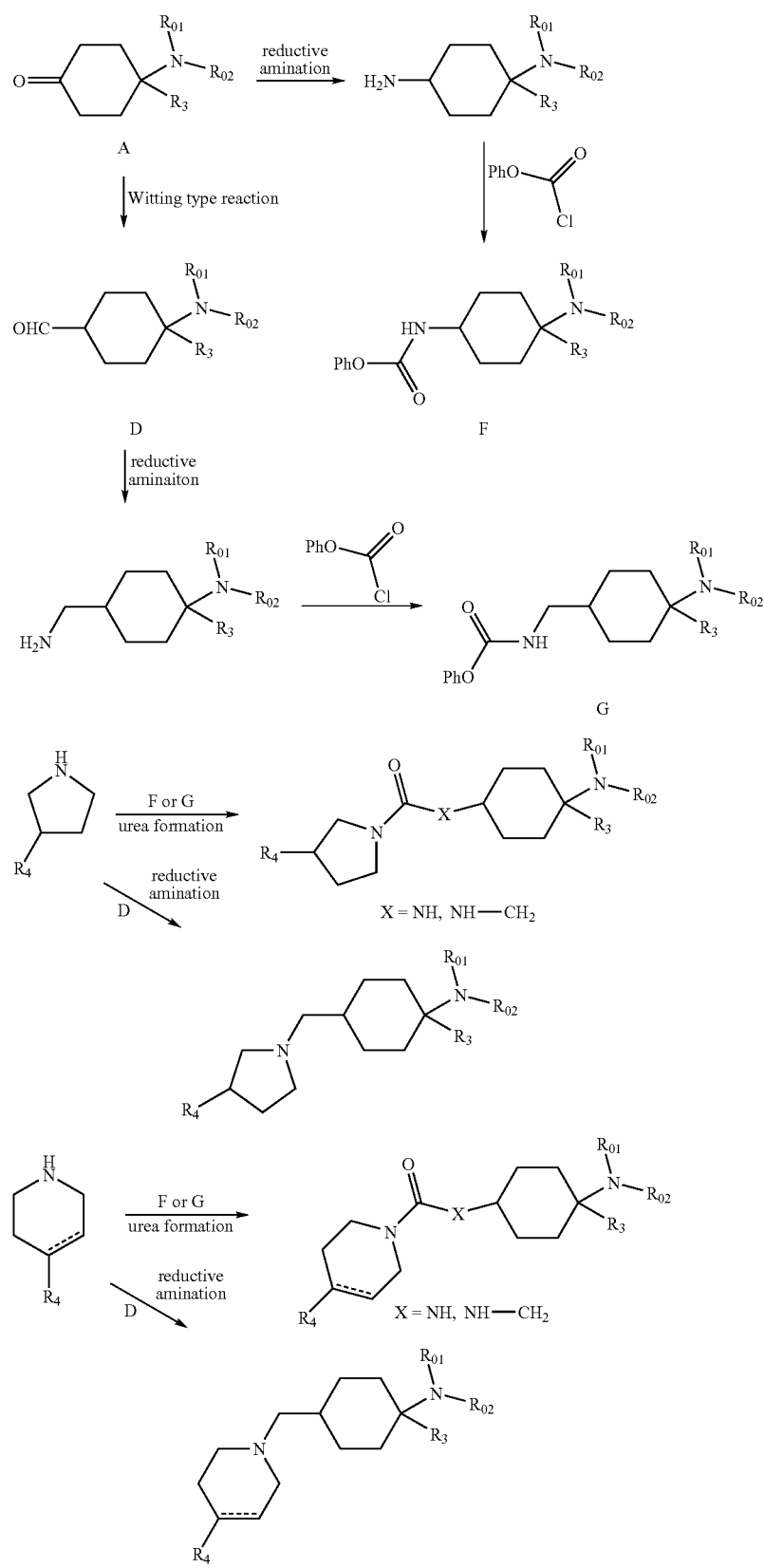

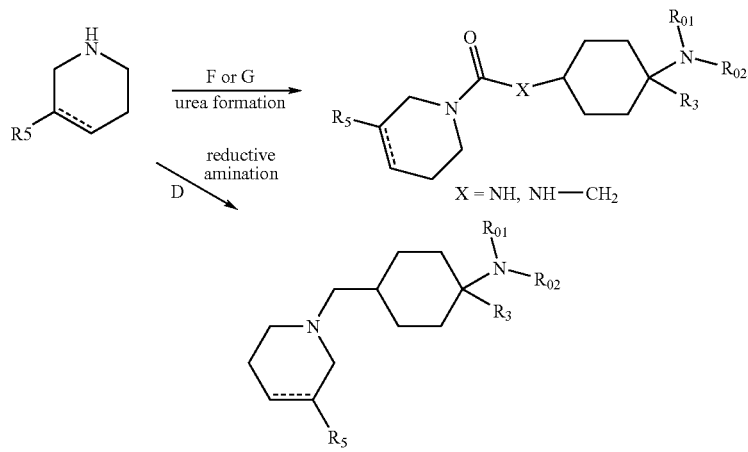

In process III 4-aminocyclohexanone derivatives or the cyclohexane carbaldehydes described in process II are reacted with hydroxylamine to form the oxime, which is then reduced to the amine with a reducing agent, for example lithium aluminum hydride. After reacting the amine with phenyl chloroformate the products are reacted with the piperidine, pyrrolidine and tetrahydropyridine derivatives described in process I at a temperature between 50° and 130° C. to form the ureas according to the invention. 4-aminocyclohexane carbaldehydes may also be reacted with piperidine, pyrrolidine and tetrahydropyridine derivatives under conditions for reductive amination known to the person skilled in the art, for example with hydrides such as sodium or lithium boron hydride, sodium cyano boron hydride, sodium triacetoxy boron hydride, diisobutyl aluminum hydride, lithium-tri-sec.-butyl)boron hydride (L-Selectride®) or lithium aluminum hydride, to form amines according to the invention.

The isolation of the compounds according to the invention by column chromatography with silica gel as stationary phase leads to a separation of the variously polar diastereoisomers. These were characterised on the basis of their development time in the separation as "most non-polar diastereoisomer" (shortest development time) up to "most polar diastereoisomer" (longest development time).

EXAMPLES

The following examples serve to illustrate the invention in more detail but do not restrict the general inventive concept.

The yields of the compounds obtained are not optimised.

All temperatures are uncorrected.

The term "ether" denotes diethyl ether, "EE" denotes ethyl acetate and "DCM" denotes dichloromethane. The term "equivalents" denotes quantitative equivalents, "m.p." denotes melting point or melting point range, "decomp." denotes decomposition, "RT" denotes room temperature, "abs." denotes absolute (anhydrous), "rac." denotes racemic, "conc." denotes concentrated, "min" denotes minutes, "h" denotes hours, "d" denotes days, "vol. %" denotes volume percent, "m %" denotes weight percent and "M" denotes concentration in mole/l.

Silica gel 60 (0.040-0.063 mm) from E. Merck, Darmstadt, was used as stationary phase for the column chromatography.

The thin-layer chromatography investigations were carried out with HPTLC precoated plates, silica gel 60 F 254, from E. Merck, Darmstadt.

The mixture ratios of solvents for chromatographic investigations are always specified in volume/volume.

The compounds used hereinafter were either commercially obtainable, or their preparation is known from the prior art or was derived from the prior art in a manner obvious to the person skilled in the art.

Example 1

{4-[3-(1H-indol-3-yl)-pyrrolidine-1-yl]-1-phenylcyclohexyl}-dimethylamine; dihydrochloride (non-polar diastereoisomer)

3-(1H-indol-3-yl)-pyrrolidine-2,5-dione

Indole (4.38 g, 40 mmole) and maleimide (7.84 g, 80 mmole) were dissolved in concentrated acetic acid (35 ml) and stirred under reflux for 36 hours. After cooling the reaction mixture water (10 ml) was slowly added dropwise. The solution was then kept for 24 hours in a refrigerator. The solid thereby formed was filtered off. 3-(1H-indol-3-yl)-pyrrolidine-2,5-dione was thereby obtained as a brown solid in a yield of 3.24 g (38%).

3-pyrrolidine-yl-1H-indole

Lithium aluminum hydrate (2.86 g, 75.6 mmole) was suspended in dry THF (50 ml) with the exclusion of atmospheric moisture. The suspension was cooled by means of an ice-salt bath to an internal temperature of ca. 0° C. 3-(1H-indol-3-yl)-pyrrolidine-2,5-dione (3.24 g, 15.12 mmole) was then added in portions within 15 minutes. After ca. 1 hour the reaction mixture had reached RT and was then boiled under reflux for 32 hours. After the reaction mixture had cooled moist THF (5 ml water in 25 ml THF) was first carefully added, followed by 5M sodium hydroxide (3 ml) and finally water (3 ml). The reaction mixture was stirred for 20 minutes and filtered through diatomaceous earth. The solvent mixture obtained after washing the filter cake several times with methanol was evaporated to dryness. The oily residue obtained was purified by column chromatography on silica gel with methanol/30% aqueous ammonia (20:1). The product was filtered again through diatomaceous earth. The solution obtained by washing the diatomaceous earth several times with chloroform was evaporated to dryness. The desired product was thereby obtained as a viscous oil in a yield of 670 mg (24%).

{4-[3-(1H-indol-3-yl)-pyrrolidine-1-yl]-1-phenyl-cyclohexyl}-dimethylamine 4-dimethylamino-4-phenylcyclohexanone (217 mg, 1 mmole) and 3-pyrrolidine-3-yl-1H-indole (186 mg, 1 mmole) were dissolved in a mixture of dry 1,2-dichloroethane (5 ml) and tetrahydrofuran (15 ml). Glacial acetic acid (57 µl, 1 mmole) and sodium sulfate (500 mg) were added to this mixture. After a reaction time of 15 minutes sodium triacetoxy boron hydride (318 mg, 1.5 mmole) was added to the reaction mixture and stirred for 4 days at RT. The reaction mixture was worked up by distilling off the solvent and adding saturated sodium hydrogen carbonate solution (20 ml) and water (20 ml). This aqueous phase was extracted with DCM (3×30 ml). The organic phase was dried with $Na_2SO_4$ and concentrated by evaporation. The chromatographic purification of the substance mixture was carried out on silica gel with methanol/30% aqueous ammonia (500:1). On dissolving the substance mixture in the solvent a colourless solid precipitated out, which was filtered off. This was identified by NMR spectroscopy as the non-polar diastereoisomer of {4-[3-(1H-indol-3-yl)-pyrrolidine-1-yl]-1-phenylcyclohexyl}-dimethylamine. The non-polar diastereoisomer was obtained in a yield of 79 mg (20%). The remaining substance mixture was purified by flash chromatography. The diastereoisomer mixture was obtained in a yield of 136 mg (35%).

{4-[3-(1H-indol-3-yl)-pyrrolidine-1-yl]-1-phenylcyclohexyl}-dimethylamine dihydrochloride (non-polar diastereoisomer)

To prepare the dihydrochloride, the non-polar diastereoisomer of {4-[3-(1H-indol-3-yl)-pyrrolidine-1-yl]-1-phenylcyclohexyl}-dimethylamine (79 mg, 0.2 mmole) was dissolved in ethyl methyl ketone (5 ml), $Me_3SiCl$ (65 µl, 0.5 mmole) was added, and the whole was stirred for 2 hours at RT. The solid formed was filtered off. The dihydrochloride of the non-polar base was thereby obtained in a yield of 77 mg (82%) as a colourless solid with an m.p. of 181°-209° C. (Example 1).

Example 2

{4-[3-(1H-indol-3-yl)-pyrrolidine-1-yl]-1-phenylcyclohexyl}-dimethylamine; dihydrochloride (diastereoisomer mixture)

To prepare the dihydrochloride of {4-[3-(1H-indol-3-yl)-pyrrolidine-1-yl]-1-phenylcyclohexyl}-dimethylamine the diastereoisomer mixture (136 mg, 0.35 mmole) was dissolved in ethyl methyl ketone (5 ml), $Me_3SiCl$ (111 µl, 0.87 mmole) was added, and the whole was stirred at RT for 1 hour. The solid formed was filtered off. The product was thereby obtained as a colourless solid with an m.p. of 182°-206° C. in a yield of 145 mg (90%).

Example 3

{4-[4-(5-chloro-1H-indol-3-yl)-piperidine-1-yl]-1-phenylcyclohexyl}-dimethylamine; dihydrochloride (non-polar diastereoisomer)

5-chloro-3-piperidine-4-yl-1H-indole 5-chloro-3-(1,2,3,6-tetrahydropyridine-4-yl)-1H-indole (2 g, 9.25 mmole) was dissolved in methanol (50 ml) under argon. Pd/carbon (100 mg, 5%) was added and the reaction mixture was hydrogenated for 8 hours at 2 bar. The product was worked up by filtering the solution through silica gel and washing with methanol (10×20 ml). The filtrate was concentrated by evaporation and dried. 5-chloro-3-piperidine-4-yl-1H-indole was obtained in a yield of 2 g (100%) with an m.p. of 156°-158° C.

{4-[4-(5-chloro-1H-indol-3-yl)-piperidine-1-yl]-1-phenylcyclohexyl}-dimethylamine 5-chloro-3-(1,2,3,6-tetrahydropyridine-4-yl)-1H-indole (218 mg, 1 mmole) and 4-dimethylamino-4-phenylcyclohexane (217 mg, 1 mmole) were dissolved in dry 1,2-dichloroethane (20 ml). Glacial acetic acid (1 mmole) and sodium triacetoxy boron hydride (300 mg, 1.4 mmole) were added to this mixture. The reaction mixture was then stirred for 24 hours at RT. The reaction mixture was worked up by distilling off the 1,2-dichloroethane and diluted with water (10 ml). The reaction mixture was adjusted to pH 11 with 5M NaOH and extracted with EE (3×20 ml). The organic phase was dried with $Na_2SO_4$ and concentrated by evaporation. The product was a mixture of two diastereoisomeric compounds, which were separated by chromatography with methanol. The non-polar diastereoisomer was obtained as a colourless oil in a yield of 210 mg (48%), and the polar diastereoisomer was obtained as a colourless oil in a yield of 80 mg (18%).

{4-[4-(5-chloro-1H-indol-3-yl)-piperidine-1-yl]-1-phenylcyclohexyl}-dimethylamine dihydrochloride To prepare the dihydrochloride the non-polar diastereoisomer of {4-[4-(5-chloro-1H-indol-3-yl)-piperidine-1-yl]-1-phenylcyclohexyl}-dimethylamine (210 mg, 0.48 mmole) was dissolved in ethyl methyl ketone (5 ml) and chlorotrimethylsilane (155 µl, 1.2 mmole) was added. The solid thereby formed was filtered off and dried. The dihydrochloride of the non-polar amine was thereby obtained (73%) as a colourless solid with an m.p. of 249°-251° C. in a yield of 180 mg (Example 3).

Example 4

{4-[4-(5-chloro-1H-indol-3-yl)-piperidine-1-yl]-1-phenylcyclohexyl}-dimethylamine; dihydrochloride (polar diastereoisomer)

To prepare the polar dihydrochloride the polar diastereoisomer of {4-[4-(5-chloro-1H-indol-3-yl)-piperidine-1-yl]-1-phenylcyclohexyl}-dimethylamine (80 mg, 0.18 mmole) was dissolved in ethyl methyl ketone (3 ml) and chlorotrimethylsilane (60 µl, 0.45 mmole) was added. The solid thereby formed was filtered off and dried. The dihydrochloride of the polar amine was thereby obtained as a colourless solid with an m.p. of 198°-200° C. in a yield of 80 mg (86%)(Example 4).

Example 5

{4-[4-(1H-indol-3-yl)-piperidine-1-yl]-1-phenylcyclohexyl}-dimethylamine; dihydrochloride (polar diastereoisomer)

3-piperidine-4-yl-1H-indole 3-(1,2,3,6-tetrahydropyridine-4-yl)-1H-indole (3 g, 16.5 mmole) was dissolved in methanol (50 ml) under argon. Pd/carbon (150 mg, 5%) was added and the reaction mixture was hydrogenated for 8 hours at 2 bar. The reaction mixture was worked up by filtering the solution through silica gel and washing with methanol (10×20 ml). The filtrate was concentrated by evaporation and dried. 3-piperidine-4-yl-1H-indole was obtained in a yield of 3.3 g (100%) with an m.p. of 190°-192° C.

{4-[4-(1H-indol-3-yl)piperidine-1-yl]-1-phenylcyclohexyl}-dimethylamine 3-piperidine-4-yl-1H-indole (200 mg, 1 mmole) and 4-dimethylamino-4-phenylcyclohexanone (217 mg, 1 mmole) were dissolved in dry 1,2-dichloroethane (20 ml). Glacial acetic acid (1 mmole) and sodium triacetoxy boron hydride (300 mg, 1.4 mmole) were added to this mixture. The reaction mixture was then stirred for 24 hours at RT. The reaction mixture was worked up by distilling off the 1,2-dichloroethane and diluting with water (10 ml). The reaction mixture was adjusted to pH 11 with 5M NaOH and extracted with EE (3×20 ml). The organic phase was dried with $Na_2SO_4$ and concentrated by evaporation. The product was a mixture of two diastereoisomeric compounds, which were separated by chromatography with methanol. The polar and the non-polar diastereoisomers were obtained in each case as a colourless oil in a yield of 90 mg (22%).

{4-[4-(1H-indol-3-yl)-piperidine-1-yl]-1-phenylcyclohexyl}-dimethylamine dihydrochloride (polar diastereoisomer)

To prepare the polar hydrochloride the polar diastereoisomer of {4-[4-(1H-indol-3-yl)-piperidine-1-yl]-1-phenylcyclohexyl}-dimethylamine (90 mg, 0.22 mmole) was dissolved in ethyl methyl ketone (3 ml) and chlorotrimethylsilane (70 µl, 0.55 mmole) was added. The solid thereby formed was filtered off and dried. The hydrochloride of the polar amine was thereby obtained as a colourless solid with an m.p. of 247°-249° C. in a yield of 106 mg (100%)(Example 5).

Example 6

{4-[4-(1H-indol-3-yl)-piperidine-1-yl]-1-phenylcyclohexyl}-dimethylamine dihydrochloride (non-polar diastereoisomer)

To prepare the non-polar dihydrochloride the non-polar diastereoisomer of {4-[4-(1H-indol-3-yl)-piperidine-1-yl]-1-phenylcyclohexyl}-dimethylamine (90 mg, 0.22 mmole) was dissolved in ethyl methyl ketone (3 ml) and chlorotrimethylsilane (70 µl, 0.55 mmole) was added. The solid thereby formed was filtered off and dried. The dihydrochloride of the non-polar amine was thereby obtained as a colourless solid with an m.p. of 263°-265° C. in a yield of 106 mg (100%) (Example 6).

Example 7

{4-[4-(5-methoxy-1H-indol-3-yl)-piperidine-1-yl]-1-phenylcyclohexyl}-dimethylamine; dihydrochloride (non-polar diastereoisomer)

5-methoxy-3-piperidine-4-yl-1H-indole 5-methoxy-3-(1,2,3,6-tedrahydropyridine-4-yl)-1H-indole (2 g, 9.44 mmole) was dissolved in methanol (50 ml) under argon. Pd/carbon (100 mg, 5%) was added and the reaction mixture was hydrogenated for 8 hours at 2 bar. The reaction mixture was worked up by filtering the solution through silica gel and washing with methanol (10×20 ml). The filtrate was concentrated by evaporation and dried. 5-methoxy-3-piperidine-4-yl-1H-indole was obtained in a yield of 1.9 g (88%) with an m.p. of 160°-162° C.

{4-[4-(5-methoxy-1H-indol-3-yl)-piperidine-1-yl]-1-phenylcyclohexyl}-dimethylamine 5-methoxy-3-piperidine-4-yl-1H-indole (461 mg, 2 mmole) and 4-dimethylamino-4-phenylcyclohexane (435 mg, 2 mmole) were dissolved in dry 1,2-dichloroethane (40 ml). Glacial acetic acid (2 mmole) and sodium triacetoxy boron hydride (600 mg, 2.8 mmole) were added to this mixture. The reaction mixture was then stirred for 24 hours at RT. The reaction mixture was worked up by distilling off the 1,2-dichloroethane and diluting with water (20 ml). The reaction mixture was adjusted to pH 11 with 5M NaOH and extracted with EE (3×20 ml). The organic phase was dried with $Na_2SO_4$ and concentrated by evaporation. The product was a mixture of two diastereoisomeric compounds, which were separated by chromatography with methanol. The non-polar diastereoisomer was obtained as a colourless oil in a yield of 590 mg (68%) and the polar diastereoisomer was obtained as a colourless oil in a yield of 170 mg (20%).

{4-[4-(5-methoxy-1H-indol-3-yl)piperidine-1-yl]-1-phenylcyclohexyl}-dimethylamine dihydrochloride To prepare the dihydrochloride the non-polar diastereoisomer of {4-[4-(5-methoxy-1H-indol-3-yl)piperidine-1-yl]-1-phenylcyclohexyl}-dimethylamine (590 mg, 1.37 mmole) was dissolved in ethyl methyl ketone (7 ml) and chlorotrimethylsilane (435 µl, 3.4 mmole) was added. The solid thereby formed was filtered off and dried. The non-polar {4-[4-(5-methoxy-1H-indol-3-yl)piperidine-1-yl]-1-phenylcyclohexyl}-dimethylamine dihydrochloride was thereby obtained as a colourless solid with an m.p. of 224°-226° C. in a yield of 690 mg (100%)(Example 7).

Example 8

{4-[4-(5-methoxy-1H-indol-3-yl)piperidine-1-yl]-1-phenylcyclohexyl}-dimethylamine dihydrochloride (polar diastereoisomer)

To prepare the dihydrochloride the polar diastereoisomer of {4-[4-(5-methoxy-1H-indol-3-yl)piperidine-1-yl]-1-phenylcyclohexyl}-dimethylamine (170 mg, 0.4 mmole) was dissolved in ethyl methyl ketone (5 ml) and chlorotrimethylsilane (125 µl, 1.0 mmole) was added. The solid thereby formed was filtered off and dried. The polar {4-[4-(5-methoxy-1H-indol-3-yl)piperidine-1-yl]-1-phenylcyclohexyl}-dimethylamine dihydrochloride was thereby obtained as a colourless solid with an m.p. of 201°-203° C. in a yield of 200 mg (Example 8).

Example 9

{4-[3-(1H-indol-3-yl)-piperidine-1-yl]-1-phenylcyclohexyl}-dimethylamine dihydrochloride (non-polar diastereoisomer)

3-(1-benzyl-1,2,5,6-tetrahydropyridine-3-yl)-1H-indole

KOH (2.12 g, 37.8 mmole), indole (1.0 g, 8.54 mmole) and 1-benzyl-3-piperidone hydrochloride (4.82 g, 21.34 mmole) were suspended in methanol (20 ml) and heated for 8 hours at 65° C. under argon. Water (40 ml) was added dropwise at RT to the mixture over a period of 40 minutes. The methanol was distilled off and the aqueous phase was extracted with EE (3×20 ml). The organic phase was dried with $Na_2SO_4$ and concentrated by evaporation. 3-(1-benzyl-1,2,5,6-tetrahydropyridine-3-yl)-1H-indole was purified by chromatography with cyclohexane/EE (1:1). The product was obtained as a yellow solid in a yield of 860 mg (35%) and an m.p. of 105°-107° C.

3-piperidine-3-yl-1H-indole 3-(1-benzyl-1,2,5,6-tetrahydropyridine-3-yl)-1H-indole (430 mg, 1.48 mmole) was dissolved in methanol (30 ml) under argon. Pd/carbon (43 mg, 10%) was added and the reaction mixture was hydrogenated for 16 hours at 2 bar. The reaction mixture was worked up by filtering the solution through silica gel and washing with methanol (10×10 ml). The filtrate was concentrated by evaporation and dried. 3-piperidine-3-yl-1H-indole was obtained as a yellow oil in a yield of 233 g (79%).

{4-[3-(1H-indol-3-yl)-piperidine-1-yl]-1-phenylcyclohexyl}-dimethylamine 3-piperidine-3-yl-1H-indole (233 mg, 1.16 mmole) and 4-dimethylamino-4-phenylcyclohexanone (253 mg, 1.16 mmole) were dissolved in dry 1,2-dichloroethane (20 ml). Glacial acetic acid (1.16 mmole) and sodium triacetoxy boron hydride (350 mg, 1.63 mmole) were added to this mixture. The mixture was then stirred for 24 hours at RT. The reaction mixture was worked up by distilling off the 1,2-dichloroethane and diluting with water (20 ml). The reaction mixture was adjusted to pH 11 with 5M NaOH and extracted with EE (3×20 ml). The organic phase was dried with $Na_2SO_4$ and concentrated by evaporation. The product was a mixture of two diastereoisomeric compounds, which were separated by chromatography with methanol. The non-polar diastereoisomer was obtained as a colourless oil in a yield of 208 mg (45%) and the polar diastereoisomer was obtained as a colourless oil in a yield of 50 mg (11%).

{4-[3-(1H-indol-3-yl)-piperidine-1-yl]-1-phenylcyclohexyl}-dimethylamine dihydrochloride (non-polar diastereoisomer)

To prepare the dihydrochloride the non-polar diastereoisomer of {4-[3-(1H-indol-3-yl)piperidine-1-yl]-1-phenylcyclohexyl}-dimethylamine (208 mg, 0.52 mmole) was dissolved in ethyl methyl ketone (5 ml) and chlorotrimethylsilane (165 µl, 1.3 mmole) was added. The solid thereby obtained was filtered off and dried. The non-polar {4-[3-(1H-indol-3-yl)piperidine-1-yl]-1-phenylcyclohexyl}-dimethylamine dihydrochloride was thereby obtained as a colourless solid with an m.p. of 188°-190° C. in a yield of 245 mg (100%) (Example 9).

Example 10

{4-[3-(1H-indol-3-yl)-piperidine-1-yl]-1-phenylcyclohexyl}-dimethylamine dihydrochloride (polar diastereoisomer)

To prepare the polar dihydrochloride the polar diastereoisomer of {4-[3-(1H-indol-3-yl)piperidine-1-yl]-1-phenylcyclohexyl}-dimethylamine (50 mg, 0.12 mmole) was dissolved in ethyl methyl ketone (3 ml) and chlorotrimethylsilane (40 µl, 0.03 mmole) was added. The solid thereby formed was filtered off and dried. The polar {4-[3-(1H-indol-3-yl)piperidine-1-yl]-1-phenylcyclohexyl}-dimethylamine dihydrochloride was thereby obtained as a colourless solid with an m.p. of 186-188° C. in a yield of 59 mg (100%) (Example 10).

Example 11

2-(4-dimethylamino-4-phenylcyclohexylidene)-1-[3-(1H-indol-3-yl)pyrrolidine-1-yl]ethanone hydrochloride 2-(4-dimethylamino-4-phenylcyclohexylidene)-1-[3-(1H-indol-3-yl)pyrrolidine-1-yl]ethanone 1-hydroxybenzotriazole (810 mg, 6.0 mmole), 3-pyrrolidine-3-yl-1H-indole (558 mg, 3.0 mmole) and N-methylmorpholine (0.666 ml, 6.0 ml) were added in succession to a solution of 4-dimethylamino-4-phenylcyclohexylidene-acetic acid (891 mg, 3.0 mmole) in dry dimethylformamide (15 ml) under argon. The solution was cooled in an ice bath and dicyclohexylcarbodiimide (1.2 g, 6.0 mmole) was added. The reaction mixture was stirred for 4 days at RT, the dicyclohexylurea precipitating out little by little. The reaction mixture was worked up by separating the precipitated urea and adding the filtrate to a mixture of saturated NaCl solution (40 ml) and saturated $NaHCO_3$ solution (10 ml). Further urea thereby precipitated out, which was separated. The aqueous phase was diluted with water (300 ml), 5M sodium hydroxide (7 ml, 35 mmole) was added, and the whole was kept for three days at 5° C. The crude product consisting of the amide precipitated out as a beige-coloured solid (994 mg). After chromatographic separation on silica gel (80 g) with EE/methanol (1:1), 2-(4-dimethylamino-4-phenylcyclohexylidene)-1-[3-(1H-indol-3-yl)pyrrolidine-1-yl]ethanone was isolated as a colourless solid with an m.p. of 94°-97° C. in a yield of 46% (585 mg). The compound was obtained as a diastereoisomer mixture.

2-(4-dimethylamino-4-phenylcyclohexylidene)-1-[3-(1H-indol-3-yl)pyrrolidine-1-yl]ethanone hydrochloride 2-(4-dimethylamino-4-phenylcyclohexylidene)-1-[3-(1H-indol-3-yl)pyrrolidine-1-yl]ethanone (200 mg, 0.47 mmole) was dissolved in ethyl methyl ketone (10 ml) and chlorotrimethylsilane (0.09 ml, 0.7 mmole) was added. After 1.5 hours the hydrochloride was obtained as a diastereoisomer mixture in the form of a colourless compound with an m.p. of 220°-223° C. in a yield of 96% (210 mg) (Example 11).

Examples 12 and 13

{1-(4-fluorophenyl)-4-[3-(1H-indol-3-yl)pyrrolidine-1-yl]cyclohexyl}-dimethylamine dihydrochloride (polar and non-polar diastereoisomer)

{1-(4-fluorophenyl)-4-[3-(1H-indol-3-yl)pyrrolidine-1-yl]cyclohexyl}-dimethylamine 4-dimethylamino-4-(4-fluorophenyl)cyclohexanone (0.701 g, 2.98 mmole) was dissolved in a mixture of 1,2-dichloroethane (20 ml) and tetrahydrofuran (15 ml) under argon, and 3-pyrrolidine-3-yl-1H-indole (0.554 g, 2.98 mmole) and acetic acid (0.164 ml, 2.98 mmole) were added. The clear pale brown solution was stirred for 15 minutes at RT and sodium triacetoxy boron hydride (0.9 g, 4.2 mmole) was then added. After stirring for 3 days at RT the reaction mixture was concentrated by evaporation and the solid colourless residue was stirred with 1M NaOH (50 ml) and EE (40 ml) for 20 minutes at RT. Some of the solid did not dissolve however, and was filtered off and washed with EE (10 ml). The non-polar diastereoisomer was thereby obtained as a colourless solid (629 mg). The phases were separated from the filtrate and the aqueous phase was extracted with EE (2×40 ml). The combined organic extracts were washed with water (20 ml), dried over sodium sulfate and concentrated by evaporation. A solid pale brown residue (0.558 g) was obtained, which was separated into the two diastereoisomers by column chromatography with methanol/30% aqueous ammonia (75:1). The non-polar diastereoisomer of {1-(4-fluorophenyl)-4-[3-(1H-indol-3-yl)pyrrolidine-1-yl]cyclohexyl}-dimethylamine was thereby obtained as a colourless solid with an m.p. of 248°-250° C. in a total yield of 0.682 g (57%) and the polar diastereoisomer was obtained pure, likewise as a colourless solid (0.331 g, 27%, m.p. 201-205° C.).

{1-(4-fluorophenyl)-4-[3-(1H-indol-3-yl)pyrrolidine-1-yl]cyclohexyl}-dimethylamine dihydrochloride The very sparingly soluble non-polar diastereoisomer of {1-(4-fluorophenyl)-4-[3-(1H-indol-3-yl)pyrrolidine-1-yl]cyclohexyl}-dimethylamine (300 mg, 0.74 mmole) was dissolved in a mixture of methanol (80 ml), ethyl methyl ketone (30 ml) and chloroform (20 ml) while heating and 5.5M isopropanolic hydrochloric acid (0.4 ml, 2.22 mmole) was added. The previously cloudy solution immediately became clear. After 2 hours it was concentrated by evaporation to ca. 5 ml. After addition of ether (10 ml) the solution was stirred overnight. After 18 hours the non-polar dihydrochloride (Example 13) was filtered off. The dihydrochloride was isolated as a colourless, crystalline substance with an m.p. of 208°-210° C. in a yield of 96% (338.8 mg).

5.5M isopropanolic hydrochloric acid (0.44 ml, 2.43 mmole) was added to a solution of the polar diastereoisomer of {1-(4-fluorophenyl)-4-[3-(1H-indol-3-yl)pyrrolidine-1-yl]cyclohexyl}-dimethylamine (330 mg, 0.81 mmole) in ethyl methyl ketone (25 ml) and methanol (5 ml). After a reaction time of 2 hours the polar dihydrochloride (Example 12) with an m.p. of 223°-230° C. was filtered off in a yield of 92% (358 mg).

Examples 14 and 15

4-(5-methoxy-1H-indol-3-yl)-3,6-dihydro-2H-pyridine-1-carboxylic acid-(4-dimethylamino-4-phenyl-cyclohexyl-methyl)-amide citrate 4-(5-methoxy-1H-indol-3-yl)-3,6-dihydro-2H-pyridine-1-carboxylic acid-(4-dimethylamino-4-phenyl-cyclohexyl-methyl)-amide (4-dimethylamino-4-phenylcyclohexyl-methyl)-carbamic acid phenyl ester (528.7 mg, 1.5 mmole) was added to a solution of 5-methoxy-3-(1,2,3,6-tetrahydropyridine-4-yl)-1H-indole (317.9 mg, 1.5 mmole) in dioxane (10 ml). The reaction mixture was then boiled for 20 hours under reflux. The reaction mixture was a suspension at RT. The solid was filtered off, washed with cold dioxane (3×1 ml) and dried. The solid was part of the polar diastereomer of 4-(5-methoxy-1H-indol-3-yl)-3,6-dihydro-2H-pyridine-1-carboxylic acid-(4-dimethylamino-4-phenylcyclohexyl-methyl)-amide (99 mg, m.p. 120°-125° C., 14%). The reaction solution (filtrate and wash phases) was concentrated by evaporation. The residue contained phenol as well as the non-polar product and the remainder of the polar product. The diastereoisomers were separated and purified by flash chromatography on silica gel (75 g). Methanol (900 ml) was used as eluent. The non-polar diastereoisomer of 4-(5-methoxy-1H-indol-3-yl)-3,6-dihydro-2H-pyridine-1-carboxylic acid-(4-dimethylamino-4-phenylcyclohexylmethyl)-amide (234 mg, m.p. 98°-104° C., 32%) and a further part of the polar diastereoisomer (120 mg, m.p. 108°-111° C., 16%) were thereby obtained in pure form.

4-(5-methoxy-1H-indol-3-yl)-3,6-dihydro-2H-pyridine-1-carboxylic acid-(4-dimethylamino-4-phenyl-cyclohexyl-methyl)-amide citrate The non-polar diastereoisomer of 4-(5-methoxy-1H-indol-3-yl)-3,6-dihydro-2H-pyridine-1-carboxylic acid-(4-dimethylamino-4-phenylcyclohexylmethyl)-amide (230 mg, 0.47 mmole) was dissolved in abs. ethanol (8 ml). Citric acid (91 mg, 0.047 mmole) dissolved in hot ethanol (1 ml) was added dropwise at RT while stirring. After stirring for 1 hour at RT only a small precipitate had formed. 25 ml of diethyl ether were added to the reaction mixture and the whole was stirred for a further ca. 1 hour at RT. The precipitate was filtered off, washed with diethyl ether (3×2 ml) and dried in vacuo. The non-polar diastereoisomer of 4-(5-methoxy-1H-indol-3-yl)-3,6-dihydro-2H-pyridine-1-carboxylic acid-(4-dimethylamino-4-phenylcyclohexyl-methyl)-amide citrate (237 mg, m.p. 142°-145° C., 74%, Example 14) was a pale yellow solid.

The polar diastereoisomer of 4-(5-methoxy-1H-indol-3-yl)-3,6-dihydro-2H-pyridine-1-carboxylic acid-(4-dimethylamino-4-phenylcyclohexyl-methyl)-amide citrate (186 mg, 0.38 mmole) was dissolved in abs. ethanol (10 ml). Citric acid (73.4 mg, 0.38 mmole) dissolved in hot ethanol (1 ml) was added dropwise at RT while stirring. A bright orange precipitate immediately formed. The precipitate was filtered off after 1 hour, washed with Et$_2$O (4×2 ml) and dried in vacuo. The polar diastereoisomer of 4-(5-methoxy-1H-indol-3-yl)-3,6-dihydro-2H-pyridine-1-carboxylic acid-(4-dimethylamino-4-phenylcyclohexyl-methyl)-amide citrate (190 mg, m.p. 110°-130° C., 73%, Example 15) was an orange solid.

Examples 16-18

4-(1H-indol-3-yl)piperidine-1-carboxylic acid-(4-dimethylamino-4-phenylcyclohexylmethyl)-amide hemicitrate (Example 16) and citrate (Examples 17 and 18)

4-(1H-indol-3-yl)piperidine-1-carboxylic acid-(4-dimethylamino-4-phenylcyclohexylmethyl)-amide The diastereoisomer mixture of (4-dimethylamino-4-phenylcyclohexylmethyl)-carbamic acid phenyl ester (599 mg, 1.7 mmole) was added to a solution of 3-piperidine-4-yl-1H-indole (340.5 mg, 1.7 mmole) in dioxane (12 ml). The reaction mixture was a clear solution above 40° C., and this solution was boiled for 24 hours under reflux. No precipitate was formed even at RT. The solvent was distilled off in vacuo. The residue contained, besides phenol, the two diastereoisomers of 4-(1H-indol-3-yl)piperidine-1-carboxylic acid-(4-dimethylamino-4-phenylcyclohexylmethyl)-amide. The diastereoisomers were separated and purified by flash chromatography on silica gel (75 g). Methanol/EE (1:1; 800 ml) and methanol (500 ml) were used as eluent. The non-polar diastereoisomer (281 mg, m.p. 89°-93° C., 36%) and the polar diastereoisomer of 4-(1H-indol-3-yl)piperidine-1-carboxylic acid-(4-dimethylamino-4-phenylcyclohexylmethyl)-amide (262 mg, m.p. 104°-107° C., 34%) were thereby obtained in pure form.

4-(1H-indol-3-yl)piperidine-1-carboxylic acid-(4-dimethylamino-4-phenylcyclohexylmethyl)-amide hemicitrate (Example 16) and citrate (Examples 17 and 18)

The non-polar diastereoisomer of 4-(1H-indol-3-yl)piperidine-1-carboxylic acid-(4-dimethylamino-4-phenylcyclohexylmethyl)-amide (280 mg, 0.61 mmole) was dissolved in abs. ethanol (16 ml) and DCM (6 ml). Citric acid (118 mg, 0.616 mmole) was added in one portion at ca. 40° C. while stirring. After 20 minutes a colourless precipitate began to form. The suspension was stirred for 24 hours at RT. Following this the precipitate was filtered off and washed with cold ethanol (2×1 ml) and diethyl ether (4×2 ml). The non-polar diastereoisomer of 4-(1H-indol-3-yl)piperidine-1-carboxylic acid-(4-dimethylamino-4-phenylcyclohexylmethyl)-amide hemicitrate (241 mg, m.p. 165°-168° C., 61%, Example 16) was obtained as a colourless solid.

The filtrate was concentrated by evaporation to 3 ml and diethyl ether (12 ml) was added in portions. The precipitate formed was filtered off, washed with diethyl ether (3×2 ml) and dried. This consisted of the non-polar diastereoisomer of 4-(1H-indol-3-yl)piperidine-1-carboxylic acid-(4-dimethylamino-4-phenylcyclohexylmethyl)-amide citrate (78 mg, m.p. 120°-128° C., 20%, Example 17) and was obtained as a greyish-white solid.

The polar diastereoisomer of 4-(1H-indol-3-yl)piperidine-1-carboxylic acid-(4-dimethylamino-4-phenylcyclohexylmethyl)-amide (262 mg, 0.57 mmole) was dissolved in abs. ethanol (7 ml) and DCM (2 ml). Citric acid (111 mg, 0.575 mmole) was added in one portion at ca. 40° C. while stirring. After stirring for several hours at RT no precipitate had formed. The solvent was distilled off in vacuo down to ca. 2 ml. A precipitate was formed by adding diethyl ether (15 ml). This was filtered off, washed with diethyl ether (3×2 ml) and dried. The cream-coloured solid was the polar diastereoisomer of 4-(1H-indol-3-yl)piperidine-1-carboxylic acid-(4-dimethylamino-4-phenylcyclohexylmethyl)-amide citrate (384 mg, 94%, Example 18).

Examples 19 and 20

4-(5-chloro-1H-indol-3-yl)piperidine-1-carboxylic acid-(4-dimethylamino-4-phenylcyclohexylmethyl)-amide citrate (polar diastereoisomer; Example 19) and hemicitrate (non-polar diastereoisomer; Example 20)

4-(5-chloro-1H-indol-3-yl)piperidine-1-carboxylic acid-(4-dimethylamino-4-phenylcyclohexylmethyl)-amide The diastereoisomer mixture of (4-dimethylamino-4-phenylcyclohexylmethyl)-carbamic acid phenyl ester (774 mg, 2.2 mmole) was added to the suspension of 5-chloro-3-piperidine-4-yl-1H-indole (516 mg, 2.2 mmole) in dioxane (20 ml). The reaction mixture was a suspension also at 100° C., and was boiled under reflux for 40 hours. To work up the suspension the existing precipitate was filtered off, washed with dioxane (1×1 ml) and diethyl ether (3×2 ml) and dried in vacuo. The isolated solid (183 mg, 17%, m.p. 140°-150° C.) was a still unpurified part of the polar diastereoisomer of 4-(5-chloro-1H-indol-3-yl)piperidine-1-carboxylic acid-(4-dimethylamino-4-phenylcyclohexylmethyl)-amide, which was purified by flash chromatography on silica gel [20 g, eluent: methanol (500 ml)]. The mother liquor and the wash phases were concentrated by evaporation in vacuo. The residue contained in addition to phenol, also the two diastereoisomers of 4-(5-chloro-1H-indol-3-yl)piperidine-1-carboxylic acid-(4-dimethylamino-4-phenylcyclohexylmethyl)-amide. The diastereoisomers were separated and purified by flash chromatography on silica gel (75 g). Methanol/EE (1:1; 900 ml) was used as eluent. The non-polar diastereoisomer (335 mg, m.p. 205°-207° C., 31%) and the polar diastereoisomer of 4-(5-chloro-1H-indol-3-yl)piperidine-1-carboxylic acid-(4-dimethylamino-4-phenylcyclohexylmethyl)-amide (115 mg, m.p. 140°-143° C., 11%) were thereby obtained as pale yellow solids.

4-(5-chloro-1H-indol-3-yl)piperidine-1-carboxylic acid-(4-dimethylamino-4-phenylcyclohexylmethyl)-amide citrate (polar diastereoisomer; Example 19) and hemicitrate (non-polar diastereoisomer; Example 20)

The non-polar diastereoisomer of 4-(5-chloro-1H-indol-3-yl)piperidine-1-carboxylic acid-(4-dimethylamino-4-phenylcyclohexylmethyl)-amide (327 mg, 0.66 mmole) was dissolved in abs. ethanol (10 ml) and DCM (4 ml). Citric acid (129 mg, 0.67 mmole) was added in one portion at ca. 40° C. while stirring. After stirring for 1 hour at RT a precipitate was formed. The suspension was stirred for 18 hours at RT. Diethyl ether (35 ml) was then added to the suspension, which was stirred for a further 2 hours. The colourless precipitate was filtered off, washed with diethyl ether (3×2 ml) and dried in vacuo. The non-polar hemicitrate of 4-(5-chloro-1H-indol-3-yl)piperidine-1-carboxylic acid-(4-dimethylamino-4-phenylcyclohexylmethyl)-amide (355 mg, m.p. 152°-156° C., 79%, Example 20) was a colourless solid.

The polar diastereoisomer of 4-(5-chloro-1H-indol-3-yl)piperidine-1-carboxylic acid-(4-dimethylamino-4-phenylcyclohexylmethyl)-amide (267 mg, 0.54 mmole) was dissolved in abs. ethanol (7 ml). Citric acid (105.1 mg, 0.55 mmole) was added in one portion at ca. 35° C. while stirring. After stirring for several hours at RT no precipitate was visible. The reaction mixture was reduced to ca. 1 ml of solution and diethyl ether (25 ml) was added in portions. The precipitate formed was filtered off after 18 hours, washed with $Et_2O$ (3×2 ml) and dried in vacuo. The polar citrate of 4-(5-chloro-1H-indol-3-yl)piperidine-1-carboxylic acid-(4-dimethylamino-4-phenylcyclohexylmethyl)-amide (324 mg, m.p. 125°-130° C., 88%, Example 19) was a colourless solid.

Examples 21 and 22

4-(1H-indol-3-yl)-3,6-dihydro-2H-pyridine-1-carboxylic acid-(4-dimethylamino-4-phenylcyclohexylmethyl)-amide citrate (4-dimethylamino-4-phenylcyclohexylmethyl)-carbamic acid 4-nitrophenyl ester As an alternative to the (4-dimethylamino-4-phenylcyclohexylmethyl)-carbamic acid phenyl ester, (4-dimethylamino-4-phenylcyclohexylmethyl)-carbamic acid 4-nitrophenyl ester could also be used for the synthesis of the ureas from the piperidine and pyrrolidine derivatives. This was prepared in a similar way from (4-aminomethyl-1-phenylcyclohexyl)-dimethylamine and chloroformic acid 4-nitrophenyl ester in DCM/pyridine.

The chloroformic acid 4-nitrophenyl ester (913.5 mg, 4.53 mmole) dissolved in abs. DCM (15 ml) was slowly added dropwise while cooling in ice water to a solution of (4-aminomethyl-1-phenylcyclohexyl)-dimethylamine (1 g, 4.3 mmole) in abs. DCM (15 ml) and pyridine (766 µl, 9.49 mmole). The reaction mixture was then stirred for 20 hours at RT. The red reaction mixture was worked up by washing with water (3×10 ml), with 1M HCl (3×10 ml) and with 1M NaOH (2×10 ml). The organic phase was dried with $Na_2SO_4$ and then concentrated by evaporation. The residue was a mixture of the diastereoisomers of (4-dimethylamino-4-phenylcyclohexylmethyl)-carbamic acid 4-nitrophenyl ester (1.25 g, reddish-brown oil, 73%).

4-(1H-indol-3-yl)-3,6-dihydro-2H-pyridine-1-carboxylic acid-(4-dimethylamino-4-phenylcyclohexylmethyl)-amide The diastereoisomer mixture of (4-dimethylamino-4-phenylcyclohexylmethyl)-carbamic acid-4-nitro-phenyl ester (825.5 mg, 2.08 mmole) was added to a solution of 3-(1,2,3,6-tetrahydropyridine-4-yl)-1H-indole (411.8 mg, 2.08 mmole) in dioxane (10 ml). The reaction mixture formed a clear, reddish-brown solution above 60° C. The solution was boiled under reflux for 12 hours. The solution was worked up by distilling off the solvent in vacuo. The residue contained, apart from nitrophenol, also the two diastereoisomers of 4-(1H-indol-3-yl)-3,6-dihydro-2H-pyridine-1-carboxylic acid-(4-dimethylamino-4-phenylcyclohexylmethyl)-amide. The diastereoisomers were separated and purified by flash chromatography on silica gel (120 g). Methanol (2000 ml) was used as eluent. The non-polar diastereoisomer (351 mg, m.p. 204°-206° C., 37%) and the polar diastereoisomer of 4-(1H-indol-3-yl)-3,6-dihydro-2H-pyridine-1-carboxylic acid-(4-dimethylamino-4-phenylcyclohexylmethyl)-amide (270 mg, m.p. 112°-115° C., 28%) were thereby obtained as pale yellow solids.

4-(1H-indol-3-yl)-3,6-dihydro-2H-pyridine-1-carboxylic acid-(4-dimethylamino-4-phenylcyclohexylmethyl)-amide citrate The non-polar diastereoisomer of 4-(1H-indol-3-yl)-3,6-dihydro-2H-pyridine-1-carboxylic acid-(4-dimethylamino-4-phenylcyclohexylmethyl)-amide (337 mg, 0.738 mmole) was dissolved in abs. ethanol (22 ml) and DCM (4 ml). Citric acid (143 mg, 0.745 mmole) was added in one portion at ca. 40° C. while stirring. After 10 minutes a pale yellow precipitate had formed. The suspension was stirred for 4 hours at RT. The amount of solvent was reduced to ca. 10 ml in vacuo. Diethyl ether (70 ml) was then added to the suspension, which was stirred for a further 2 hours. The precipitate was filtered off, washed with diethyl ether (3×3 ml) and dried in vacuo. The non-polar diastereoisomer of 4-(1H-indol-3-yl)-3,6-dihydro-2H-pyridine-1-carboxylic acid-(4-dimethylamino-4-phenylcyclohexylmethyl)-amide citrate (393 mg, m.p. 152°-155° C., 82%, Example 21) was a beige solid.

The polar diastereoisomer of 4-(1H-indol-3-yl)-3,6-dihydro-2H-pyridine-1-carboxylic acid-(4-dimethylamino-4-phenylcyclohexylmethyl)-amide (256 mg, 0.56 mmole) was dissolved in abs. ethanol (10 ml) and DCM (2 ml). Citric acid (108.8 mg, 0.57 mmole) was added in one portion at ca. 35° C. while stirring. After stirring for 4 hours at RT only brown droplets on the wall of the flask were visible. The supernatant solution was decanted and concentrated by evaporation in vacuo to ca. 5 ml. Diethyl ether (50 ml) was added in portions at RT. The precipitate formed was filtered off after 2 hours, washed with ether (2×3 ml) and dried in vacuo. The polar diastereoisomer of 4-(1H-indol-3-yl)-3,6-dihydro-2H-pyridine-1-carboxylic acid-(4-dimethylamino-4-phenylcyclohexylmethyl)-amide citrate (222 mg, m.p. 125°-130° C., 61%, Example 22) was a pale brown solid.

Examples 23 and 24

4-(5-fluoro-1H-indol-3-yl)piperidine-1-carboxylic acid-(4-dimethylamino-4-phenylcyclohexylmethyl)-amide hemicitrate (Example 23) and citrate (Example 24)

4-(5-fluoro-1H-indol-3-yl)piperidine-1-carboxylic acid-(4-dimethylamino-4-phenylcyclohexylmethyl)-amide The diastereoisomer mixture of (4-dimethylamino-4-phenylcyclohexylmethyl)-carbamic acid phenyl ester (387.7 mg, 1.1 mmole) was added to a solution of 5-fluoro-3-piperidine-4-yl-1H-indole (240.1 mg, 1.1 mmole) in dioxane (11 ml). The solution was boiled under reflux for 16 hours. The solution was worked up by distilling off the solvent in vacuo. The residue contained, apart from phenol, also the two diastereoisomers of 4-(5-fluoro-1H-indol-3-yl)piperidine-1-carboxylic acid-(4-dimethylamino-4-phenylcyclohexylmethyl)-amide. The diastereoisomers were separated and purified by flash chromatography on silica gel (25 g). Methanol/EE (1:1, 900 ml) was used as eluent. The non-polar diastereoisomer (150 mg, m.p. 95°-98° C., 29%) and the polar diastereoisomer of 4-(5-fluoro-1H-indol-3-yl)piperidine-1-carboxylic acid-(4-dimethylamino-4-phenylcyclohexylmethyl)-amide (120 mg, m.p. 206°-208° C., 23%) were thereby obtained in pure form.

4-(5-fluoro-1H-indol-3-yl)piperidine-1-carboxylic acid-(4-dimethylamino-4-phenylcyclohexylmethyl)-amide hemicitrate and citrate The non-polar diastereoisomer of 4-(5-fluoro-1H-indol-3-yl)piperidine-1-carboxylic acid-(4-dimethylamino-4-phenylcyclohexylmethyl)-amide (150 mg, 0.314 mmole) was dissolved in abs. ethanol (11 ml) and DCM (2 ml). Citric acid (61.1 mg, 0.318 mmole) was added in one portion at ca. 40° C. while stirring. After 10 minutes a colourless precipitate had formed. After stirring for 5 hours at RT the suspension was cooled overnight in a refrigerator. After 20 hours the precipitate was filtered off, washed with diethyl ether (3×3 ml) and dried in vacuo. The non-polar diastereoisomer of 4-(5-fluoro-1H-indol-3-yl)piperidine-1-carboxylic acid-(4-dimethylamino-4-phenylcyclohexylmethyl)-amide hemicitrate (117 mg, m.p. 162°-166° C., 56%, Example 23) was a colourless solid.

The polar diastereoisomer of 4-(5-fluoro-1H-indol-3-yl) piperidine-1-carboxylic acid-(4-dimethylamino-4-phenylcyclohexylmethyl)-amide (120 mg, 0.252 mmole) was dissolved in abs. ethanol (2 ml). Citric acid (48.9 mg, 0.254 mmole) was added in one portion at ca. 40° C. while stirring. The reaction mixture was stirred for 20 hours at RT. During this time no precipitate had formed. Ethanol was distilled off to dryness and the residue was dried in vacuo. The polar diastereoisomer of 4-(5-fluoro-1H-indol-3-yl)piperidine-1-carboxylic acid-(4-dimethylamino-4-phenylcyclohexylmethyl)-amide citrate (168 mg, m.p. 110°-115° C., 99%, Example 24) was a cream-coloured solid foam.

Example 25

2-(4-dimethylamino-4-phenylcyclohexylidene)-1-[4-(1H-indol-3-yl)-3,6-dihydro-2H-pyridine-1-yl]ethanone hydrochloride 2-(4-dimethylamino-4-phenylcyclohexylidene)-1-[4-(1H-indol-3-yl)-3,6-dihydro-2H-pyridine-1-yl]ethanone 1-hydroxybenzotriazole (270 mg, 2.0 mmole), 3-(1,2,3,6-tetrahydropyridine-4-yl)-1H-indole (199 mg, 1.0 mmole) and N-methylmorpholine (0.222 ml, 2.0 mmole) were added in succession under argon to a solution of (4-dimethylamino-4-phenylcyclohexylidene)-acetic acid (296 mg, 1.0 mmole) in dry dimethylformamide. The solution was cooled in an ice bath and dicyclohexylcarbodiimide (413 g, 2.0 mmole) was added. The reaction mixture was stirred for 7 days at RT, the dicyclohexylurea precipitating out little by little. The reaction mixture was worked up by separating the precipitated urea and adding the filtrate to a mixture of saturated NaCl solution (40 ml) and saturated NaHCO$_3$ solution (10 ml). Further urea precipitated out, which was separated. The aqueous phase was diluted with water (300 ml), 5M sodium hydroxide (7 ml, 35 mmole) was added, and the mixture was kept for 16 hours at 5° C. The crude product consisting of 2-(4-dimethylamino-4-phenylcyclohexylidene)-1-[4-(1H-indol-3-yl)-3,6-dihydro-2H-pyridine-1-yl]-ethanone precipitated out as a yellow solid (213 mg, 49%). After chromatographic purification on silica gel (30 g) with EE/methanol (3:1), 2-(4-dimethylamino-4-phenylcyclohexylidene)-1-[4-(1H-indol-3-yl)-3,6-dihydro-2H-pyridine-1-yl]ethanone was isolated as a yellow solid in a yield of 35% (153 mg).

2-(4-dimethylamino-4-phenylcyclohexylidene)-1-[4-(1H-indol-3-yl)-3,6-dihydro-2H-pyridine-1-yl]ethanone hydrochloride 2-(4-dimethylamino-4-phenylcyclohexylidene)-1-[4-(1H-indol-3-yl)-3,6-dihydro-2H-pyridine-1-yl]ethanone (150 mg, 0.34 mmole) was dissolved in ethyl methyl ketone (3 ml) and chlorotrimethylsilane (0.063 ml, 0.5 mmole) was added. After 1 hour the hydrochloride was isolated as a reddish-brown solid with an m.p. of 177°-182° C. in a yield of 69% (112 mg) (Example 25).

Example 26

2-(4-dimethylamino-4-phenylcyclohexylidene)-1-[4-(1H-indol-3-yl)-piperidine-1-yl]ethanone hydrochloride 2-(4-dimethylamino-4-phenylcyclohexylidene)-1-[4-(1H-indol-3-yl)-piperidine-1-yl]ethanone 1-hydroxybenzotriazole (540 mg, 4.0 mmole), 3-piperidine-4-yl)-1H-indole (400 mg, 2.0 mmole) and N-methylmorpholine (0.444 ml, 4.0 mmole) were added in succession under argon to a solution of (4-dimethylamino-4-phenylcyclohexylidene)-acetic acid (592 mg, 2.0 mmole) in dry dimethylformamide (10 ml). The solution was cooled in an ice bath and dicyclohexyldicarbodiimide (826 g, 4.0 mmole) was added. The reaction mixture was stirred for 4 days at RT, the dicyclohexylurea precipitating out little by little. The reaction mixture was worked up by separating the precipitated urea and adding the filtrate to a mixture of saturated NaCl solution (40 ml) and saturated NaHCO$_3$ solution (10 ml). Oily products thereupon precipitated out, which could not be separated by filtration. The reaction mixture was extracted with DCM (3×70 ml), the extracts were combined and the organic phase was washed with water (2×50 ml). After drying, the organic phase was concentrated by evaporation, 2-(4-dimethylamino-4-phenylcyclohexylidene)-1-[4-(1H-indol-3-yl)-piperidine-1-yl]-ethanone being obtained as a brown, oily crude product. After chromatographic separation on silica gel (70 g) with EE/methanol (2:1), 2-(4-dimethylamino-4-phenylcyclohexylidene)-1-[4-(1H-indol-3-yl)-piperidine-1-yl]-ethanone was isolated as a yellow foamy solid in a yield of 41% (359 mg).

2-(4-dimethylamino-4-phenylcyclohexylidene)-1-[4-(1H-indol-3-yl)-piperidine-1-yl]ethanone hydrochloride 2-(4-dimethylamino-4-phenylcyclohexylidene)-1-[4-(1H-indol-3-yl)-piperidine-1-yl]ethanone (344 mg, 0.779 mmole) was dissolved in ethyl methyl ketone (10 ml) and chlorotrimethylsilane (0.15 ml, 1.2 mmole) was added. After 45 minutes the hydrochloride was isolated as a beige-coloured solid with an m.p. of 178-180° C. in a yield of 65% (242 mg) (Example 26).

Example 27

1-[4-(5-chloro-1H-indol-3-yl)piperidine-1-yl]-2-(4-dimethylamino-4-phenylcyclohexylidene)-ethanone hydrochloride 1-[4-(5-chloro-1H-indol-3-yl)piperidine-1-yl]-2-(4-dimethylamino-4-phenylcyclohexylidene)-ethanone 1-hydroxybenzotriazole (405 mg, 3.0 mmole), 5-chloro-3-piperidine-4-yl-1H indole (352 mg, 1.5 mmole) and N-methylmorpholine (0.333 ml, 3.0 mmole) were added in succession under argon to a solution of (4-dimethylamino-4-phenylcyclohexylidene)-acetic acid (444 mg, 1.5 mmole) in dry dimethylformamide (10 ml). The solution was cooled in an ice bath and dicyclohexylcarbodiimide (618 mg, 3.0 mmole) was added. The reaction mixture was stirred for 7 days at RT, the dicyclohexylurea precipitating out little by little. The reaction mixture was worked up by separating the precipitated urea and adding the filtrate to a mixture of saturated NaCl solution (40 ml) and saturated NaHCO$_3$ solution (10 ml). Oily products thereupon precipitated out, which could not be separated by filtration. The reaction mixture was extracted with DCM (3×50 ml), water (300 ml) and 5M sodium hydroxide (7 ml, 35 mmole) were added to the aqueous phase, and the whole was kept for 16 hours at 5° C. 1-[4-(5-chloro-1H-indol-3-yl)piperidine-1-yl]-2-(4-dimethylamino-4-phenylcyclo-hexylidene)-ethanone thereupon precipitated out as a yellow solid (167 mg, 23%) with an m.p. of 115°-119° C.

1-[4-(5-chloro-1H-indol-3-yl)piperidine-1-yl]-2-(4-dimethylamino-4-phenylcyclohexylidene)-ethanone hydrochloride 1-[4-(5-chloro-1H-indol-3-yl)piperidine-1-yl]-2-(4-dimethylamino-4-phenylcyclohexylidene)-ethanone (167 mg, 0.35 mmole) was dissolved was dissolved in ethyl methyl ketone (5 ml) and chlorotrimethylsilane (0.067 ml, 0.53 mmole) was added. After 50 minutes the hydrochloride was isolated as a beige-coloured compound with an m.p. of 188°-190° C. in a yield of 73% (131 mg) (Example 27).

Example 28

2-(4-dimethylamino-4-phenylcyclohexylidene)-1-[4-(5-methoxy-1H-indol-3-yl)-3,6-dihydro-2H-pyridine-1-yl]-ethanone hydrochloride 2-(4-dimethylamino-4-phenylcyclohexylidene)-1-[4-(5-methoxy-1H-indol-3-yl)-3,6-dihydro-2H-pyridine-1-yl]-ethanone 1-hydroxybenzotriazole (405 mg, 3.0 mmole), 5-methoxy-3-1,2,3,6-tetrahydropyridine-4-yl)-1H-indole (345 mg, 1.5 mmole) and N-methylmorpholine (0.333 ml, 3.0 mmole) were added in succession under argon to a solution of (4-dimethylamino-4-phenylcyclohexylidene)-acetic acid (444 mg, 1.5 mmole) in dry dimethylformamide (10 ml). The solution was cooled in an ice bath and dicyclohexylcarbodiimide (618 mg, 3.0 mmole) was added. The reaction mixture was stirred for 4 days at RT, the dicyclohexylurea together with 2-(4-dimethylamino-4-phenylcyclohexylidene)-1-[4-(5-methoxy-1H-indol-3-yl)-3,6-dihydro-2H-pyridine-1-yl]-ethanone precipitating out little by little. The reaction mixture was worked up by separating the precipitated reaction products (605 mg) by filtration and the filtrate was added to a mixture of saturated NaCl solution (40 ml) and saturated NaHCO$_3$ solution (10 ml). Further urea thereupon precipitated out, which was separated. The aqueous phase was diluted with water (400 ml), 5M sodium hydroxide (7 ml, 35 mmole) was added, and the whole was kept for 16 hours at 5° C. Further 2-(4-dimethylamino-4-phenylcyclohexylidene)-1-[4-(5-methoxy-1H-indol-3-yl)-3,6-dihydro-2H-pyridine-1-yl]-ethanone thereupon precipitated out as a yellow solid crude product (283 mg).

After chromatographic separation of the mixture of 2-(4-dimethylamino-4-phenylcyclohexylidene)-1-[4-(5-methoxy-1H-indol-3-yl)-3,6-dihydro-2H-pyridine-1-yl]-ethanone and dicyclohexylurea on silica gel (40 g) with EE/methanol (4:1) and methanol, 2-(4-dimethylamino-4-phenylcyclohexylidene)-1-[4-(5-methoxy-1H-indol-3-yl)-3,6-dihydro-2H-pyridine-1-yl]-ethanone was obtained as a colourless solid with an m.p. of 215°-220° C., in a yield of 24% (172 mg). The amide fraction, which was isolated from the aqueous phase, was purified by washing with methanol (40 ml). 2-(4-dimethylamino-4-phenylcyclohexylidene)-1-[4-(5-methoxy-1H-indol-3-yl)-3,6-dihydro-2H-pyridine-1-yl]-ethanone remained as a colourless solid (120 mg, 17%).

2-(4-dimethylamino-4-phenylcyclohexylidene)-1-[4-(5-methoxy-1H-indol-3-yl)-3,6-dihydro-2H-pyridine-1-yl]-ethanone hydrochloride 2-(4-dimethylamino-4-phenylcyclohexylidene)-1-[4-(5-methoxy-1H-indol-3-yl)-3,6-dihydro-2H-pyridine-1-yl]-ethanone (252 mg, 0.536 mmole) was suspended in ethanol (20 ml) and 5M isopropanolic hydrochloric acid (0.214 ml, 1.07 mmole) was added. The hydrochloride precipitated out from the clear solution and after 1 hour was isolated as a colourless solid (222 mg, 82%) with an m.p. of 175°-178° C. (Example 28).

Examples 29 and 30

4-(1H-indol-3-yl)piperidine-1-carboxylic acid-(4-dimethylamino-4-phenylcyclohexyl)-amide hydrochloride 4-(1H-indol-3-yl)piperidine-1-carboxylic acid-(4-dimethylamino-4-phenylcyclohexyl)-amide The non-polar diastereoisomer of 4-(1H-indol-3-yl)piperidine-1-carboxylic acid-(4-dimethylamino-4-phenylcyclohexyl)-amide (338 mg, 1.0 mmole) was added to a solution of 3-piperidine-4-yl-1H-indole (200 mg, 1.0 mmole) in dioxane (10 ml). The reaction mixture was then boiled under reflux for 32 hours. The reaction mixture was worked up by distilling off dioxane and adding water (10 ml). The reaction mixture was adjusted to pH 11 with 5M NaOH and extracted with EE (3×20 ml). The organic phase was dried with Na$_2$SO$_4$ and concentrated by evaporation. The non-polar 4-(1H-indol-3-yl)piperidine-1-carboxylic acid-(4-dimethylamino-4-phenylcyclohexyl)-amide was recrystallised from methanol (5 ml). It was obtained as a colourless solid in a yield of 125 mg (28%).

The polar diastereoisomer of (4-dimethylamino-4-phenylcyclohexyl)-carbamic acid phenyl ester (316 mg, 0.93 mmole) was added to a solution of 3-piperidine-4-yl-1H-indole (187 mg, 0.93 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with Na$_2$SO$_4$ and concentrated by evaporation. The polar diastereoisomer of 4-(1H-indol-3-yl)piperidine-1-carboxylic acid-(4-dimethylamino-4-phenylcyclohexyl)-amide was recrystallised from methanol (5 ml). It was obtained as a colourless solid in a yield of 210 mg (51%).

4-(1H-indol-3-yl)piperidine-1-carboxylic acid-(4-dimethylamino-4-phenylcyclohexyl)-amide hydrochloride To prepare the non-polar diastereoisomer of 4-(1H-indol-3-yl)piperidine-1-carboxylic acid-(4-dimethylamino-4-phenylcyclohexyl)-amide hydrochloride the non-polar diastereoisomer of 4-(1H-indol-3-yl)piperidine-1-carboxylic acid-(4-dimethylamino-4-phenylcyclohexyl)-amide (125 mg, 0.28 mmole) was dissolved in ethyl methyl ketone (3 ml) and chlorotrimethylsilane (54 µl, 0.42 mmole) was added. The solid thereby formed was filtered off and dried. The hydrochloride of the non-polar amide was thereby obtained in a yield of 135 mg (100%) as a colourless solid (Example 29) with an m.p. of 210°-214° C.

To prepare the polar diastereoisomer of 4-(1H-indol-3-yl)piperidine-1-carboxylic acid-(4-dimethylamino-4-phenylcyclohexyl)-amide hydrochloride the polar 4-(1H-indol-3-yl)piperidine-1-carboxylic acid-(4-dimethylamino-4-phenylcyclohexyl)-amide (210 mg, 0.47 mmole) was dissolved in ethyl methyl ketone (5 ml) and chlorotrimethylsilane (91 µl, 0.71 mmole) was added. The solid thereby formed was filtered off and dried. The hydrochloride of the polar amide was thereby obtained in a yield of 227 mg (100%) as a colourless solid (Example 30) with an m.p. of 175°-177° C.

Example 31

4-(5-chloro-1H-indol-3-yl)piperidine-1-carboxylic acid-(4-dimethylamino-4-phenylcyclohexyl)-amide hydrochloride 4-(5-chloro-1H-indol-3-yl)piperidine-1-carboxylic acid-(4-dimethylamino-4-phenylcyclohexyl)-amide (non-polar diastereoisomer)

The non-polar diastereoisomer of (4-dimethylamino-4-phenylcyclohexyl)-carbamic acid phenyl ester (338 mg, 1.0 mmole) was added to a solution of 5-chloro-3-piperidine-4-yl-1H-indole (218 mg, 1.0 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×20 ml). The organic phase was dried with $Na_2SO_4$ and concentrated by evaporation. The non-polar diastereoisomer of 4-(5-chloro-1H-indol-3-yl)piperidine-1-carboxylic acid-(4-dimethylamino-4-phenylcyclohexyl)-amide was recrystallised from methanol (5 ml). It was obtained in a yield of 120 mg (25%) as a colourless solid.

4-(5-chloro-1H-indol-3-yl)piperidine-1-carboxylic acid-(4-dimethylamino-4-phenylcyclohexyl)-amide hydrochloride To prepare 4-(5-chloro-1H-indol-3-yl)piperidine-1-carboxylic acid-(4-dimethylamino-4-phenylcyclohexyl)-amide hydrochloride the non-polar diastereoisomer of 4-(5-chloro-1H-indol-3-yl)piperidine-1-carboxylic acid-(4-dimethylamino-4-phenylcyclohexyl)-amide (120 mg, 0.25 mmole) was dissolved in ethyl methyl ketone (3 ml) and chlorotrimethylsilane (48 µl, 0.38 mmole) was added. The solid thereby formed was filtered off and dried. The non-polar diastereoisomer of 4-(5-chloro-1H-indol-3-yl)piperidine-1-carboxylic acid-(4-dimethylamino-4-phenylcyclohexyl)-amide hydrochloride was thereby obtained in a yield of 129 mg (100%) as a colourless solid (Example 31) with an m.p. of 198°-200° C.

Example 32

4-(5-methoxy-1H-indol-3-yl)piperidine-1-carboxylic acid-(4-dimethylamino-4-phenylcyclohexyl)-amide hydrochloride 4-(5-methoxy-1H-indol-3-yl)piperidine-1-carboxylic acid-(4-dimethylamino-4-phenylcyclohexyl)-amide (non-polar diastereoisomer)

The non-polar diastereoisomer of (4-dimethylamino-4-phenylcyclohexyl)-carbamic acid phenyl ester (338 mg, 1.0 mmole) was added to a solution of 5-methoxy-3-piperidine-4-yl-1H-indole (230 mg, 1.0 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×20 ml). The organic phase was dried with $Na_2SO_4$ and concentrated by evaporation. The non-polar diastereoisomer of 4-(5-methoxy-1H-indol-3-yl)piperidine-1-carboxylic acid-(4-dimethylamino-4-phenylcyclohexyl)-amide was recrystallised from methanol (5 ml). It was obtained in a yield of 170 mg (36%) as a colourless solid.

4-(5-methoxy-1H-indol-3-yl)piperidine-1-carboxylic acid-(4-dimethylamino-4-phenylcyclohexyl)-amide hydrochloride (non-polar diastereoisomer)

To prepare the hydrochloride the non-polar diastereoisomer of 4-(5-methoxy-1H-indol-3-yl)piperidine-1-carboxylic acid-(4-dimethylamino-4-phenylcyclohexyl)-amide (170 mg, 0.36 mmole) was dissolved in ethyl methyl ketone (4 ml) and chlorotrimethylsilane (68 µl, 0.54 mmole) was added. The solid thereby formed was filtered off and dried. The hydrochloride of the non-polar diastereoisomer of 4-(5-methoxy-1H-indol-3-yl)piperidine-1-carboxylic acid-(4-dimethylamino-4-phenylcyclohexyl)-amide was thereby obtained in a yield of 183 mg (100%) as a colourless solid (Example 32) with an m.p. of 163°-165° C.

Examples 33 and 34

4-(5-fluoro-1H-indol-3-yl)piperidine-1-carboxylic acid-(4-dimethylamino-4-phenylcyclohexyl)-amide hydrochloride 4-(5-fluoro-1H-indol-3-yl)piperidine-1-carboxylic acid-(4-dimethylamino-4-phenylcyclohexyl)-amide The non-polar diastereoisomer of (4-dimethylamino-4-phenylcyclohexyl)-carbamic acid phenyl ester (322 mg, 0.95 mmole) was added to a solution of 5-fluoro-3-piperidine-4-yl-1H-indole (208 mg, 0.95 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×20 ml). The organic phase was dried with $Na_2SO_4$ and concentrated by evaporation. The non-polar diastereoisomer of 4-(5-fluoro-1H-indol-3-yl)piperidine-1-carboxylic acid-(4-dimethylamino-4-phenylcyclohexyl)-amide was recrystallised from methanol (5 ml). It was obtained in a yield of 220 mg (50%) as a colourless solid.

The polar diastereoisomer of (4-dimethylamino-4-phenylcyclohexyl)-carbamic acid phenyl ester (322 mg, 0.95 mmole) was added to a solution of 5-fluoro-3-piperidine-4- yl-1H-indole (208 mg, 0.95 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The polar diastereoisomer of 4-(5-fluoro-1H-indol-3-yl)piperidine-1-carboxylic acid-(4-dimethylamino-4-phenylcyclohexyl)-amide was recrystallised from methanol (5 ml). It was obtained in a yield of 230 mg (52%) as a colourless solid.

4-(5-fluoro-1H-indol-3-yl)piperidine-1-carboxylic acid-(4-dimethylamino-4-phenylcyclohexyl)-amide hydrochloride (Examples 33 and 34)

To prepare the hydrochloride the non-polar diastereoisomer of 4-(5-fluoro-1H-indol-3-yl)piperidine-1-carboxylic acid-(4-dimethylamino-4-phenylcyclohexyl)-amide (220 mg, 0.48 mmole) was dissolved in ethyl methyl ketone (5 ml) and chlorotrimethylsilane (92 µl, 0.71 mmole) was added. The solid thereby formed was filtered off and dried. The hydrochloride of the non-polar diastereoisomer of 4-(5-fluoro-1H-indol-3-yl)piperidine-1-carboxylic acid-(4-dimethylamino-4-phenylcyclohexyl)-amide was thereby obtained in a yield of 237 mg (100%) as a colourless solid (Example 33) with an m.p. of 167°-170° C.

To prepare the hydrochloride the polar diastereoisomer of 4-(5-fluoro-1H-indol-3-yl)piperidine-1-carboxylic acid-(4-dimethylamino-4-phenylcyclohexyl)-amide (230 mg, 0.5 mmole) was dissolved in ethyl methyl ketone (5 ml) and chlorotrimethylsilane (96 µl, 0.75 mmole) was added. The solid thereby formed was filtered off and dried. The hydrochloride of the polar diastereoisomer of 4-(5-fluoro-1H-indol-3-yl)piperidine-1-carboxylic acid-(4-dimethylamino-4-phenylcyclohexyl)-amide was thereby obtained in a yield of 248 mg (100%) as a yellow solid (Example 34) with an m.p. of 170°-172° C.

Examples 35 and 36

3-(5-chloro-1H-indol-3-yl)piperidine-1-carboxylic acid-(4-dimethylamino-4-phenylcyclohexyl)-amide hydrochloride 3-(5-chloro-1H-indol-3-yl)piperidine-1-carboxylic acid-(4-dimethylamino-4-phenylcyclohexyl)-amide The non-polar diastereoisomer of (4-dimethylamino-4-phenylcyclohexyl)-carbamic acid phenyl ester (288 mg, 0.85 mmole) was added to a solution of 5-chloro-3-piperidine-3-yl-1H-indole (200 mg, 0.85 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The non-polar diastereoisomer of 3-(5-chloro-1H-indol-3-yl)piperidine-1-carboxylic acid-(4-dimethylamino-4-phenylcyclohexyl)-amide was purified by column chromatography with methanol. It was obtained in a yield of 217 mg (53%) as a colourless solid.

The polar diastereoisomer of (4-dimethylamino-4-phenylcyclohexyl)-carbamic acid phenyl ester (288 mg, 0.85 mmole) was added to a solution of 5-chloro-3-piperidine-3-yl-1H-indole (200 mg, 0.85 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The polar diastereoisomer of 3-(5-chloro-1H-indol-3-yl)piperidine-1-carboxylic acid-(4-dimethylamino-4-phenylcyclohexyl)-amide was purified by column chromatography with methanol. It was obtained in a yield of 86 mg (21%) as a colourless solid.

3-(5-chloro-1H-indol-3-yl)piperidine-1-carboxylic acid-(4-dimethylamino-4-phenylcyclohexyl)-amide hydrochloride To prepare the hydrochloride the non-polar diastereoisomer of 3-(5-chloro-1H-indol-3-yl)piperidine-1-carboxylic acid-(4-dimethylamino-4-phenylcyclohexyl)-amide (217 mg, 0.45 mmole) was dissolved in ethyl methyl ketone (5 ml) and chlorotrimethylsilane (86 µl, 0.68 mmole) was added. The solid thereby formed was filtered off and dried. The hydrochloride of the non-polar diastereoisomer of 3-(5-chloro-1H-indol-3-yl)piperidine-1-carboxylic acid-(4-dimethylamino-4-phenylcyclohexyl)-amide was thereby obtained in a yield of 233 mg (100%) as a colourless solid (Example 35) with an m.p. of 195°-198° C.

To prepare the hydrochloride the polar diastereoisomer of 3-(5-chloro-1H-indol-3-yl)piperidine-1-carboxylic acid-(4-dimethylamino-4-phenylcyclohexyl)-amide (86 mg, 0.18 mmole) was dissolved in ethyl methyl ketone (3 ml) and chlorotrimethylsilane (34 µl, 0.27 mmole) was added. The solid thereby formed was filtered off and dried. The hydrochloride of the polar diastereoisomer of 3-(5-chloro-1H-indol-3-yl)piperidine-1-carboxylic acid-(4-dimethylamino-4-phenylcyclohexyl)-amide was thereby obtained in a yield of 92 mg (100%) as a colourless solid (Example 36) with an m.p. of 158°-160° C.

Examples 37 and 38

3-(5-methoxy-1H-indol-3-yl)piperidine-1-carboxylic acid-(4-dimethylamino-4-phenylcyclohexyl)-amide hydrochloride 3-(5-methoxy-1H-indol-3-yl)piperidine-1-carboxylic acid-(4-dimethylamino-4-phenylcyclohexyl)-amide The non-polar diastereoisomer of (4-dimethylamino-4-phenylcyclohexyl)-carbamic acid phenyl ester (330 mg, 0.98 mmole) was added to a solution of 5-methoxy-3-piperidine-3-yl-1H-indole (225 mg, 0.98 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The non-polar diastereoisomer of 3-(5-methoxy-1H-indol-3-yl)piperidine-1-carboxylic acid-(4-dimethylamino-4-phenylcyclohexyl)-amide was purified by column chromatography with methanol. It was obtained in a yield of 244 mg (53%) as a colourless solid.

The polar diastereoisomer of (4-dimethylamino-4-phenylcyclohexyl)-carbamic acid phenyl ester (330 mg, 0.98 mmole) was added to a solution of 5-methoxy-3-piperidine-3-yl-1H-indole (225 mg, 0.98 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The polar diastereoisomer of 3-(5-methoxy-1H-indol-3-yl)piperidine-1-carboxylic acid-(4-dimethylamino-4-phenylcyclohexyl)-amide was purified by column chromatography with methanol. It was obtained in a yield of 220 mg (47%) as a colourless solid.

3-(5-methoxy-1H-indol-3-yl)piperidine-1-carboxylic acid-(4-dimethylamino-4-phenylcyclohexyl)-amide hydrochloride To prepare the hydrochloride the non-polar diastereoisomer of 3-(5-methoxy-1H-indol-3-yl)piperidine-1-carboxylic acid-(4-dimethylamino-4-phenylcyclohexyl)-amide (244 mg, 0.51 mmole) was dissolved in ethyl methyl ketone (5 ml) and chlorotrimethylsilane (98 µl, 0.77 mmole) was added. The solid thereby formed was filtered off and dried. The hydrochloride of the non-polar diastereoisomer of 3-(5-methoxy-1H-indol-3-yl)piperidine-1-carboxylic acid-(4-dimethylamino-4-phenylcyclohexyl)-amide was thereby obtained in a yield of 262 mg (100%) as a colourless solid (Example 37) with an m.p. of 160°-162° C.

To prepare the hydrochloride the polar diastereoisomer of 3-(5-methoxy-1H-indol-3-yl)piperidine-1-carboxylic acid-(4-dimethylamino-4-phenylcyclohexyl)-amide (220 mg, 0.46 mmole) was dissolved in ethyl methyl ketone (5 ml) and chlorotrimethylsilane (89 µl, 0.70 mmole) was added. The solid thereby formed was filtered off and dried. The hydrochloride of the polar diastereoisomer of 3-(5-methoxy-1H-indol-3-yl)piperidine-1-carboxylic acid-(4-dimethylamino-4-phenylcyclohexyl)-amide was thereby obtained in a yield of 236 mg (100%) as a colourless solid (Example 38) with an m.p. of 175°-177° C.

Example 39

2-(4-dimethylamino-4-phenylcyclohexyl)-1-[3-(1H-indol-3-yl)pyrrolidine-1-yl]-ethanone hydrochloride 2-(4-dimethylamino-4-phenylcyclohexyl)-1-[3-(1H-indol-3-yl)pyrrolidine-1-yl]-ethanone 1-hydroxybenzotriazole (810 mg, 6.0 mmole), 3-pyrrolidine-3-yl-1H-indole (558 mg, 3.0 mmole) and N-methylmorpholine (0.666 ml, 6.0 mmole) were added in succession under argon to a solution of (4-dimethylamino-4-phenylcyclohexyl)-acetic acid (897 mg, 3.0 mmole) in dry dimethylformamide (15 ml). The solution was cooled in an ice bath and dicyclohexylcarbodiimide (1.2 g, 6.0 mmole) was added. The reaction mixture was stirred for 4 days at RT, the dicyclohexylurea precipitating out little by little. The reaction mixture was worked up by separating the precipitated urea and adding the filtrate to a mixture of saturated NaCl solution (40 ml) and saturated $NaHCO_3$ solution (10 ml). Further urea thereupon precipitated out, which was separated. The aqueous phase was diluted with water (300 ml), 5M sodium hydroxide (7 ml, 35 mmole) was added, and the reaction mixture was kept for 3 days at 5° C. The crude product of 2-(4-dimethylamino-4-phenylcyclo-hexyl)-1-[3-(1H-indol-3-yl)pyrrolidine-1-yl]-ethanone precipitated out as a beige-coloured solid (1.11 g). After chromatographic separation on silica gel (80 g) with methanol 2-(4-dimethylamino-4-phenylcyclohexyl)-1-[3-(1H-indol-3-yl)pyrrolidine-1-yl]-ethanone was isolated in a yield of 40% (521 mg) as a colourless solid with an m.p. of 98°-100° C.

2-(4-dimethylamino-4-phenylcyclohexyl)-1-[3-(1H-indol-3-yl)pyrrolidine-1-yl]-ethanone hydrochloride 2-(4-dimethylamino-4-phenylcyclohexyl)-1-[3-(1H-indol-3-yl)pyrrolidine-1-yl]-ethanone (510 mg, 1.19 mmole) was dissolved in ethyl methyl ketone (15 ml) and chlorotrimethylsilane (0.226 ml, 1.8 mmole) was added. After 1 hour the hydrochloride was isolated as a colourless compound with an m.p. of 180°-191° C. in a yield of 94% (523 mg) (Example 39).

Examples 40 and 41

2-[4-dimethylamino-4-(4-fluorophenyl)cyclohexyl]-1-[3-(1H-indol-3-yl)pyrrolidine-1-yl]-ethanone hydrochloride 2-[4-dimethylamino-4-(4-fluorophenyl)cyclohexyl]-1-[3-(1H-indol-3-yl)pyrrolidine-1-yl]-ethanone Palladium on carbon (5%, 60 mg) was added to a solution of 2-[4-dimethylamino-4-(4-fluorophenyl)cyclohexylidene]-1-[3-(1H-indol-3-yl)pyrrolidine-1-yl]-ethanone (605 mg, 1.36 mmole) in abs. methanol (100 ml). The reaction mixture was hydrogenated for 23 hours at RT under a pressure of 3 bar. The catalyst was separated using Celite and the filtrate was concentrated by evaporation. After chromatographic separation of the residue (579 mg) on silica gel (50 g) with EE/methanol (2:1) the non-polar diastereoisomer of 2-[4-dimethylamino-4-(4-fluorophenyl)cyclohexyl]-1-[3-(1H-indol-3-yl)pyrrolidine-1-yl]-ethanone was isolated in a yield of 31% (190 mg), and the polar diastereoisomer of 2-[4-dimethylamino-4-(4-fluorophenyl)cyclohexyl]-1-[3-(1H-indol-3-yl)pyrrolidine-1-yl]-ethanone was isolated in a yield of 64% (386 mg). Both compounds were colourless oils.

2-[4-dimethylamino-4-(4-fluorophenyl)cyclohexyl]-1-[3-(1H-indol-3-yl)pyrrolidine-1-yl]-ethanone hydrochloride The non-polar diastereoisomer of 2-[4-dimethylamino-4-(4-fluorophenyl)cyclohexyl]-1-[3-(1H-indol-3-yl)pyrrolidine-1-yl]-ethanone (190 mg, 0.43 mmole) was dissolved in ethyl methyl ketone (10 ml) and chlorotrimethylsilane (0.08 ml, 0.63 mmole) was added. After a reaction time of 1.5 hours the hydrochloride was obtained in a yield of 100% (208 mg) as a colourless solid with an m.p. of 168°-173° C. (Example 40).

The polar diastereoisomer of 2-[4-dimethylamino-4-(4-fluorophenyl)cyclohexyl]-1-[3-(1H-indol-3-yl)pyrrolidine-1-yl]-ethanone (329 mg, 0.73 mmole) was dissolved in ethyl methyl ketone (10 ml) and trimethylchlorosilane (0.14 ml, 1.1 mmole) was added, and the whole was stirred for 1.5 hours at RT. The precipitated hydrochloride was isolated in a yield of 93% (329 mg) and had an m.p. of 170°-177° C. (Example 41).

Example 42

3-(5-fluoro-1H-indol-3-yl)piperidine-1-carboxylic acid-(4-dimethylamino-4-phenylcyclohexyl)-amide hydrochloride (polar diastereoisomer)

3-(5-fluoro-1H-indol-3-yl)piperidine-1-carboxylic acid-(4-dimethylamino-4-phenylcyclohexyl)-amide (polar diastereoisomer)

The polar diastereoisomer of (4-dimethylamino-4-phenylcyclohexyl)-carbamic acid phenyl ester (338 mg, 1 mmole)

was added to a solution of 5-fluoro-3-piperidine-3-yl-1H-indole (218 mg, 1 mmole) in dioxane (10 ml). The reaction mixture was then boiled under reflux for 32 hours. The reaction mixture was worked up by distilling off dioxane and diluting with water (10 ml). The reaction mixture was adjusted to pH 11 with 5M NaOH and extracted with EE (3×15 ml). The organic phase was dried with $Na_2SO_4$ and concentrated by evaporation. The polar diastereoisomer of 3-(5-fluoro-1H-indol-3-yl)piperidine-1-carboxylic acid-(4-dimethylamino-4-phenylcyclohexyl)-amide was purified by column chromatography [silica gel 60 (25 g); methanol (250 ml)]. It was obtained as a colourless solid in a yield of 200 mg (43%).

3-(5-fluoro-1H-indol-3-yl)piperidine-1-carboxylic acid-(4-dimethylamino-4-phenylcyclohexyl)-amide hydrochloride (polar diastereoisomer)

To prepare the hydrochloride the polar diastereoisomer of 3-(5-fluoro-1H-indol-3-yl)piperidine-1-carboxylic acid-(4-dimethylamino-4-phenylcyclohexyl)-amide (200 mg, 0.43 mmole) was dissolved in ethyl methyl ketone (5 ml) and chlorotrimethylsilane (82 µl, 0.65 mmole) was added. The solid thereby formed was filtered off and dried. The hydrochloride of the polar diastereoisomer of 3-(5-fluoro-1H-indol-3-yl)piperidine-1-carboxylic acid-(4-dimethylamino-4-phenylcyclohexyl)-amide was thereby obtained as a colourless solid with an m.p. of 160°-164° C. in a yield of 215 mg (100%) (Example 42).

Examples 43 and 44

4-(5-fluoro-1H-indol-3-yl)-3,6-dihydro-2H-pyridine-1-carboxylic acid-(4-dimethylamino-4-phenylcyclohexyl-methyl)-amide citrate 4-(5-fluoro-1H-indol-3-yl)-3,6-dihydro-2H-pyridine-1-carboxylic acid-(4-dimethylamino-4-phenylcyclohexyl-methyl)-amide The diastereoisomer mixture of (4-dimethylamino-4-phenylcyclohexylmethyl)-carbamic acid phenyl ester (700 mg, 1.98 mmole) was added to a solution of 5-fluoro-3-(1,2,3,6-tetrahydropyridine-4-yl)-1H-indole (428.2 mg, 1.98 mmole) in dioxane (10 ml). The reaction mixture was then boiled under reflux for 12 hours. The reaction mixture was slightly cloudy at RT. The reaction mixture was worked up by distilling off the solvent. The residue contained, apart from phenol, also the two diastereoisomers of 4-(5-fluoro-1H-indol-3-yl)-3,6-dihydro-2H-pyridine-1-carboxylic acid-(4-dimethylamino-4-phenylcyclohexylmethyl)-amide. The diastereoisomers were separated and purified by flash chromatography on silica gel (50 g). Methanol/EE (1:1; 1000 ml) was used as eluent. The non-polar diastereoisomer of 4-(5-fluoro-1H-indol-3-yl)-3,6-dihydro-2H-pyridine-1-carboxylic acid-(4-dimethylamino-4-phenylcyclohexyl-methyl)-amide (300 mg, pale yellow, m.p. 105°-109° C., 32%) and the polar diastereoisomer of 4-(5-fluoro-1H-indol-3-yl)-3,6-dihydro-2H-pyridine-1-carboxylic acid-(4-dimethylamino-4-phenylcyclohexylmethyl)-amide (142 mg, 15%) were thereby obtained in pure form.

4-(5-fluoro-1H-indol-3-yl)-3,6-dihydro-2H-pyridine-1-carboxylic acid-(4-dimethylamino-4-phenylcyclohexyl-methyl)-amide citrate The non-polar diastereoisomer of 4-(5-fluoro-1H-indol-3-yl)-3,6-dihydro-2H-pyridine-1-carboxylic acid-(4-dimethylamino-4-phenylcyclohexylmethyl)-amide (288 mg, 0.606 mmole) was dissolved in abs. ethanol (6 ml) and DCM (5 ml). Citric acid (216 mg, 1.12 mmole) was added in excess at RT while stirring. After stirring overnight at RT no precipitate had formed. The solvents were distilled off. The non-polar diastereoisomer of 4-(5-fluoro-1H-indol-3-yl)-3,6-dihydro-2H-pyridine-1-carboxylic acid-(4-dimethylamino-4-phenylcyclohexylmethyl)-amide citrate (516 mg, Example 43) was an orange hygroscopic solid.

The polar diastereoisomer of 4-(5-fluoro-1H-indol-3-yl)-3,6-dihydro-2H-pyridine-1-carboxylic acid-(4-dimethylamino-4-phenylcyclohexyl-methyl)-amide (140 mg, 0.294 mmole) was dissolved in abs. ethanol (10 ml). Citric acid (105.7 mg, 0.55 mmole) was added in solid form. The mixture was stirred at 40° C. until the citric acid had completely dissolved. A sticky precipitate formed at RT on the wall of the flask. The alcohol was distilled off and the residue was dried in vacuo. The polar diastereoisomer of 4-(5-fluoro-1H-indol-3-yl)-3,6-dihydro-2H-pyridine-1-carboxylic acid-(4-dimethylamino-4-phenylcyclohexyl-methyl)-amide citrate (255 mg, hygroscopic, Example 44) was an orange-brown solid.

Example 45

4-(5-methoxy-1H-indol-3-yl)piperidine-1-carboxylic acid-(4-dimethylamino-4-phenylcyclohexylmethyl)-amide citrate 4-(5-methoxy-1H-indol-3-yl)piperidine-1-carboxylic acid-(4-dimethylamino-4-phenylcyclohexylmethyl)-amide In each case 5-methoxy-3-piperidine-4-yl-1H-indole (169.3 mg, 0.735 mmole) in dioxane (4.5 ml) and the diastereoisomer mixture of (4-dimethylamino-4-phenylcyclohexylmethyl)-carbamic acid phenyl ester (259.0 mg, 0.735 mmole) were dissolved in two microwave reaction vessels. The reaction mixture was treated with microwave radiation as follows: experiment 1 (150° C., 52 minutes) and experiment 2 (200° C., 2 minutes). In each experiment the reaction mixture was worked up by distilling off the solvent in vacuo. The respective residue contained, apart from phenol, also the two diastereomers of 4-(5-methoxy-1H-indol-3-yl)piperidine-1-carboxylic acid-(4-dimethylamino-4-phenylcyclohexylmethyl)-amide. The diastereoisomers were separated and purified by flash chromatography on silica gel (30 g and 40 g). Methanol/EE (1:1, ca. 600 ml) was used as eluent. The non-polar diastereoisomer of 4-(5-methoxy-1H-indol-3-yl)piperidine-1-carboxylic acid-(4-dimethylamino-4-phenylcyclohexylmethyl)-amide [experiment 1 (116 mg, m.p. 106°-107° C., 32%) and experiment 2 (89 mg, m.p. 110°-112° C., 25%)], and the polar diastereoisomer of 4-(5-methoxy-1H-indol-3-yl)piperidine-1-carboxylic acid-(4-dimethylamino-4-phenylcyclohexylmethyl)-amide [experiment 1 (108 mg, m.p. 98°-100° C., 30%) and experiment 2 (92 mg, m.p. 92°-97° C., 26%)] were thereby obtained in pure form.

4-(5-methoxy-1H-indol-3-yl)piperidine-1-carboxylic acid-(4-dimethylamino-4-phenylcyclohexylmethyl)-amide citrate The non-polar diastereoisomer of 4-(5-methoxy-1H-indol-3-yl)piperidine-1-carboxylic acid-(4-dimethylamino-4-phenylcyclohexylmethyl)-amide (203 mg, 0.415 mmole) was dissolved in abs. ethanol (2 ml) and DCM (3 ml). Citric acid (80.7 mg, 0.419 mmole) was added in one portion at ca. 40° C. while stirring. A colourless precipitate immediately formed at RT. After stirring for 2 hours at RT diethyl ether (25 ml) was added to the suspension and stirring was continued overnight. After 20 hours the precipitate was filtered off, washed with diethyl ether (3×1 ml) and dried in vacuo. The non-polar diastereoisomer of 4-(5-methoxy-1H-indol-3-yl) piperidine-1-carboxylic acid-(4-dimethylamino-4-phenylcyclohexylmethyl)-amide citrate (249.5 mg, m.p. 155°-158° C., 88%, Example 45) was a colourless solid.

The polar diastereoisomer of 4-(5-methoxy-1H-indol-3-yl)piperidine-1-carboxylic acid-(4-dimethylamino-4-phenylcyclohexylmethyl)-amide (197 mg, 0.403 mmole) was dissolved in abs. ethanol (3 ml) and DCM (5 ml). Citric acid (78.3 mg, 0.407 mmole) was added in one portion at ca. 40° C. while stirring. The reaction mixture was stirred for 2 hours at RT. During this time no precipitate formed. The solvents were distilled off down to a volume of 2 ml. Diethyl ether (30 ml) was added to the residue. The suspension was stirred for 20 hours at RT. The precipitate was filtered off, washed with diethyl ether (3×1.5 ml) and dried in vacuo. The polar diastereoisomer of 4-(5-methoxy-1H-indol-3-yl)piperidine-1-carboxylic acid-(4-dimethylamino-4-phenylcyclohexylmethyl)-amide citrate (239 mg, m.p. 139°-143° C., 87%, Example 46) was a colourless solid.

Examples 47 and 48

3-(1H-indol-3-yl)piperidine-1-carboxylic acid-(4-dimethylamino-4-phenylcyclohexylmethyl)-amide citrate 3-(1H-indol-3-yl)piperidine-1-carboxylic acid-(4-dimethylamino-4-phenylcyclohexylmethyl)-amide The diastereoisomer mixture of (4-dimethylamino-4-phenylcyclohexylmethyl)-carbamic acid phenyl ester (529 mg, 1.5 mmole) was added to a solution of 3-piperidine-3-yl-1H-indole (300 mg, 1.5 mmole) in dioxane (10 ml). The reaction mixture was then boiled under reflux for 20 hours. The reaction mixture was worked up by distilling off the solvent. The residue contained, in addition to phenol, also the two diastereoisomers of 3-(1H-indol-3-yl)piperidine-1-carboxylic acid-(4-dimethylamino-4-phenylcyclohexylmethyl)-amide. The diastereoisomers were separated and purified by flash chromatography on silica gel (50 g). Methanol/EE (1:1; 900 ml) was used as eluent. The non-polar diastereoisomer of 3-(1H-indol-3-yl)piperidine-1-carboxylic acid-(4-dimethylamino-4-phenylcyclohexylmethyl)-amide (220.6 mg, m.p. 165°-170° C., 32%) and the polar diastereoisomer of 3-(1H-indol-3-yl)piperidine-1-carboxylic acid-(4-dimethylamino-4-phenylcyclohexylmethyl)-amide (142 mg, m.p. 95°-99° C., 31%) were thereby obtained in pure form.

3-(1H-indol-3-yl)piperidine-1-carboxylic acid-(4-dimethylamino-4-phenylcyclohexylmethyl)-amide citrate The non-polar diastereoisomer of 3-(1H-indol-3-yl)piperidine-1-carboxylic acid-(4-dimethylamino-4-phenylcyclohexylmethyl)-amide (220 mg, 0.48 mmole) was dissolved in abs. ethanol (3 ml) and DCM (3 ml). Citric acid (93.1 mg, 0.484 mmole) was added in one portion at ca. 40° C. while stirring. Initially no precipitate formed at RT. The amount of solvent was reduced to 1 ml in vacuo and diethyl ether (20 ml) was added. After stirring for 2 hours at RT the precipitate was filtered off, washed with diethyl ether (3×1 ml) and dried in vacuo. The non-polar diastereoisomer of 3-(1H-indol-3-yl)piperidine-1-carboxylic acid-(4-dimethylamino-4-phenylcyclohexylmethyl)-amide citrate (292 mg, m.p. 150°-158° C., 93%, Example 47) was a colourless solid.

The polar diastereoisomer of 3-(1H-indol-3-yl)piperidine-1-carboxylic acid-(4-dimethylamino-4-phenylcyclohexylmethyl)-amide (214 mg, 0.467 mmole) was dissolved in abs. ethanol (3 ml). Citric acid (90.6 mg, 0.471 mmole) was added in one portion at ca. 40° C. while stirring. The reaction mixture was stirred for 2 hours at RT. During this time no precipitate formed. Ethanol was distilled off down to a volume of 1 ml. Diethyl ether (10 ml) was added to the residue. The suspension was stirred for 20 hours at RT. The precipitate was filtered off, washed with diethyl ether (3×1.5 ml) and dried in vacuo. The polar diastereoisomer of 3-(1H-indol-3-yl)piperidine-1-carboxylic acid-(4-dimethylamino-4-phenylcyclohexylmethyl)-amide citrate (297 mg, m.p. 116°-120° C., 98%, Example 48) was a cream-coloured solid.

Examples 49 and 50

3-(5-fluoro-1H-indol-3-yl)piperidine-1-carboxylic acid-(4-dimethylamino-4-phenylcyclohexylmethyl)-amide citrate 3-(5-fluoro-1H-indol-3-yl)piperidine-1-carboxylic acid-(4-dimethylamino-4-phenylcyclohexylmethyl)-amide The diastereoisomer mixture of (4-dimethylamino-4-phenylcyclohexylmethyl)-carbamic acid 4-nitrophenyl ester (400 mg, 1 mmole) was added to a solution of 5-fluoro-3-piperidine-3-yl-1H-indole (220 mg, 1 mmole) in dioxane (8 ml). The reaction mixture was then boiled under reflux for 8 hours. The reaction mixture was worked up by distilling off the solvent. The residue contained, apart from nitrophenol, also the two diastereoisomers of 3-(5-fluoro-1H-indol-3-yl) piperidine-1-carboxylic acid-(4-dimethylamino-4-phenylcyclohexylmethyl)-amide. The diastereoisomers were separated and purified by flash chromatography on silica gel (30 g). Methanol/EE (1:1; 850 ml) was used as eluent. The non-polar diastereoisomer of 3-(5-fluoro-1H-indol-3-yl)piperidine-1-carboxylic acid-(4-dimethylamino-4-phenylcyclohexylmethyl)-amide (143 mg, m.p. 110°-115° C., 30%) and the polar diastereoisomer of 3-(5-fluoro-1H-indol-3-yl)piperidine-1-carboxylic acid-(4-dimethylamino-4-phenylcyclohexylmethyl)-amide (118 mg, m.p. 98°-101° C., 25%) were thereby obtained in pure form.

3-(5-fluoro-1H-indol-3-yl)piperidine-1-carboxylic acid-(4-dimethylamino-4-phenylcyclohexylmethyl)-amide citrate The non-polar diastereoisomer of 3-(5-fluoro-1H-indol-3-yl)piperidine-1-carboxylic acid-(4-dimethylamino-4-phenylcyclohexylmethyl)-amide (140 mg, 0.294 mmole) was dissolved in abs. ethanol (2 ml). Citric acid (57.1 mg, 0.297 mmole) was added in one portion at ca. 40° C. while stirring. No precipitate formed at RT. Diethyl ether (50 ml) was slowly added to the reaction solution. The resulting suspension was stirred for 1 hour at RT. The precipitate was filtered off, washed with diethyl ether (3×2 ml) and dried in vacuo. The non-polar diastereoisomer of 3-(5-fluoro-1H-indol-3-yl)piperidine-1-carboxylic acid-(4-dimethylamino-4-phenylcyclohexylmethyl)-amide citrate (178 mg, m.p. 127°-132° C., 91%, Example 49) was a colourless solid.

The polar diastereoisomer of 3-(5-fluoro-1H-indol-3-yl) piperidine-1-carboxylic acid-(4-dimethylamino-4-phenylcyclohexylmethyl)-amide (115 mg, 0.241 mmole) was dissolved in abs. ethanol (1.5 ml). Citric acid (46.8 mg, 0.244 mmole) was added in one portion at ca. 40° C. while stirring. No precipitate formed at RT. Diethyl ether (50 ml) was slowly added to the reaction solution. The resulting suspension was stirred for 1 hour at RT. The precipitate was filtered off, washed with diethyl ether (3×2 ml) and dried in vacuo. The polar diastereoisomer of 3-(5-fluoro-1H-indol-3-yl)piperidine-1-carboxylic acid-(4-dimethylamino-4-phenylcyclohexylmethyl)-amide citrate (133 mg, m.p. 128°-130° C., 83%, Example 50) was a colourless solid.

Examples 51 and 52

3-(1H-indol-3-yl)pyrrolidine-1-carboxylic acid-(4-dimethylamino-4-phenylcyclohexylmethyl)-amide citrate 3-(1H-indol-3-yl)pyrrolidine-1-carboxylic acid-(4-dimethylamino-4-phenylcyclohexylmethyl)-amide The diastereoisomer mixture of (4-dimethylamino-4-phenylcyclohexylmethyl)-carbamic acid phenyl ester (519 mg, 1.47 mmole) was added to a solution of 3-pyrrolidine-3-yl-1H-indole (274 mg, 1.47 mmole) in dioxane (12 ml). The reaction mixture was then boiled under reflux for 12 hours. The reaction mixture was worked up by distilling off the solvent. The residue contained, apart from phenol, also the two diastereoisomers of 3-(1H-indol-3-yl)pyrrolidine-1-carboxylic acid-(4-dimethyl amino-4-phenylcyclohexylmethyl)-amide. The diastereoisomers were separated and purified by flash chromatography on silica gel (50 g). Methanol/EE (1:1; 1000 ml) was used as eluent. The non-polar diastereoisomer of 3-(1H-indol-3-yl)pyrrolidine-1-carboxylic acid-(4-dimethylamino-4-phenylcyclohexylmethyl)-amide (234 mg, m.p. 101°-103° C., 36%) and the polar diastereoisomer of 3-(1H-indol-3-yl)pyrrolidine-1-carboxylic acid-(4-dimethylamino-4-phenylcyclohexylmethyl)-amide (244 mg, m.p. 103°-106° C., 37%) were thereby obtained in pure form.

3-(1H-indol-3-yl)pyrrolidine-1-carboxylic acid-(4-dimethylamino-4-phenylcyclohexylmethyl)-amide citrate The non-polar diastereoisomer of 3-(1H-indol-3-yl)pyrrolidine-1-carboxylic acid-(4-dimethylamino-4-phenylcyclohexylmethyl)-amide (222 mg, 0.499 mmole) was dissolved in abs. ethanol (5 ml). Citric acid (96.9 mg, 0.504 mmole) was added in one portion at ca. 40° C. while stirring. No precipitate formed at RT. The amount of solvent was reduced to 2 ml in vacuo and diethyl ether (20 ml) was then added. After stirring overnight at RT the precipitate was filtered off, washed with diethyl ether (3×3 ml) and dried in vacuo. The non-polar diastereoisomer of 3-(1H-indol-3-yl)pyrrolidine-1-carboxylic acid-(4-dimethylamino-4-phenylcyclohexylmethyl)-amide citrate (292 mg, 92%, Example 51) was a pale beige solid.

The polar diastereoisomer of 3-(1H-indol-3-yl)pyrrolidine-1-carboxylic acid-(4-dimethylamino-4-phenylcyclohexyl-methyl)-amide (115 mg, 0.241 mmole) was dissolved in abs. ethanol (1.5 ml). Citric acid (46.8 mg, 0.244 mmole) was added in one portion at ca. 40° C. while stirring. No precipitate formed at RT. The amount of solvent was reduced to 2 ml in vacuo and diethyl ether (20 ml) was then added. After stirring overnight at RT the precipitate was filtered off, washed with diethyl ether (3×3 ml) and dried in vacuo. The non-polar diastereoisomer of 3-(1H-indol-3-yl)pyrrolidine-1-carboxylic acid-(4-dimethylamino-4-phenylcyclohexylmethyl)-amide citrate (312 mg, 94%, Example 52) was a pale beige solid.

Example 53

2-(4-dimethylamino-4-phenylcyclohexyl)-1-[3-(1H-indol-3-yl)piperidine-1-yl]-ethanone hydrochloride 2-(4-dimethylamino-4-phenylcyclohexyl)-1-[3-(1H-indol-3-yl)piperidine-1-yl]-ethanone Palladium on carbon (5%, 60 mg) was added to a solution of 2-(4-dimethylamino-4-phenylcyclohexylidene)-1-[3-(1H-indol-3-yl)piperidine-1-yl]-ethanone (220 mg, 0.498 mmole) in abs. methanol (30 ml). The reaction mixture was hydrogenated for 24 hours at RT under a pressure of 3 bar. The catalyst was separated using Celite and the filtrate was concentrated by evaporation. After chromatographic separation of the residue (210 mg) on silica gel (20 g) with EE/methanol (2:1), 2-(4-dimethylamino-4-phenylcyclohexyl)-1-[3-(1H-indol-3-yl)piperidine-1-yl]-ethanone was isolated as a colourless oil in a yield of 30% (66 mg). The compound was obtained as a diastereoisomer mixture.

2-(4-dimethylamino-4-phenylcyclohexyl)-1-[3-(1H-indol-3-yl)piperidine-1-yl]-ethanone hydrochloride 2-(4-dimethylamino-4-phenylcyclohexyl)-1-[3-(1H-indol-3-yl)piperidine-1-yl]-ethanone (66 mg, 0.148 mmole) was dissolved in ethyl methyl ketone (4 ml) and chlorotrimethylsilane (0.03 ml, 0.23 mmole) was added. After 1 hour the hydrochloride was isolated as a colourless solid in a yield of 65% (46 mg) (Example 53). A melting point could not be determined. The hydrochloride was obtained as a diastereoisomer mixture.

Example 54

2-(4-dimethylamino-4-phenylcyclohexylidene)-1-[3-(1H-indol-3-yl)-piperidine-1-yl]-ethanone hydrochloride 2-(4-dimethylamino-4-phenylcyclohexylidene)-1-[3-(1H-indol-3-yl)-piperidine-1-yl]-ethanone 1-hydroxybenzotriazole (675 mg, 5.0 mmole), 3-piperidine-3-yl-1H-indole (500 mg, 2.5 mmole) and N-methylmorpholine (0.555 ml, 5.0 mmole) were added in succession under argon to a solution of (4-dimethylamino-4-phenylcyclohexylidene)-acetic acid (739 mg, 2.5 mmole) in dry dimethylformamide (10 ml). The solution was cooled in an ice bath and dicyclohexylcarbodiimide (1.03 g, 5.0 mmole) was added. The reaction mixture was stirred for 5 days at RT, the dicyclohexylurea precipitating out little by little. The reaction mixture was worked up by separating the precipitated urea and adding the filtrate to a mixture of saturated NaCl solution (40 ml) and saturated NaHCO$_3$ solution (10 ml). Further urea together with 2-(4-dimethylamino-4-phenylcyclohexylidene)-1-[3-(1H-indol-3-yl)-piperidine-1-yl]-ethanone thereupon precipitated out (1.5 g). The aqueous phase was diluted with water (300 ml), 5M sodium hydroxide (7 ml, 35 mmole) was added, and the whole was kept for 16 hours at 5° C. The crude product thereupon precipitated out as a colourless solid (464 mg). The crude product of 2-(4-dimethylamino-4-phenylcyclohexylidene)-1-[3-(1H-indol-3-yl)-piperidine-1-yl]-ethanone was purified chromatographically on silica gel (60 g) with EE/methanol (4:1) and (2:1) and obtained in a yield of 30% (322 mg)—2-(4-dimethylamino-4-phenylcyclohexylidene)-1-[3-(1H-indol-3-yl)-piperidine-1-yl]-ethanone was obtained as a diastereoisomer mixture. A separation was not possible.

2-(4-dimethylamino-4-phenylcyclohexylidene)-1-[3-(1H-indol-3-yl)-piperidine-1-yl]-ethanone hydrochloride 2-(4-dimethylamino-4-phenylcyclohexylidene)-1-[3-(1H-indol-3-yl)-piperidine-1-yl]-ethanone (316 mg, 0.716 mmole) was dissolved in ethyl methyl ketone (4 ml) and chlorotrimethylsilane (0.14 ml, 1.1 mmole) was added. After 1.5 hours the 2-(4-dimethylamino-4-phenylcyclohexylidene)-1-[3-(1H-indol-3-yl)-piperidine-1-yl]-ethanone hydrochloride was obtained as a diastereoisomer mixture in the form of a colourless compound with an m.p. of 177°-180° C. in a yield of 89% (305 mg) (Example 54).

Example 55

4-[4-(5-chloro-1H-indol-3-yl)-3,6-dihydro-2H-pyridine-1-yl]-1-phenylcyclohexyldimethylamine dihydrochloride

5-chloro-3-(1,2,3,6-tetrahydropyridine-4-yl)-1H-indole

KOH (8.19 g, 146 mmole), 5-chloroindole (5.0 g, 33 mmole) and piperidine-4-one hydrochloride (10.22 g, 85.7 mmole) were suspended in methanol (50 ml) and heated for 8 hours at 65° C. under argon. Water (50 ml) was added dropwise at RT to the mixture over a period of 40 minutes. The solid thereby formed was filtered off, washed with water (3×20 ml) and recrystallised from methanol (20 ml). 5-chloro-3-(1,2,3,6-tetrahydropyridine-4-yl)-1H-indole was obtained in a yield of 6.4 g (90%) as a yellow solid with an m.p. of 166°-168° C.

4-[4-(5-chloro-1H-indol-3-yl)-3,6-dihydro-2H-pyridine-1-yl]-1-phenylcyclohexyldimethylamine 5-chloro-3-(1,2,3,6-tetrahydropyridine-4-yl)-1H-indole (170 mg, 0.79 mmole) and 4-dimethylamino-4-phenylcyclohexanone (171 mg, 0.79 mmole) were dissolved in dry 1,2-dichloro-ethane (10 ml). Glacial acetic acid (0.79 mmole) and sodium triacetoxy boron hydride (300 mg, 1.4 mmole) were added to this mixture. The reaction mixture was then stirred for 24 hours at RT. The reaction mixture was worked up by distilling off the 1,2-dichloroethane and diluting with water (10 ml). The reaction mixture was adjusted to pH 11 with 5M NaOH and extracted with EE (4×20 ml). The organic phase was dried with $Na_2SO_4$ and concentrated by evaporation. The diastereoisomer mixture was obtained as a colourless solid in a yield of 340 mg (100%).

4-[4-(5-chloro-1H-indol-3-yl)-3,6-dihydro-2H-pyridine-1-yl]-1-phenylcyclohexyldimethylamine dihydrochloride To prepare the hydrochloride the diastereoisomer mixture of 4-[4-(5-chloro-1H-indol-3-yl)-3,6-dihydro-2H-pyridine-1-yl]-1-phenylcyclohexyldimethylamine (340 mg, 0.79 mmole) was dissolved in ethyl methyl ketone (5 ml) and chlorotrimethylsilane (255 μL, 2.0 mmole) was added. The solid thereby formed was filtered off and dried. The hydrochloride was thereby obtained in a yield of 170 mg (46%) as a colourless solid (Example 55) with an m.p. of 210°-212° C.

Example 56

{4-[4-(1H-indol-3-yl)-3,6-dihydro-2H-pyridine-1-yl]-1-phenylcyclohexyl}-dimethylamine dihydrochloride

3-(1,2,3,6-tetrahydropyridine-4-yl)-1H-indole

KOH (8.19 g, 146 mmole), indole (3.87 g, 33 mmole) and piperidine-4-one hydrochloride (10.22 g, 85.7 mmole) were suspended in methanol (50 ml) and heated for 8 hours at 65° C. under argon. Water (50 ml) was added dropwise at RT to the mixture over a period of 40 minutes. The solid thereby formed was filtered off, washed with water (3×20 ml) and recrystallised from methanol (20 ml). 3-(1,2,3,6-tetrahydropyridine-4-yl)-1H-indole was obtained in a yield of 4.26 g (71%) as a yellow solid with an m.p. of 172°-174° C.

{4-[4-(1H-indol-3-yl)-3,6-dihydro-2H-pyridine-1-yl]-1-phenylcyclohexyl}-dimethylamine 3-(1,2,3,6-tetrahydropyridine-4-yl)-1H-indole (182 mg, 1 mmole) and 4-dimethylamino-4-phenylcyclohexanone (217 mg, 1 mmole) were dissolved in dry 1,2-dichloroethane (10 ml). Glacial acetic acid (1 mmole) and sodium triacetoxy boron hydride (300 mg, 1.4 mmole) were added to this mixture. The reaction mixture was then stirred for 24 hours at RT. The reaction mixture was worked up by distilling off the 1,2-dichloroethane and diluting with water (10 ml). The reaction mixture was adjusted to pH 11 with 5M NaOH and extracted with EE (4×20 ml). The organic phase was dried with $Na_2SO_4$ and concentrated by evaporation. The product was a mixture of two diastereoisomeric compounds, which could not be separated by chromatography. The diastereoisomer mixture was obtained as a colourless solid in a yield of 320 mg (80%).

{4-[4-(1H-indol-3-yl)-3,6-dihydro-2H-pyridine-1-yl]-1-phenylcyclohexyl}-dimethylamine dihydrochloride To prepare the hydrochloride the diastereoisomer mixture of {4-[4-(1H-indol-3-yl)-3,6-dihydro-2H-pyridine-1-yl]-1-phenylcyclohexyl}-dimethylamine (320 mg, 0.8 mmole) was dissolved in ethyl methyl ketone (5 ml) and chlorotrimethylsilane (255 μl, 2.0 mmole) was added. The solid thereby formed was filtered off and dried. The hydrochloride was thereby obtained in a yield of 378 mg (100%) as a colourless solid (Example 56) with an m.p. of 188°-191° C.

Example 57

{4-[4-(5-methoxy-1H-indol-3-yl)-3,6-dihydro-2H-pyridine-1-yl]-1-phenylcyclohexyl}-dimethylamine dihydrochloride

5-methoxy-3-(1,2,3,6-tetrahydropyridine-4-yl)-1H-indole

KOH (8.44 g, 150 mmole), 5-methoxyindole (5.0 g, 34 mmole) and piperidine-4-one hydrochloride (10.53 g, 88.3 mmole) were suspended in methanol (50 ml) and heated for 8 hours at 65° C. under argon. Water (50 ml) was added dropwise at RT to the mixture over a period of 40 minutes. The solid thereby formed was filtered off, washed with water (3×20 ml) and recrystallised from methanol (20 ml). 5-methoxy-3-(1,2,3,6-tetrahydropyridine-4-yl)-1H-indole was obtained in a yield of 4.66 g (75%) as a yellow solid with an m.p. of 173°-175° C.

{4-[4-(5-methoxy-1H-indol-3-yl)-3,6-dihydro-2H-pyridine-1-yl]-1-phenylcyclohexyl}-dimethylamine 5-methoxy-3-(1,2,3,6-tetrahydropyridine-4-yl)-1H-indole (212 mg, 1.0 mmole) and 4-dimethylamino-4-phenylcyclo-hexanone (217 mg, 1.0 mmole) were dissolved in dry 1,2-dichloroethane (20 ml). Glacial acetic acid (1.0 mmole) and sodium triacetoxy boron hydride (300 mg, 1.4 mmole) were added to this mixture. The reaction mixture was then stirred for 24 hours at RT. The reaction mixture was worked up by distilling off the 1,2-dichloroethane and diluting with water (10 ml). The reaction mixture was adjusted to pH 11 with 5M NaOH and extracted with EE (4×20 ml). The organic phase was dried with $Na_2SO_4$ and concentrated by evaporation. The product was a mixture of two diastereoisomeric compounds. The diastereoisomer mixture was obtained as a colourless solid in a yield of 343 mg (80%).

{4-[4-(5-methoxy-1H-indol-3-yl)-3,6-dihydro-2H-pyridine-1-yl]-1-phenylcyclohexyl}-dimethylamine dihydrochloride To prepare the hydrochloride the diastereoisomer mixture of {4-[4-(5-methoxy-1H-indol-3-yl)-3,6-dihydro-2H-pyridine-1-yl]-1-phenylcyclohexyl}-dimethylamine (343 mg, 0.8 mmole) was dissolved in ethyl methyl ketone (5 ml) and chlorotrimethylsilane (255 µl, 2.0 mmole) was added. The solid thereby formed was filtered off and dried. The hydrochloride was thereby obtained in a yield of 400 mg (100%) as a colourless solid (Example 57) with an m.p. of 201°-203° C.

Examples 58 and 59

4-(5-chloro-1H-indol-3-yl)-3,6-dihydro-2H-pyridine-1-carboxylic acid-(4-dimethylamino-4-phenyl-cyclohexylmethyl)-amide hydrochloride (4-dimethylamino-4-phenylcyclohexylmethyl)-carbamic acid phenyl ester The chloroformic acid phenyl ester (1.32 ml, 10.5 mmole) dissolved in abs. DCM (25 ml) was slowly added dropwise while cooling with iced water to a solution of (4-aminomethyl-1-phenylcyclohexyl)-dimethylamine (2.32 g, 10 mmole) in abs. DCM (25 ml) and pyridine (888 µl, 11 mmole). The reaction mixture was then stirred for 20 hours at RT. The reaction mixture was worked up by extraction with water (3×10 ml), with 1M HCL (3×10 ml) and with 1M NaOH (2×10 ml). The organic phase was dried with $Na_2SO_4$ and then concentrated by evaporation. The residue was the diastereoisomer mixture of (4-dimethyl-amino-4-phenylcyclohexylmethyl)-carbamic acid phenyl ester. This was obtained as a colourless solid in a yield of 3.18 g (m.p. 108°-124° C., 90%).

4-(5-chloro-1H-indol-3-yl)-3,6-dihydro-2H-pyridine-1-carboxylic acid-(4-dimethylamino-4-phenyl-cyclohexylmethyl)-amide The diastereoisomer mixture of (4-dimethylamino-4-phenylcyclohexylmethyl)-carbamic acid phenyl ester (705 mg, 2 mmole) was added to a solution of 5-chloro-3-(1,2,3,6-tetrahydropyridine-4-yl)-1H-indole (465.4 mg, 2 mmole) in dioxane (12 ml). The reaction mixture was then boiled under reflux for 20 hours. The reaction mixture was a suspension at RT. The solid was filtered off, washed with cold dioxane (3×2 ml) and dried. The solid was the polar diastereoisomer of 4-(5-chloro-1H-indol-3-yl)-3,6-dihydro-2H-pyridine-1-carboxylic acid-(4-dimethylamino-4-phenylcyclohexylmethyl)-amide (259 mg, m.p. 120°-130° C., 26%). The reaction solution (filtrate and wash phases) was concentrated by evaporation and water (10 ml) was added to the residue. The reaction mixture was adjusted to pH 11 with 5M NaOH and extracted with EE (3×20 ml). The combined EE extracts were washed with 1M NaOH (1×5 ml) and dried with $Na_2SO_4$. The solvent was distilled off in vacuo. The residue contained phenol and mainly the non-polar diastereoisomer of 4-(5-chloro-1H-indol-3-yl)-3,6-dihydro-2H-pyridine-1-carboxylic acid-(4-dimethylamino-4-phenylcyclohexylmethyl)-amide. The diastereoisomers were separated and purified by flash chromatography on silica gel (80 g). Ethanol (1000 ml) was used as eluent. The non-polar diastereoisomer of 4-(5-chloro-1H-indol-3-yl)-3,6-dihydro-2H-pyridine-1-carboxylic acid-(4-dimethylamino-4-phenylcyclohexylmethyl)-amide (304 mg, m.p. 216°-222° C., 31%) and a further part of the polar diastereoisomer of 4-(5-chloro-1H-indol-3-yl)-3,6-dihydro-2H-pyridine-1-carboxylic acid-(4-dimethylamino-4-phenylcyclohexylmethyl)-amide (85 mg, m.p. 108°-111° C., 9%) were thereby isolated.

4-(5-chloro-1H-indol-3-yl)-3,6-dihydro-2H-pyridine-1-carboxylic acid-(4-dimethylamino-4-phenyl-cyclohexylmethyl)-amide hydrochloride The non-polar diastereoisomer of 4-(5-chloro-1H-indol-3-yl)-3,6-dihydro-2H-pyridine-1-carboxylic acid-(4-dimethylamino-4-phenylcyclohexylmethyl)-amide (288 mg, 0.59 mmole) was dissolved in acetone (25 ml) and ethanol (25 ml). 5M isopropanolic hydrochloric acid (176 µl, 0.88 mmole) was added dropwise at RT to the suspension while stirring. A clear solution spontaneously formed, from which no precipitate was obtained after stirring for 1 hour at RT. The reaction solution was reduced to 2 ml in vacuo and diethyl ether (50 ml) was slowly added. The reaction mixture was then stirred vigorously for 2 hours at RT. An orange precipitate formed. The solid was filtered off, washed with diethyl ether (3×3 ml) and dried in vacuo. The non-polar diastereoisomer of 4-(5-chloro-1H-indol-3-yl)-3,6-dihydro-2H-pyridine-1-carboxylic acid-(4-dimethylamino-4-phenylcyclohexylmethyl)-amide was thereby obtained in a yield of 308 mg (m.p. 191°-193° C., 99%) as a cinnamon-coloured solid (Example 58).

The polar diastereoisomer of 4-(5-chloro-1H-indol-3-yl)-3,6-dihydro-2H-pyridine-1-carboxylic acid-(4-dimethylamino-4-phenylcyclohexylmethyl)-amide (246 mg, 0.5 mmole) was dissolved in ethyl methyl ketone (10 ml). Chlorotrimethylsilane (95 µl, 0.75 mmole) was added dropwise at RT while stirring. After stirring for 1 hour a small amount of precipitate had formed. Diethyl ether (35 ml) was added to the reaction solution. The reaction solution was then stirred vigorously for 2 hours at RT. An orange precipitate formed. The solid was filtered off under suction, washed with diethyl ether (3×2 ml) and dried in vacuo. The hydrochloride of the polar diastereoisomer of 4-(5-chloro-1H-indol-3-yl)-3,6-dihydro-2H-pyridine-1-carboxylic acid-(4-dimethylamino-4-phenylcyclohexylmethyl)-amide (207 mg, m.p. 183°-185° C., 78%) was thereby obtained as a cinnamon-coloured solid (Example 59).

Example 60

2-(4-dimethylamino-4-(4-fluorophenyl)cyclohexylidene)-1-[3-(1H-indol-3-yl)pyrrolidine-1-yl]-ethanone hydrochloride

2-(4-dimethylamino-4-(4-fluorophenyl)cyclohexylidene)-1-[3-(1H-indol-3-yl)pyrrolidine-1-yl]-ethanone 1-hydroxybenzotriazole (1.08 mg, 8 mmole), 3-pyrrolidine-3-yl-1H-indole (744 mg, 4 mmole) and N-methylmorpholine (0.888 ml, 8 mmole) were added in succession under argon to a solution of [4-dimethylamino-4-(4-fluorophenyl)-cyclohexylidene)-acetic acid (1.055 g, 4 mmole) in dry dimethylformamide (40 ml). The clear solution was cooled in an ice bath and dicyclohexylcarbodiimide (1.65 g, 8 mmole) was added. The reaction mixture was stirred for 5 days at room temperature, the dicyclohexylurea precipitating out little by little. The reaction mixture was worked up by separating the precipitated urea and adding the filtrate to a mixture of saturated NaCl solution (40 ml) and saturated NaHCO$_3$ solution (10 ml). Further urea thereupon precipitated out, which was separated. The filtrate was diluted with water (300 ml) and 5M sodium hydroxide (7 ml, 35 mmole) was added. The crude product of 2-(4-dimethylamino-4-(4-fluorophenyl)cyclohexylidene)-1-[3-(1H-indol-3-yl)pyrrolidine-1-yl]-ethanone thereupon precipitated out as a beige-coloured solid (1.67 g). The chromatographic separation on silica gel (80 g) was carried out with EE/methanol (1:1). 2-(4-dimethylamino-4-(4-fluorophenyl)cyclohexylidene)-1-[3-(1H-indol-3-yl)pyrrolidine-1-yl]-ethanone was thereby obtained as a diastereoisomer mixture in a yield of 52% (916 mg) in the form of a colourless solid with a melting point of 109°-112° C.

2-(4-dimethylamino-4-(4-fluorophenyl)cyclohexylidene)-1-[3-(1H-indol-3-yl)pyrrolidine-1-yl]-ethanone hydrochloride Chlorotrimethylsilane (0.13 ml, 1.01 mmole) was added to a solution of 2-(4-dimethylamino-4-(4-fluorophenyl)-cyclohexylidene)-1-[3-(1H-indol-3-yl)pyrrolidine-1-yl]ethanone (300 mg, 0.67 mmole) in ethyl methyl ketone (25 ml) and stirred for 2 hours at RT. The hydrochloride (300 mg, 93%) thereupon precipitated as a diastereoisomer mixture with a melting point of 189°-194° C. in the form of a colourless solid (Example 60).

Example 61

Dimethyl-(1-phenyl-4-piperidine-1-ylcyclohexyl) amine dihydrochloride (polar diastereoisomer)

Dimethyl-(1-phenyl-4-piperidine-1-ylcyclohexyl) amine

Piperidine (400 µl, 4 mmole) and 4-dimethylamino-4-phenylcyclohexanone (434 mg, 2 mmole) were dissolved in dry 1,2-dichloroethane (10 ml). Glacial acetic acid (2 mmole) and sodium triacetoxy boron hydride (600 mg, 2.8 mmole) were added to this mixture and the whole was stirred for 24 hours at RT. The reaction mixture was worked up by distilling off the 1,2-dichloroethane and the mixture was adjusted to pH 11 with 5M NaOH. The alkaline phase was diluted with water (10 ml) and extracted with EE (3×20 ml). The organic phase was dried with Na$_2$SO$_4$ and concentrated by evaporation. Dimethyl-(1-phenyl-4-piperidine-1-ylcyclohexyl)-amine was purified by chromatography with ethanol. The non-polar diastereoisomer (15 mg) still contained impurities, which also could not be removed by further purification attempts. The polar diastereoisomer was obtained as a colourless oil in a yield of 92 mg (16%).

Dimethyl(1-phenyl-4-piperidine-1-ylcyclohexyl) amine dihydrochloride (polar diastereoisomer)

To prepare the hydrochloride the polar diastereoisomer of dimethyl(1-phenyl-4-piperidine-1-ylcyclohexyl)amine (92 mg, 0.32 mmole) was dissolved in ethyl methyl ketone (4 ml) and trimethylchlorosilane (102 µl, 0.8 mmole) was added. The solid thereby obtained was filtered off and dried. The hydrochloride of dimethyl(1-phenyl-4-piperidine-1-ylcyclohexyl)amine was thereby obtained as a colourless solid (Example 61) with an m.p. of 260°-261° C. in a yield of 103 mg (100%).

EXAMPLE TABLE

| Example No. | Structure | Salt Form | Remarks |
| --- | --- | --- | --- |
| 1 | 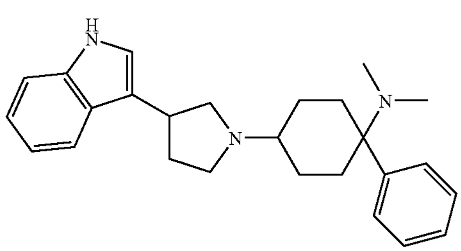 | Dihydrochloride | Non-polar diastereoisomer |

EXAMPLE TABLE-continued

| Example No. | Structure | Salt Form | Remarks |
|---|---|---|---|
| 2 | (indole-pyrrolidine-cyclohexyl-N(CH3)2-phenyl structure) | Dihydrochloride | Mixture |
| 3 | (5-Cl-indole-piperidine-cyclohexyl-N(CH3)2-phenyl structure) | Dihydrochloride | Non-polar diastereoisomer |
| 4 | (5-Cl-indole-piperidine-cyclohexyl-N(CH3)2-phenyl structure) | Dihydrochloride | Polar diastereoisomer |
| 5 | (indole-piperidine-cyclohexyl-N(CH3)2-phenyl structure) | Dihydrochloride | Polar diastereoisomer |
| 6 | (indole-piperidine-cyclohexyl-N(CH3)2-phenyl structure) | Dihydrochloride | Non-polar diastereoisomer |
| 7 | (6-methoxy-indole-piperidine-cyclohexyl-N(CH3)2-phenyl structure) | Dihydrochloride | Non-polar diastereoisomer |

EXAMPLE TABLE-continued

| Example No. | Structure | Salt Form | Remarks |
| --- | --- | --- | --- |
| 8 | 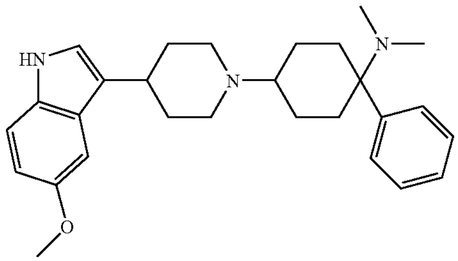 | Dihydrochloride | Polar diastereoisomer |
| 9 | 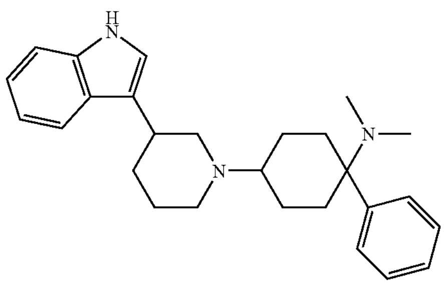 | Dihydrochloride | Non-polar diastereoisomer |
| 10 | 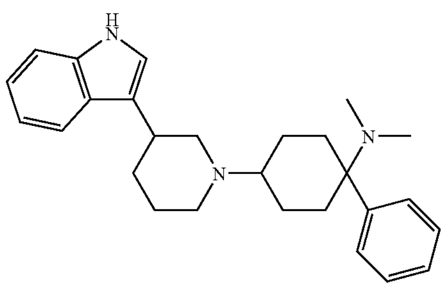 | Dihydrochloride | Polar diastereoisomer |
| 11 | 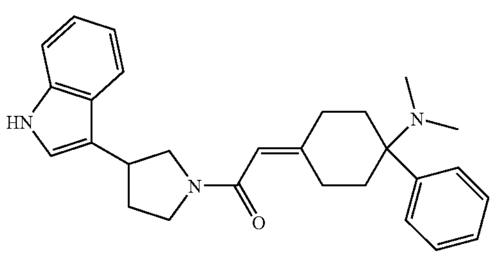 | Hydrochloride | Diastereoisomer mixture |
| 12 | 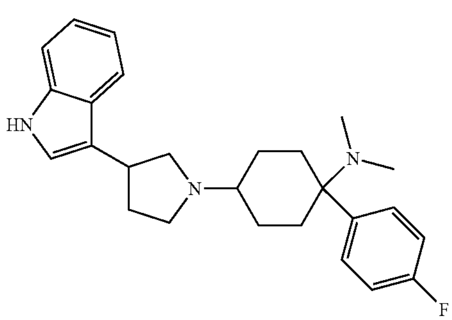 | Dihydrochloride | Polar diastereoisomer |

EXAMPLE TABLE-continued

| Example No. | Structure | Salt Form | Remarks |
| --- | --- | --- | --- |
| 13 | 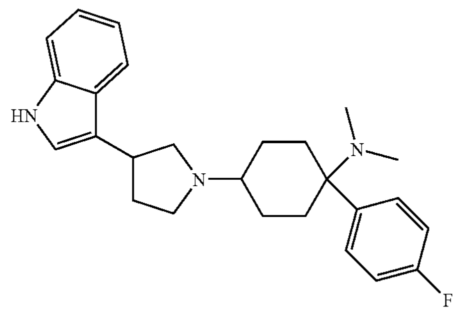 | Dihydrochloride | Non-polar diastereoisomer |
| 14 | 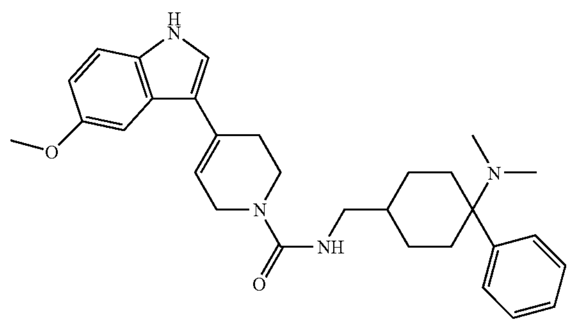 | Citrate | Non-polar diastereoisomer |
| 15 | 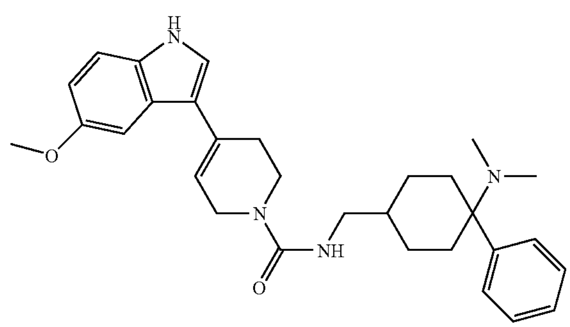 | Citrate | Polar diastereoisomer |
| 16 | 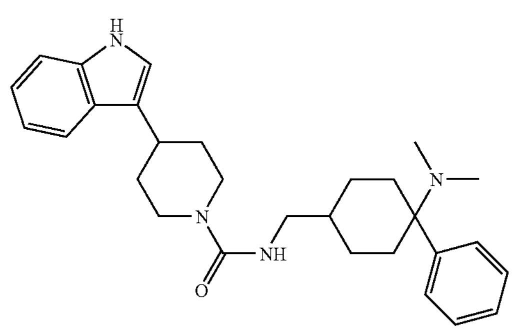 | Hemicitrate | Non-polar diastereoisomer |

EXAMPLE TABLE-continued
| Example No. | Structure | Salt Form | Remarks |
|---|---|---|---|
| 17 | 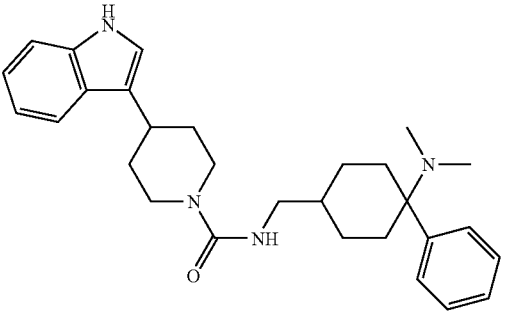 | Citrate | Non-polar diastereoisomer |
| 18 | 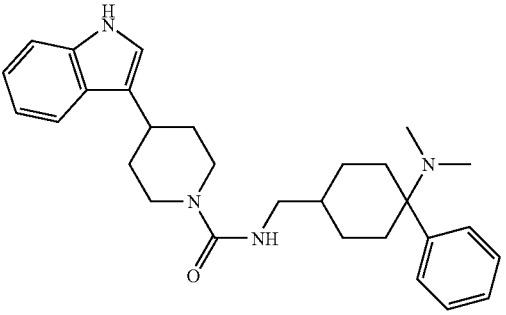 | Citrate | Polar diastereoisomer |
| 19 | 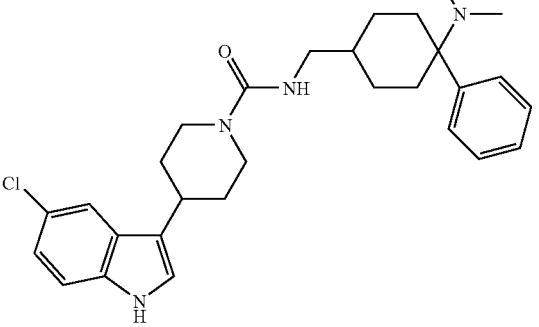 | Citrate | Polar diastereoisomer |
| 20 | 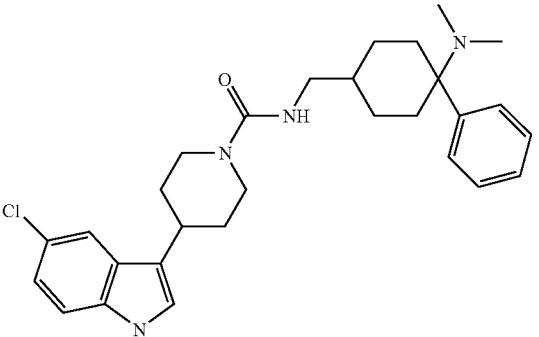 | Hemicitrate | Non-polar diastereoisomer |
| 21 | 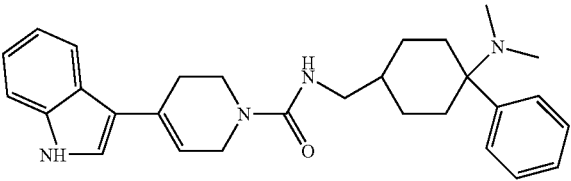 | Citrate | Non-polar diastereoisomer |

EXAMPLE TABLE-continued

| Example No. | Structure | Salt Form | Remarks |
|---|---|---|---|
| 22 | 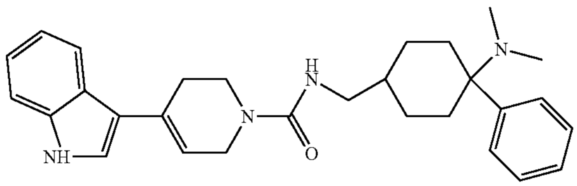 | Citrate | Polar diastereoisomer |
| 23 | 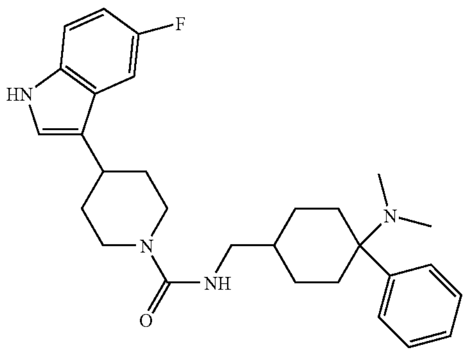 | Hemicitrate | Non-polar diastereoisomer |
| 24 | 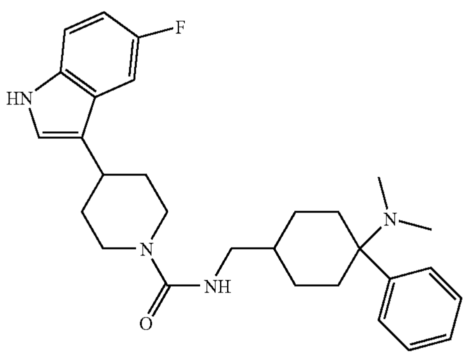 | Citrate | Polar diastereoisomer |
| 25 | 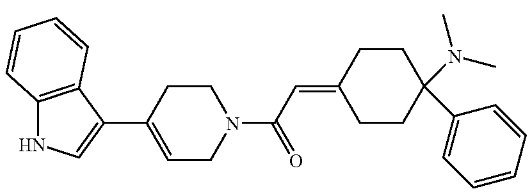 | Hydrochloride | |
| 26 | 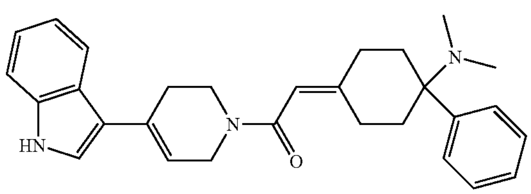 | Hydrochloride | |
| 27 | 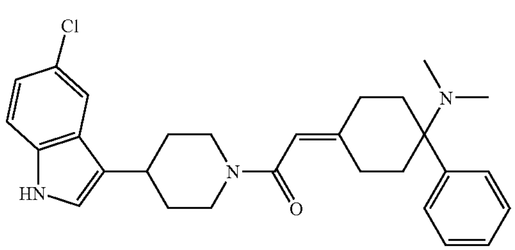 | Hydrochloride | |

EXAMPLE TABLE-continued

| Example No. | Structure | Salt Form | Remarks |
|---|---|---|---|
| 28 | 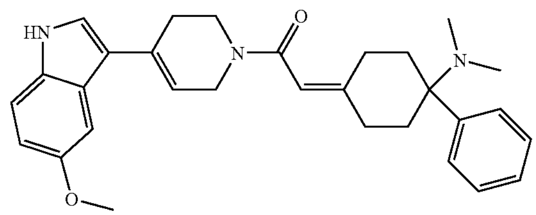 | Hydrochloride | |
| 29 | 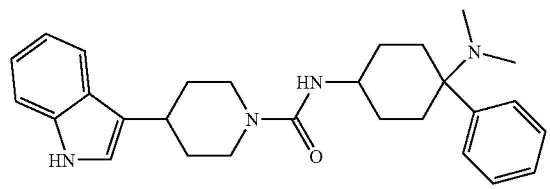 | Hydrochloride | Non-polar diastereoisomer |
| 30 | 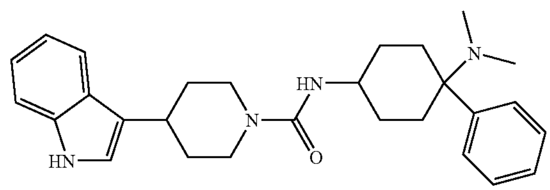 | Hydrochloride | Polar diastereoisomer |
| 31 | 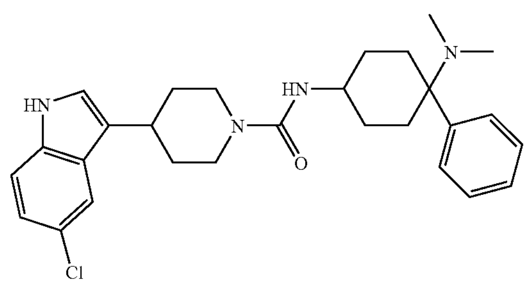 | Hydrochloride | Non-polar diastereoisomer |
| 32 | 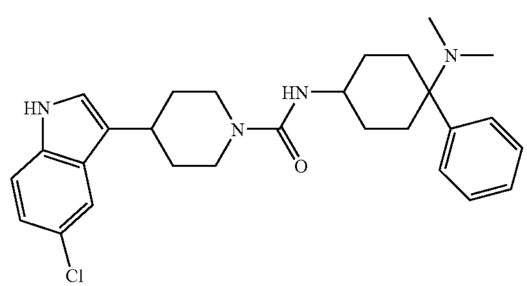 | Hydrochloride | Non-polar diastereoisomer |
| 33 | 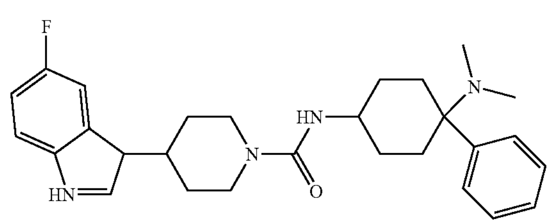 | Hydrochloride | Non-polar diastereoisomer |

EXAMPLE TABLE-continued

| Example No. | Structure | Salt Form | Remarks |
| --- | --- | --- | --- |
| 34 | 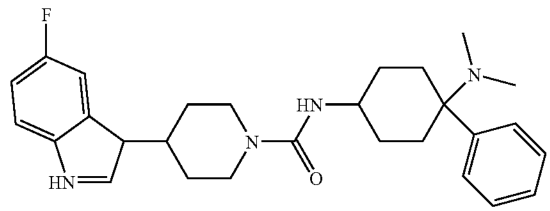 | Hydrochloride | Polar diastereoisomer |
| 35 | 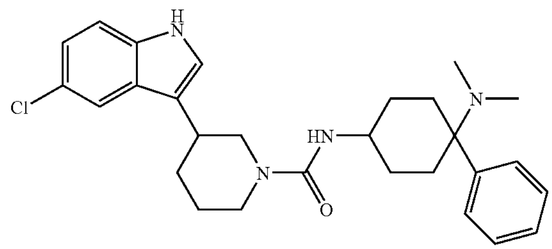 | Hydrochloride | Non-polar diastereoisomer |
| 36 | 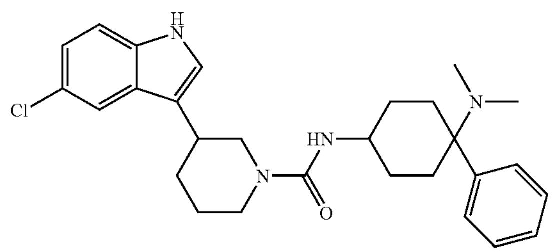 | Hydrochloride | Polar diastereoisomer |
| 37 | 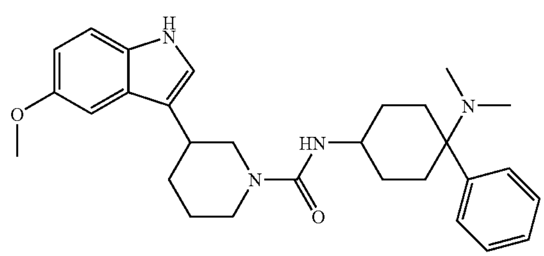 | Hydrochloride | Non-polar diastereoisomer |
| 38 | 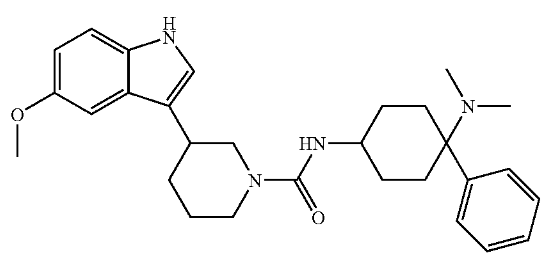 | Hydrochloride | Polar diastereoisomer |
| 39 | 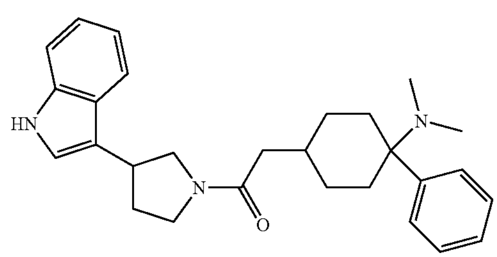 | Hydrochloride | One of two diastereoisomers |

EXAMPLE TABLE-continued
| Example No. | Structure | Salt Form | Remarks |
|---|---|---|---|
| 40 | 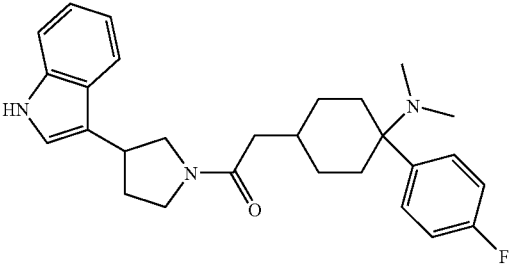 | Hydrochloride | Non-polar diastereoisomer |
| 41 | 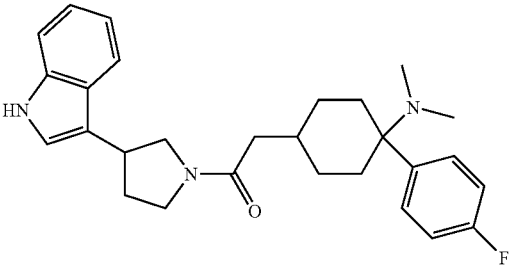 | Hydrochloride | Polar diastereoisomer |
| 42 | 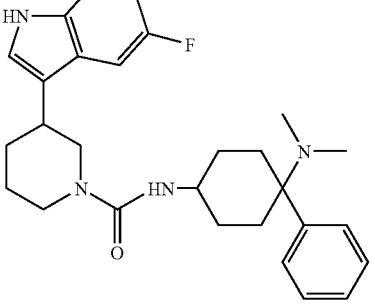 | Hydrochloride | Polar diastereoisomer |
| 43 | 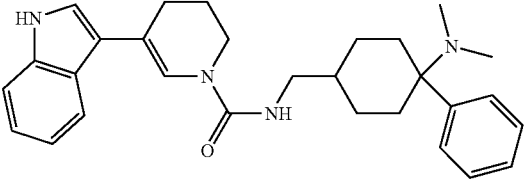 | Citrate | Non-polar diastereoisomer |
| 44 | 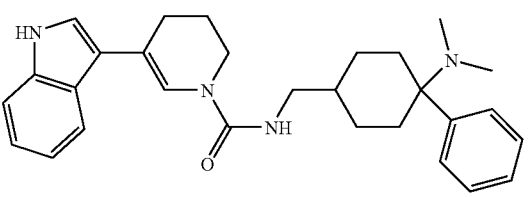 | Citrate | Polar diastereoisomer |

EXAMPLE TABLE-continued

| Example No. | Structure | Salt Form | Remarks |
|---|---|---|---|
| 45 | 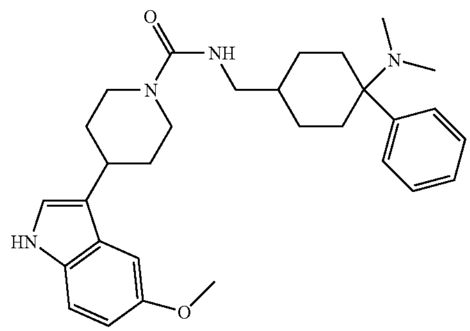 | Citrate | Non-polar diastereoisomer |
| 46 | 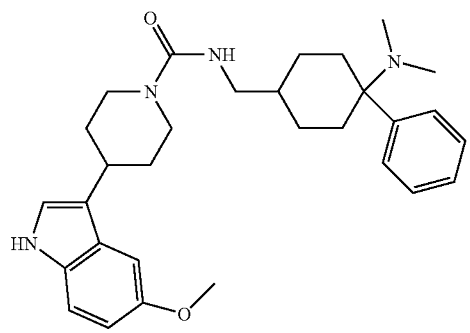 | Citrate | Polar diastereoisomer |
| 47 | 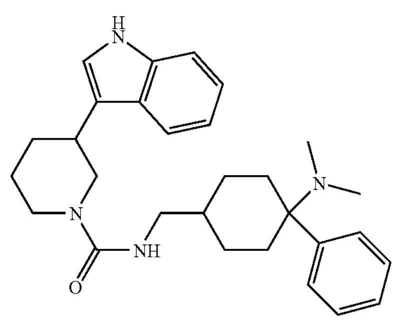 | Citrate | Non-polar diastereoisomer |
| 48 | 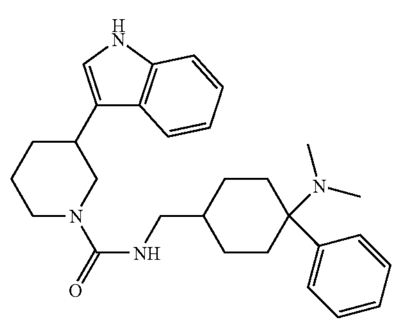 | Citrate | Polar diastereoisomer |
| 49 | 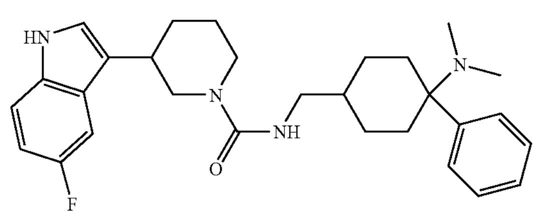 | Citrate | Non-polar diastereoisomer |

EXAMPLE TABLE-continued

| Example No. | Structure | Salt Form | Remarks |
|---|---|---|---|
| 50 | 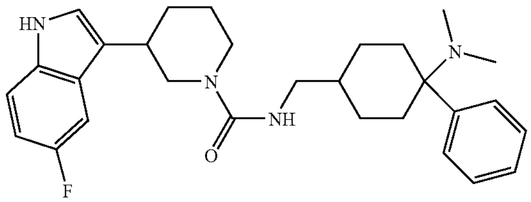 | Citrate | Polar diastereoisomer |
| 51 | 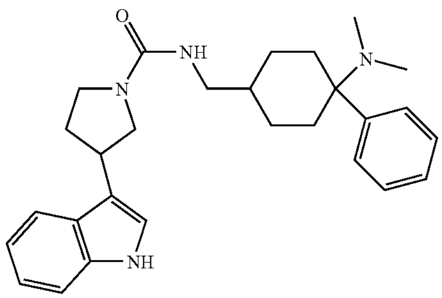 | Citrate | Non-polar diastereoisomer |
| 52 | 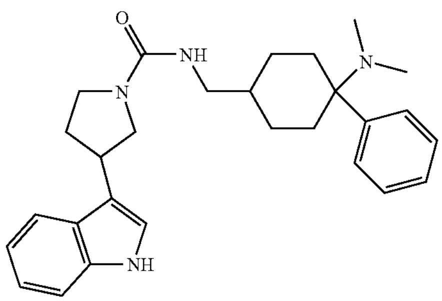 | Citrate | Polar diastereoisomer |
| 53 | 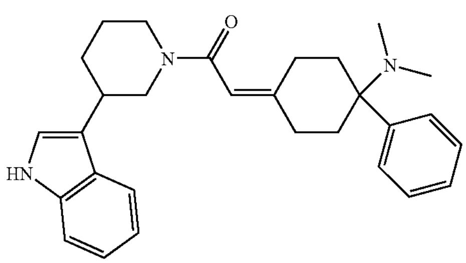 | Hydrochloride | Diastereoisomer mixture |
| 54 | 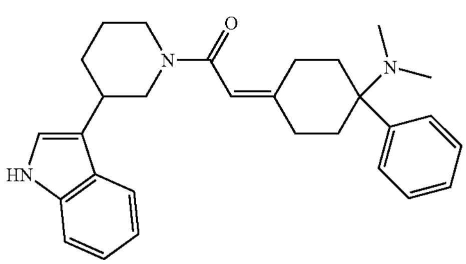 | Hydrochloride | Diastereoisomer mixture |
| 55 | 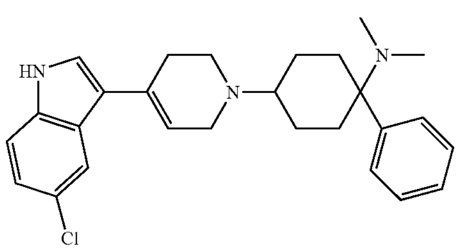 | Dihydrochloride | Diastereoisomer mixture |

EXAMPLE TABLE-continued

| Example No. | Structure | Salt Form | Remarks |
| --- | --- | --- | --- |
| 56 | 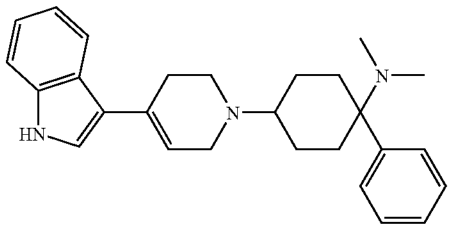 | Dihydrochloride | Diastereoisomer mixture |
| 57 | 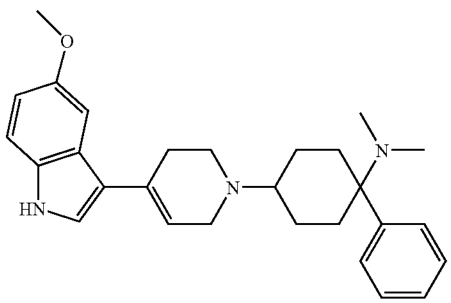 | Dihydrochloride | Diastereoisomer mixture |
| 58 | 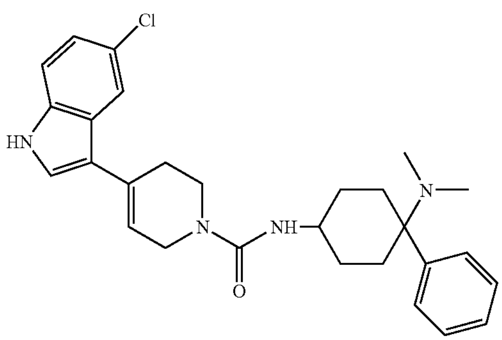 | Hydrochloride | Non-polar diastereoisomer |
| 59 | 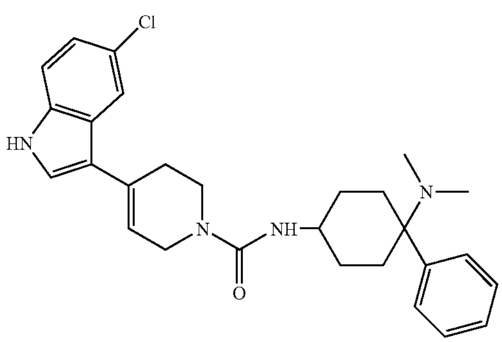 | Hydrochloride | Polar diastereoisomer |
| 60 | 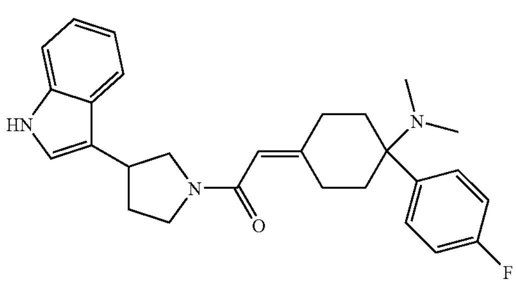 | Hydrochloride | Diastereoisomer mixture |

EXAMPLE TABLE-continued

| Example No. | Structure | Salt Form | Remarks |
|---|---|---|---|
| 61 | (structure) | Dihydrochloride | Polar diastereoisomer |

Investigations on the Efficacy of the Compounds According to the Invention:

The data obtained in the following assays and models are summarised in Table 1.

Measurement of the ORL1 Binding

The cyclohexane derivatives of the general formula I were investigated in a receptor binding assay with $^3$H-nociceptin/orphanin FQ with membranes of recombinant CHO-ORL1 cells. This test system was carried out according to the method proposed by Ardati et al. (Mol. Pharmacol., 51, 1997, pp. 816-824). In these tests the concentration of $^3$H-nociceptin/orphanin FQ was 0.5 nM. The binding assays were carried out with 20 µg of membrane protein per 200 µl of batch in 50 mM Hepes, pH 7.4, 10 mM $MgCl_2$ and 1 mM EDTA.

The binding to the ORL1 receptor was determined using in each case 1 mg WGA-SPA beads (Amersham-Pharmacia, Freiburg), by incubating the batch for 1 hour at RT followed by measurement in a Trilux scintillation counter (Wallac, Finland). The affinity is given in Table 1 as nanomolar $K_j$ value in or % inhibition at c=1 µM.

Measurement of the µ Bonding

The receptor affinity for the human µ opiate receptor was determined in a homogeneous batch in microtitre plates. For this purpose dilution series of the substituted spirocyclic cylcohexane derivative to be tested in each case were incubated with a receptor membrane preparation (15-40 µg protein per 250 µl of incubation batch) of CHO-K1 cells that express the human ti opiate receptor (RB-HOM receptor membrane preparation from NEN, Zaventem, Belgium) in the presence of 1 nmole/l of the radioactive ligand [$^3$H]-naloxone (NET719, NEN, Zaventem, Belgium) as well as 1 mg WGA-SPA beads (wheatgerm agglutinin SPA beads from Amersham/Pharmacia, Freiburg, Germany) in a total volume of 250 µl for 90 minutes at room temperature. 50 mmole/l tris-HCl supplemented with 0.05 wt. % of sodium azide and with 0.06 wt. % of bovine serum albumin was used as incubation buffer. To determine the non-specific binding, 25 µmole/l of naloxone were additionally added. After completion of the 90-minute incubation period the microtitre plates were centrifuged for 20 minutes at 1000 g and the radioactivity was measured in a β counter (Microbeta-Trilux, PerkinElmer Wallac, Freiburg, Germany). The percentage displacement of the readioactive ligand from its binding to the human µ opitate receptor was determined at a concentration of the test substances of 1 µmole/l and given as a percentage inhibition (% inhibition) of the specific binding. In some cases $IC_{50}$ inhibiting concentrations that produce a 50% displacement of the radioactive ligand were calculated on the basis of the percentage displacement by different concentrations of the compounds of the general formula I being tested. Ki values for the test substances were obtained by conversion by means of the Cheng-Prusoff relationship. In individual cases (identified by DA in Table 2) measurements were made using [D-Ala2, MePhe4,Gly-ol5]encephalin ("DAMGO") instead of naloxone.

Analgesia Investigation in the Tail Flick Test in Mice

The mice were in each case placed individually in a test cage and the base of the tail was exposed to the focused thermal radiation from an electric lamp (tail flick type 50/08/l.b.c., Labtec, Dr Hess). The lamp intensity was adjusted so that the time from when the lamp was switched on to the sudden withdrawal movement of the tail (pain latency) in untreated mice was 3 to 5 seconds. Before the application of the solutions containing the compound according to the invention or the respective comparison solutions, the mice were pre-tested twice within a period of 5 minutes and the mean value of these measurements was calculated as the pre-test mean value.

The solutions of the compounds according to the invention of the general formula I as well as the comparison solutions were then administered intravenously. The pain measurement was carried out in each case 10, 20, 40 and 60 minutes after the intravenous administration. The analgesic action was determined as the increase in the pain latency (% of the maximum possible antinociceptive effect) according to the following formula:

$$[(T_1-T_0)/(T_2-T_0)]\times 100$$

Here the time To is the latency time before the application, the time $T_1$ is the latency time after the application of the active substance combination, and the time $T_2$ is the maximum exposure duration (12 seconds).

TABLE 2

| Example No. | ORL1 Ki [µM] or % inhibition [1 µM] | µ Ki [µM] or % inhibition [1 µM] | Tail Flick (mice, i.v.) % inhibition (dose [mg/kg]) |
|---|---|---|---|
| 1 | 0.0038 | 0.0028 | |
| 2 | 0.012 | 0.0025 | |
| 3 | 0.032 | 0.019 | |
| 4 | 0.054 | 53% | |
| 5 | 0.069 | 36% | |
| 6 | 0.047 | 0.1 | |
| 7 | 0.065 | 0.039 | |
| 8 | 54% | 0.54 | |
| 9 | 0.0029 | 0.013 | |

TABLE 2-continued

| Example No. | ORL1 Ki [μM] or % inhibition [1 μM] | μ Ki [μM] or % inhibition [1 μM] | Tail Flick (mice, i.v.) % inhibition (dose [mg/kg]) |
|---|---|---|---|
| 10 | 0.1 | 61% | |
| 11 | 0.02 | 0.0008 | |
| 12 | 10% | 66% | |
| 13 | 0.087 | 0.022 | |
| 14 | 63% | 52% (DA) | |
| 15 | 0.1 | 0.03 (DA) | |
| 16 | 57% | 0.027 | |
| 17 | 0.21 | 0.0685 | |
| 18 | 0.068 | 0.024 | |
| 19 | 0.075 | 0.021 | |
| 20 | 46% | 0.026 | |
| 21 | 47% | 0.083 (DA) | |
| 22 | 0.083 | 0.11 (DA) | |
| 23 | 51% | 0.048 | |
| 24 | 0.058 | 0.027 | |
| 25 | 0.039 | 0.031 (DA) | |
| 26 | 0.095 | 0.041 | |
| 27 | 0.11 | 0.021 | |
| 28 | 0.067 | 0.024 (DA) | |
| 29 | 46% | 0.0071 | |
| 30 | 47% | 0.28 | |
| 31 | 59% | 0.013 | |
| 32 | 39% | 0.031 | |
| 33 | 62% | 0.0083 | |
| 34 | 66% | 0.12 | |
| 35 | 0.033 | 0.0081 | |
| 36 | 26% | 56% | |
| 37 | 0.083 | 0.019 | |
| 38 | 13% | 0.41 | |
| 39 | 0.021 | 0.0022 | |
| 40 | 14% | 0.022 | |
| 41 | 55% | 0.0059 | |
| 42 | 34% | 57% | |
| 43 | 0.16 | 0.015 (DA) | |
| 44 | 0.11 | 0.0057 (DA) | |
| 45 | 52% | 0.015 | |
| 46 | 0.092 | 0.07 | |
| 47 | 56% | 0.032 | |
| 48 | 0.091 | 0.0021 | 100 (21.5) |
| 49 | 61% | 0.022 | |
| 50 | 0.068 | 0.0033 | |
| 51 | 69% | 0.018 | |
| 52 | 0.045 | 0.01 | |
| 53 | 0.056 | 0.0031 | |
| 54 | 0.043 | 0.0079 | 100% (10) |
| 55 | 0.095 | 85% | |
| 56 | 0.17 | 90% | |
| 57 | 0.15 | 91% | |
| 58 | 0.12 | 0.031 (DA) | |
| 59 | 0.082 | 0.038 (DA) | |
| 60 | 45% | 0.022 | |
| 61 | 0.11 | 23% (DA) | |

Parenteral Solution of a 4-Substituted 1-Aminocyclohexane Derivative According to the Invention 38 g of one of the 4-substituted 1-aminocyclohexane derivatives according to the invention, in this case Example 1, is dissolved at room temperature in 1 litre of water for injection purpose and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:

1. A 4-substituted 1-aminocyclohexane compound corresponding to formula I,

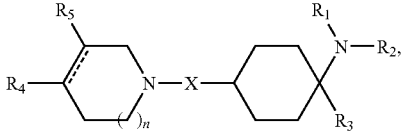

wherein
n=0,
X denotes a bond or C(O), C(O)NH, C(O)CH$_2$, C(O)CH= or C(O)NHCH$_2$,
$R^1$ and $R^2$ independently of one another denote H; methyl or ethyl, or
$R^1$ and $R^2$ together form a ring and denote $(CH_2)_5$,
$R^3$ denotes $C_{1-8}$-alkyl or $C_{3-8}$-cycloalkyl, in each case saturated or unsaturated, branched or unbranched, singly or multiply substituted or unsubstituted; aryl, heteroaryl, in each case unsubstituted or singly or multiply substituted; aryl, $C_{3-8}$-cycloalkyl or heteroaryl bonded via a saturated or unsaturated, branched or unbranched, substituted or unsubstituted $C_{1-4}$-alkyl group, in each case unsubstituted or singly or multiply substituted;
$R^4$ and $R^5$ independently of one another denote H; or $(CH_2)_m R^7$, wherein
m=0 and
$R^7$ is cyclopentyl, cyclohexyl, cycloheptyl, cyclooctyl, indolyl, naphthyl, benzofuranyl, benzothiophenyl, indanyl, acenaphthyl, phenyl, thiophenyl, furyl, pyridyl, pyrrolyl, pyrazinyl or pyrimidyl, in each case unsubstituted or singly or multiply substituted,
wherein only one of $R^4$ and $R^5$ may be H,
or a salt thereof with a physiologically tolerated acid.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. A 4-substituted 1-aminocyclohexane compound according to claim 1, wherein $R^1$ and $R^2$ independently of one another denote $CH_3$ or H, and $R^1$ and $R^2$ do not simultaneously denote H.

7. A 4-substituted 1-aminocyclohexane compound according to claim 1, wherein $R^3$ denotes $C_{3-8}$-cycloalkyl, aryl or heteroaryl, in each case unsubstituted or singly or multiply substituted; or aryl, $C_{3-8}$-cycloalkyl or heteroaryl bonded via a saturated or unsaturated, unbranched, substituted or unsubstituted $C_{1-2}$-alkyl group, in each case unsubstituted or singly or multiply substituted.

8. A 4-substituted 1-aminocyclohexane compound according to claim 1, wherein $R^3$ denotes cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or singly or multiply substituted; or $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group, in each case unsubstituted or singly or multiply substituted.

9. A 4-substituted 1-aminocyclohexane compound according to claim 1, wherein $R^3$ denotes phenyl, furyl, thiophenyl, naphthyl, benzyl, benzofuranyl, indolyl, indanyl, benzodioxanyl, benzodioxolanyl, pyridyl, pyrimidyl or pyrazinyl or benzothiophenyl, in each case unsubstituted or singly or multiply substituted; or phenyl, furyl or thiophenyl, bonded via a saturated, unbranched $C_{1-2}$-alkyl group, in each case unsubstituted or singly or multiply substituted.

10. A 4-substituted 1-aminocyclohexane compound according to claim 1, wherein $R^3$ denotes phenyl, thiophenyl, pyridyl or benzyl, in each case substituted or unsubstituted.

11. A 4-substituted 1-aminocyclohexane compound according to claim 1, wherein $R^3$ denotes phenyl.

12. A 4-substituted 1-aminocyclohexane compound according to claim 1, wherein $R^7$ denotes indolyl, unsubstituted or singly or multiply substituted.

13. A 4-substituted 1-aminocyclohexane compound according to claim 1, wherein one of $R^4$ and $R^5$ is H.

14. A 4-substituted 1-aminocyclohexane compound according to claim 1, wherein said compound is selected from the group consisting of:
  {4-[3-(1H-indol-3-yl)-pyrrolidine-1-yl]-1-phenyl-cyclohexyl}-dimethylamine; dihydrochloride (non-polar diastereoisomer)
  {4-[3-(1H-indol-3-yl)-pyrrolidine-1-yl]-1-phenyl-cyclohexyl}-dimethylamine; dihydrochloride (diastereoisomer mixture)
  2-(4-dimethylamino-4-phenylcyclohexylidene)-1-[3-(1H-indol-3-yl)pyrrolidine-1-yl]ethanone; hydrochloride (diastereoisomer mixture)
  {1-(4-fluorophenyl)-4-[3-(1H-indol-3-yl)pyrrolidine-1-yl]cyclohexyl}-dimethylamine; dihydrochloride (polar and non-polar diastereoisomer)
  2-(4-dimethylamino-4-phenylcyclohexyl)-1-[3-(1H-indol-3-yl)pyrrolidine-1-yl]-ethanone; hydrochloride
  2-[4-dimethylamino-4-(4-fluorophenyl)cyclohexyl]-1-[3-(1H-indol-3-yl)pyrrolidine-1-yl]-ethanone; hydrochloride (polar and non-polar diastereoisomer)
  3-(1H-indol-3-yl)pyrrolidine-1-carboxylic acid-(4-dimethylamino-4-phenylcyclohexyl-methyl)-amide; citrate (polar and non-polar diastereoisomer) and
  2-(4-dimethylamino-4-(4-fluorophenyl)cyclohexylidene)-1-[3-(1H-indol-3-yl)pyrrolidine-1-yl]-ethanone; hydrochloride (diastereoisomer mixture).

15. A pharmaceutical formulation comprising a pharmaceutically effective amount of at least one 4-substituted 1-aminocyclohexane compound according to claim 1 and a pharmaceutically acceptable carrier or adjuvant.

16. A method of alleviating pain in a mammal, said method comprising administering to said mammal an effective pain alleviating amount of a 4-substituted 1-aminocyclohexane compound according to claim 1.

17. The method of claim 16 wherein said pain is acute, visceral, neuropathic or chronic pain.

18. A process for preparing a compound according to claim 1 comprising:
  reacting a pyrrolidine compound according to formula III

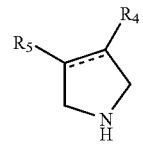

with a 4-aminocyclohexanone carbaldehyde or 4-aminocyclohexane carbaldehyde under reductive amination conditions.

19. The process of claim 18, wherein said process includes providing at least one hydride selected from the group consisting of sodium or lithium boron hydride, sodium cyano boron hydride, sodium triacetoxy boron hydride, diisobutyl aluminum hydride, lithium-tri-(sec.-butyl)boron hydride or lithium aluminum hydride.

20. A process for preparing a compound according to claim 1, comprising:
  reacting a pyrrolidine compound according to formula III

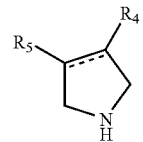

with a 4-aminocyclohexane-carboxylic acid compound or a 4-amino-cyclohexylacetic acid compound with the use of coupling reagents or after converting the carboxylic acid into an acid chloride or an active ester.

21. The process of claim 20, wherein said ester is a 4-nitrophenyl ester or an N-hydroxysuccinimide ester.

22. A process for preparing a compound according to claim 1, comprising:
  reacting, at a temperature of from 50° to 130° C., a pyrrolidine compound according to formula III

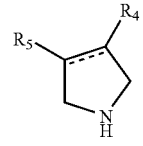

with a (4-aminocyclohexyl)-carbamic acid phenyl ester compound or a (4-aminocyclohexyl)-methyl-carbamic acid phenyl ester compound, which is prepared by reacting phenyl chloroformate and a 1,4-diaminocyclohexane compound or a 4-aminomethylcyclohexylamine compound.

* * * * *